(12) United States Patent
Kashiki et al.

(10) Patent No.: US 9,796,811 B2
(45) Date of Patent: Oct. 24, 2017

(54) POLYMER COMPOUND AND ORGANIC SEMICONDUCTOR DEVICE USING THE SAME

(71) Applicant: SUMITOMO CHEMICAL COMPANY, LIMITED, Tokyo (JP)

(72) Inventors: Tomoya Kashiki, Tsukuba (JP); Hiroki Terai, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/909,181

(22) PCT Filed: Aug. 21, 2014

(86) PCT No.: PCT/JP2014/072509
§ 371 (c)(1),
(2) Date: Feb. 1, 2016

(87) PCT Pub. No.: WO2015/025981
PCT Pub. Date: Feb. 26, 2015

(65) Prior Publication Data
US 2016/0159973 A1 Jun. 9, 2016

(30) Foreign Application Priority Data

Aug. 23, 2013 (JP) .................. 2013-172988

(51) Int. Cl.
*C08G 61/00* (2006.01)
*C08G 61/12* (2006.01)
(Continued)

(52) U.S. Cl.
CPC ......... *C08G 61/126* (2013.01); *C07D 495/04* (2013.01); *C07F 7/2212* (2013.01);
(Continued)

(58) Field of Classification Search
CPC ..................................... C08G 61/00
(Continued)

(56) References Cited

U.S. PATENT DOCUMENTS

2009/0171048 A1 7/2009 Chan et al.
2010/0171102 A1 7/2010 Ie et al.
(Continued)

FOREIGN PATENT DOCUMENTS

JP 2009-149846 A 7/2009
JP 2009-155648 A 7/2009
(Continued)

OTHER PUBLICATIONS

English translation of the International Search Report dated Dec. 9, 2014 in PCT/JP2014/072509.
(Continued)

*Primary Examiner* — Duc Truong
(74) *Attorney, Agent, or Firm* — Sughrue Mion, PLLC

(57) ABSTRACT

A polymer compound comprising a structural unit represented by the formula (1):

(Continued)

wherein Ring A and Ring B represent each independently a heterocyclic ring, and the heterocyclic ring may have a substituent, Ring C represents an aromatic hydrocarbon ring obtained by condensing two or more benzene rings, the aromatic hydrocarbon ring has at least one of an alkyl group, an alkoxy group, an alkylthio group, an amino group or a hydroxyl group, and these groups may have a substituent, $Z^1$ and $Z^2$ represent each independently a group represented by the formula (Z-1), a group represented by the formula (Z-2), a group represented by the formula (Z-3), a group represented by the formula (Z-4) or a group represented by the formula (Z-5),

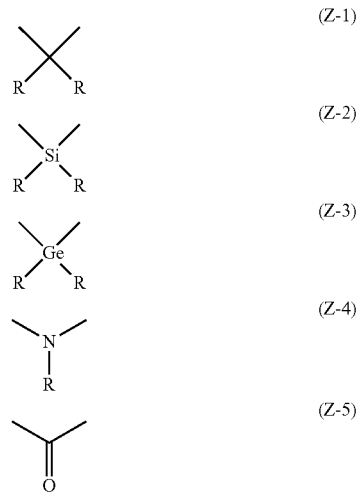

wherein R represents an alkyl group, an alkoxy group, an alkylthio group, an aryl group or a mono-valent heterocyclic group, and these groups may have a substituent, and when there exist a plurality of R, these may be the same or different.

16 Claims, 1 Drawing Sheet

(51) Int. Cl.

| | |
|---|---|
| *C07D 495/04* | (2006.01) |
| *H01L 51/00* | (2006.01) |
| *C07F 7/22* | (2006.01) |
| *C07D 495/00* | (2006.01) |
| *H01L 51/42* | (2006.01) |
| *H01L 51/05* | (2006.01) |
| *H01L 51/50* | (2006.01) |

(52) U.S. Cl.
CPC ...... *H01L 51/0036* (2013.01); *H01L 51/0043* (2013.01); *C08G 2261/12* (2013.01); *C08G 2261/124* (2013.01); *C08G 2261/146* (2013.01); *C08G 2261/1412* (2013.01); *C08G 2261/3223* (2013.01); *C08G 2261/3243* (2013.01); *C08G 2261/3246* (2013.01); *C08G 2261/344* (2013.01); *C08G 2261/414* (2013.01); *C08G 2261/91* (2013.01); *C08G 2261/92* (2013.01); *C08G 2261/94* (2013.01); *C08G 2261/95* (2013.01); *H01L 51/0508* (2013.01); *H01L 51/42* (2013.01); *H01L 51/4253* (2013.01); *H01L 51/5012* (2013.01)

(58) Field of Classification Search
USPC .......................................................... 528/401
See application file for complete search history.

(56) References Cited

U.S. PATENT DOCUMENTS

| | | |
|---|---|---|
| 2012/0322966 A1 | 12/2012 | Bazan et al. |
| 2013/0324685 A1 | 12/2013 | Aso et al. |
| 2014/0291660 A1 | 10/2014 | Takaku et al. |
| 2015/0065671 A1 | 3/2015 | Terai |

FOREIGN PATENT DOCUMENTS

| | | |
|---|---|---|
| JP | 2012-500308 A | 1/2012 |
| WO | 2008/111461 A1 | 9/2008 |
| WO | 2010/020329 A1 | 2/2010 |
| WO | 2010/041687 A1 | 4/2010 |
| WO | 2012/058209 A1 | 5/2012 |
| WO | 2012/105511 A1 | 8/2012 |
| WO | 2012/105517 A1 | 8/2012 |
| WO | 2013/010614 A2 | 1/2013 |
| WO | 2013/064881 A2 | 5/2013 |
| WO | 2013/161728 A1 | 10/2013 |
| WO | 2014/086457 A1 | 6/2014 |

OTHER PUBLICATIONS

English translation of the Written Opinion of the International Searching Authority dated Dec. 9, 2014 issued in PCT/JP2014/072509.
W. Zhang et al., "Indacenodithiophene Semiconducting Polymers for High-Performance, Air-Stable Transistors", J. A,. Chem. Soc. 2010, 132, pp. 11437-11439.
Y. Ma et al., "Ladder-Type Dithienonaphthalene-Based Donor-Acceptor Copolymers for Organic Solar Cells", Macromolecules, ACS Publications, American Chemical Society, 2013, pp. 4813-4821.
J. Pina et al., "Photophysical and Spectroscopic Investigations on (Oligo) Thiophene-Arylene Step-ladder Copolymers. The Interplay of Conformational Relaxation and On-Chain Energy Transfer", J. Phys. Chem. B, vol. 113, No. 49, 2009, pp. 15928-15936.

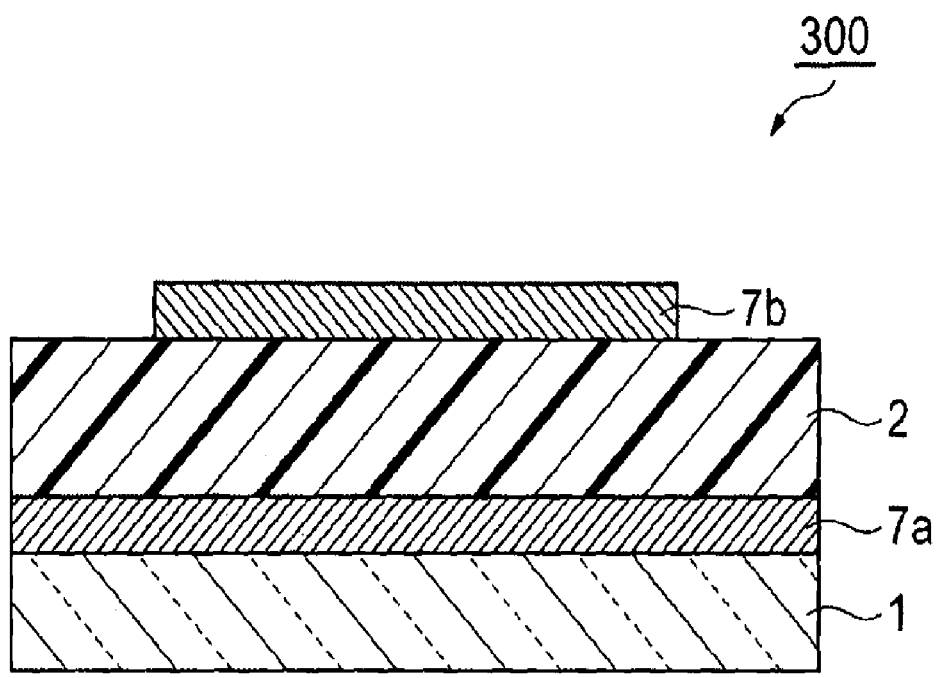

POLYMER COMPOUND AND ORGANIC SEMICONDUCTOR DEVICE USING THE SAME

CROSS REFERENCE TO RELATED APPLICATIONS

This application is a National Stage of International Application No. PCT/JP2014/072509 filed Aug. 21, 2014, claiming priority based on Japanese Patent Application No. 2013-172988, filed Aug. 23, 2013, the contents of all of which are incorporated herein by reference in their entirety.

TECHNICAL FIELD

The present invention relates to a polymer compound and an organic semiconductor device using the same.

BACKGROUND ART

Recently, for preventing global warming, the amount of $CO_2$ released into atmosphere is required to be reduced. Therefore, there is a suggestion of a solar system using a pn-junction type silicon-based solar battery as one embodiment of electronic devices. However, since a silicon-based solar battery is produced by using as a raw material a material selected from monocrystalline silicon, polycrystalline silicon and amorphous silicon, its production needs a high-temperature process and a high-vacuum process.

In contrast, in the case of an organic film solar battery having an active layer using a polymer compound, a high-temperature process and a high-vacuum process used in the production process of the silicon-based solar battery can be omitted, and the organic film solar battery can be possibly produced at low cost only by a coating process, thus is attracting attention. As the polymer compound used in the organic film solar battery, a polymer compound composed of a structural unit (A) and a structural unit (B) shown below is proposed (non-patent document 1).

Structural unit (A)

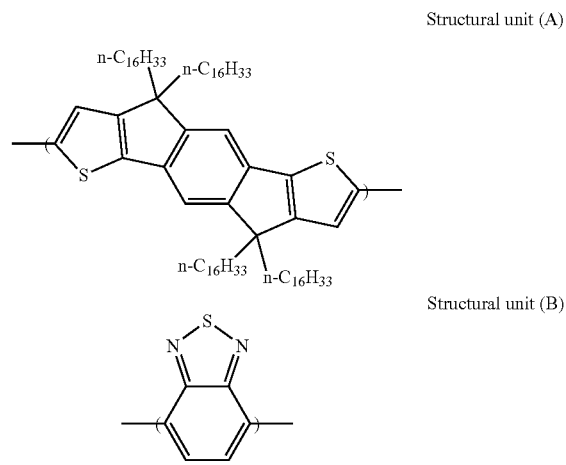

Structural unit (B)

PRIOR ART DOCUMENT

Non-Patent Document

Non-patent document 1: J. Am. Chem. Soc., 2010, 132, 11437-11439

SUMMARY OF THE INVENTION

However, the organic film solar battery having an active layer using the polymer compound is not necessarily sufficient in ff (fill factor).

The present invention has an object of providing a polymer compound which is useful for production of an organic film solar battery excellent in ff (fill factor).

The present invention is as described below.

[1] A polymer compound comprising a structural unit represented by the formula (1):

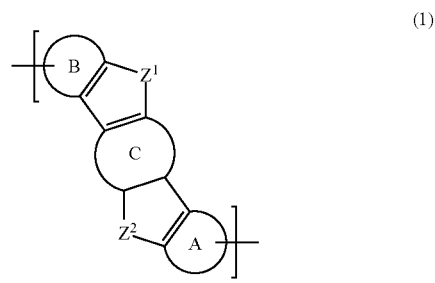

(1)

[wherein

Ring A and Ring B represent each independently a heterocyclic ring, and the heterocyclic ring may have a substituent.

Ring C represents an aromatic hydrocarbon ring obtained by condensing two or more benzene rings, the aromatic hydrocarbon ring has at least one of an alkyl group, an alkoxy group, an alkylthio group, an amino group or a hydroxyl group, and these groups may have a substituent.

$Z^1$ and $Z^2$ represent each independently a group represented by the formula (Z-1), a group represented by the formula (Z-2), a group represented by the formula (Z-3), a group represented by the formula (Z-4) or a group represented by the formula (Z-5).

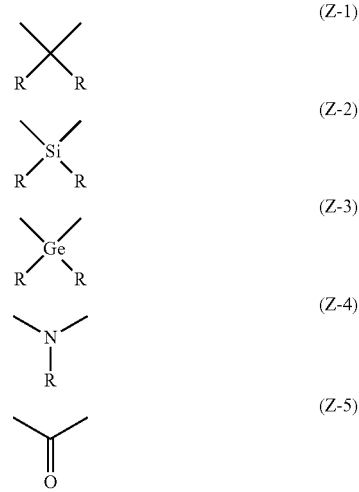

[wherein
R represents an alkyl group, an alkoxy group, an alkylthio group, an aryl group or a mono-valent heterocyclic group, and these groups may have a substituent. When there exist a plurality of R, these may be the same or different.].

[2] The polymer compound according to [1], wherein the structural unit represented by the formula (1) is a structural unit represented by the formula (2a):

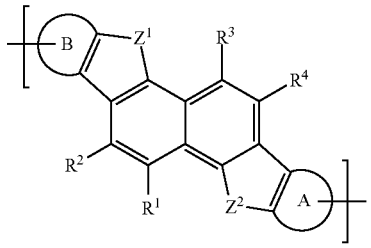

(2a)

[wherein

Ring A, Ring B, $Z^1$ and $Z^2$ represent the same meaning as described above.

$R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent. Here, at least one selected from the group consisting of $R^1$, $R^2$, $R^3$ and $R^4$ is an alkyl group, an alkoxy group, an alkylthio group, an amino group or a hydroxyl group.].

[3] The polymer compound according to [2], wherein the structural unit represented by the formula (2a) is a structural unit represented by the formula (3a):

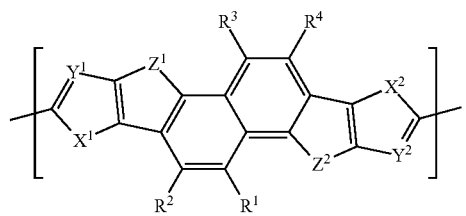

(3a)

[wherein $R^1$, $R^2$, $R^3$, $R^4$, $Z^1$ and $Z^2$ represent the same meaning as described above.

$X^1$ and $X^2$ represent each independently an oxygen atom, a sulfur atom or a selenium atom.

$Y^1$ and $Y^2$ represent each independently a nitrogen atom or a group represented by —$CR^5$=.

$R^5$ represents a hydrogen atom, an alkyl group, an alkoxy group, an alkylthio group, an aryl group, a mono-valent heterocyclic group or a halogen atom, and these groups may have a substituent.].

[4] The polymer compound according to [1], wherein the structural unit represented by the formula (1) is a structural unit represented by the formula (2b) or a structural unit represented by the formula (2c):

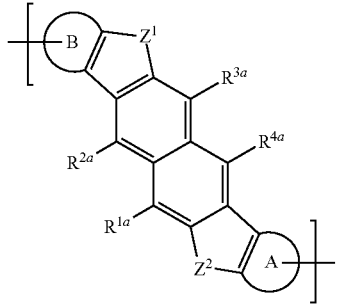

(2b)

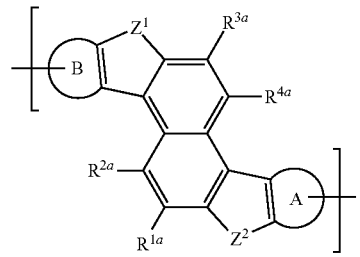

(2c)

[wherein

Ring A, Ring B, $Z^1$ and $Z^2$ represent the same meaning as described above.

$R^{1a}$, $R^{2a}$, $R^{3a}$ and $R^{4a}$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent. Here, at least one selected from the group consisting of $R^{1a}$, $R^{2a}$, $R^{3a}$ and $R^{4a}$ in the formula (2b) is an alkyl group, an alkoxy group, an alkylthio group, an amino group or a hydroxyl group, and at least one selected from the group consisting of $R^{1a}$, $R^{2a}$, $R^{3a}$ and $R^{4a}$ a in the formula (2c) is an alkyl group, an alkoxy group, an alkylthio group, an amino group or a hydroxyl group.].

[5] The polymer compound according to [3], wherein $X^1$ and $X^2$ are a sulfur atom.

[6] The polymer compound according to [3] or [5], wherein $Y^1$ and $Y^2$ are a group represented by —CH=.

[7] The polymer compound according to any one of [1] to [6], wherein $Z^1$ and $Z^2$ are the group represented by the formula (Z-1).

[8] The polymer compound according to any one of [1] to [7], further comprising a structural unit represented by the formula (4) (different from the structural unit represented by the formula (1)):

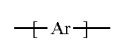

(4)

[wherein

Ar represents an arylene group or a di-valent heterocyclic group, and these groups may have a substituent.].

[9] The polymer compound according to [8], wherein the polymer compound is an alternative copolymer composed of the structural unit represented by the formula (1) and the structural unit represented by the formula.

[10] A compound represented by the formula (5a):

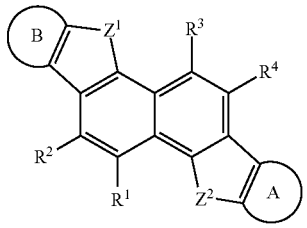

(5a)

[wherein

Ring A and Ring B represent each independently a heterocyclic ring, and the heterocyclic ring may have a substituent.

$Z^1$ and $Z^2$ represent each independently a group represented by the formula (Z-1), a group represented by the formula (Z-2), a group represented by the formula (Z-3), a group represented by the formula (Z-4) or a group represented by the formula (Z-5).

$R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent. Here, at least one selected from the group consisting of $R^1$, $R^2$, $R^3$ and $R^4$ is an alkyl group, an alkoxy group, an alkylthio group, an amino group or a hydroxyl group.

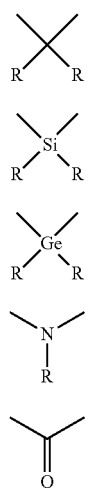

[wherein

R represents an alkyl group, an alkoxy group, an alkylthio group, an aryl group or a mono-valent heterocyclic group, and these groups may have a substituent. When there exist a plurality of R, these may be the same or different.].

[11] The compound according to [10], wherein the compound represented by the formula (5a) is a compound represented by the formula (6a):

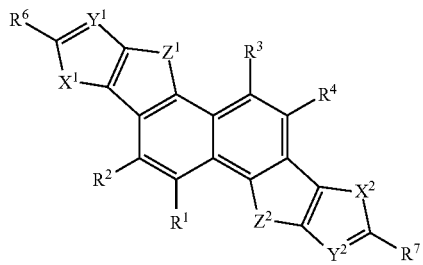

(6a)

[wherein $R^1$, $R^2$, $R^3$, $R^4$, $Z^1$ and $Z^2$ represent the same meaning as described above.

$R^6$ and $R^7$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue or an organotin residue, and these groups may have a substituent.

$X^1$ and $X^2$ represent each independently an oxygen atom, a sulfur atom or a selenium atom.

$Y^1$ and $Y^2$ represent each independently a nitrogen atom or a group represented by $-CR^5=$.

$R^5$ represents a hydrogen atom, an alkyl group, an alkoxy group, an alkylthio group, an aryl group, a mono-valent heterocyclic group or a halogen atom, and these groups may have a substituent.].

[12] An organic semiconductor material comprising the polymer compound according to any one of [1] to [9].

[13] An organic semiconductor device having a first electrode and a second electrode and having an active layer between the first electrode and the second electrode, wherein the active layer contains the polymer compound according to any one of [1] to [9].

[14] The organic semiconductor device according to [13], wherein the organic semiconductor device is any of an organic transistor, a photoelectric conversion device, an organic electroluminescent device, an organic field-effect transistor sensor and organic conductivity modulation sensor.

[15] The organic semiconductor device according to [14], wherein the organic semiconductor device is a photoelectric conversion device.

[16] A method comprising a step of contacting a compound represented by the formula (S16):

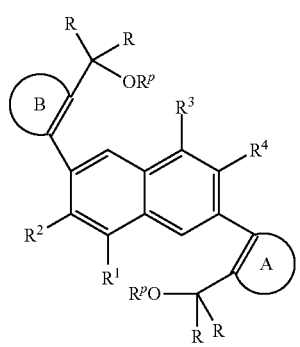

(S16)

[wherein Ring A and Ring B represent each independently a heterocyclic ring, and the heterocyclic ring may have a substituent.

$R^1$, $R^2$, $R^3$, $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent.

R represents an alkyl group, an alkoxy group, an alkylthio group, an aryl group or a mono-valent heterocyclic group, and these groups may have a substituent. When there exist a plurality of R, these may be the same or different.

$R^p$ represents an alkyl group, a silyl group or an acetyl group. When there exist a plurality of R, these may be the same or different.]

with an acid to produce a compound represented by the formula (S7):

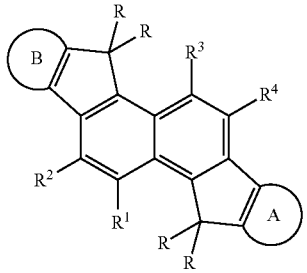

(S7)

[wherein Ring A, Ring B, $R^1$, $R^2$, $R^3$, $R^4$ and R represent the same meaning as described above.].

BRIEF EXPLANATION OF DRAWING

FIG. 1 is a schematic cross-sectional view showing one example of the photoelectric conversion device of the present invention.

MODES FOR CARRYING OUT THE INVENTION

Suitable embodiments of the present invention will be illustrated in detail below, if necessary referring to drawings.
<Polymer Compound>
(First Structural Unit)

The polymer compound of the present invention is a polymer compound comprising a structural unit represented by the formula (1) (hereinafter, referred to as "first structural unit" in some cases). The first structural unit may be singly contained in the polymer compound or two or more first structural units may be contained therein. The polymer compound of the present invention is preferably a conjugated polymer compound.

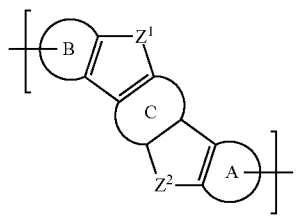

(1)

In the formula (1), Ring A and Ring B represent each independently a heterocyclic ring, and the heterocyclic ring may have a substituent. The number of carbon atoms of the heterocyclic ring is preferably 2 to 30, more preferably 2 to 14, further preferably 3 to 8. The number of carbon atoms does not include the number of carbon atoms of the substituent. The heterocyclic ring is preferably an aromatic heterocyclic ring.

The heterocyclic ring includes, for example, a furan ring, a thiophene ring, a selenophene ring, a pyrrole ring, an oxazole ring, a thiazole ring, an imidazole ring, a pyridine ring, a benzofuran ring, a benzothiophene ring, a thienothiophene ring and a 2,1,3-benzothiadiazole ring.

The substituent which the heterocyclic ring may have includes, for example, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group and an alkoxycarbonyl group.

The alkyl group may be any of a linear alkyl group or a branched alkyl group, and may also be a cycloalkyl group. The number of carbon atoms which the alkyl group has is usually 1 to 30 (in the case of branched alkyl group and cycloalkyl group, usually 3 to 30), and preferably 1 to 20 (in the case of branched alkyl group and cycloalkyl group, 3 to 20). The number of carbon atoms does not include the number of carbon atoms of the substituent.

The alkyl group includes, for example, linear alkyl groups such as a methyl group, an ethyl group, a n-propyl group, a n-butyl group, a n-hexyl group, a n-octyl group, a n-dodecyl group, a n-hexadecyl group and the like, branched alkyl groups such as an isopropyl group, an isobutyl group, a sec-butyl group, a tert-butyl group, a 2-ethylhexyl group, a 3,7-dimethyloctyl group and the like, and cycloalkyl groups such as a cyclopentyl group, a cyclohexyl group and the like.

The alkyl group may have a substituent, and the substituent includes, for example, an alkoxy group, an aryl group and a halogen atom. The alkyl group having a substituent includes, for example, a methoxyethyl group, a benzyl group, a trifluoromethyl group and a perfluorohexyl group.

The alkoxy group may be any of a linear alkoxy group or a branched alkoxy group, and may also be a cycloalkoxy group. The number of carbon atoms which the alkoxy group has is usually 1 to 30 (in the case of branched alkoxy group and cycloalkoxy group, usually 3 to 30), and preferably 1 to 20 (in the case of branched alkoxy group and cycloalkoxy group, 3 to 20). The number of carbon atoms does not include the number of carbon atoms of the substituent.

The alkoxy group includes, for example, linear alkoxy groups such as a methoxy group, an ethoxy group, a n-propyloxy group, a n-butyloxy group, a n-hexyloxy group, a n-octyloxy group, a n-dodecyloxy group, a n-hexadecyloxy group and the like; branched alkoxy groups such as an isopropyloxy group, an isobutyloxy group, a sec-butyloxy group, a tert-butyloxy group, a 2-ethylhexyloxy group, a 3,7-dimethyloctyloxy group and the like; and cycloalkoxy groups such as a cyclopentyloxy group, a cyclohexyloxy group and the like.

The alkoxy group may have a substituent, and the substituent includes, for example, an alkoxy group, an aryl group and a halogen atom.

The alkylthio group may be any of a linear alkylthio group or a branched alkylthio group, and may also be a cycloalkylthio group. The number of carbon atoms which the alkylthio group has is usually 1 to 30 (in the case of branched alkylthio group and cycloalkylthio group, usually 3 to 30), and preferably 1 to 20 (in the case of branched alkylthio group and cycloalkylthio group, 3 to 20). The number of carbon atoms does not include the number of carbon atoms of the substituent.

The alkylthio group includes, for example, linear alkylthio groups such as a methylthio group, an ethylthio group, a n-propylthio group, a n-butylthio group, a n-hexylthio group, a n-octylthio group, a n-dodecylthio group, a n-hexadecylthio group and the like; branched alkylthio groups such as an isopropylthio group, an isobutylthio group, a sec-butylthio group, a tert-butylthio group, a 2-ethylhexylthio group, a 3,7-dimethyloctylthio group and the like; and cycloalkylthio groups such as a cyclopentylthio group, a cyclohexylthio group and the like.

The alkylthio group may have a substituent, and the substituent includes, for example, an alkoxy group, an aryl group and a halogen atom.

The aryl group is an atomic group remaining after removing from an aromatic hydrocarbon which may have a substituent one hydrogen atom bonding directly to a carbon atom constituting the ring, and includes groups having a condensed ring, and groups obtained by directly bonding two or more selected from the group consisting of independent benzene rings and condensed rings. The number of carbon atoms which the aryl group has is usually 6 to 30, preferably 6 to 20. The number of carbon atoms does not include the number of carbon atoms of the substituent.

The aryl group includes, for example, a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group and a 4-phenylphenyl group.

The aryl group may have a substituent, and the substituent includes, for example, an alkyl group, an alkoxy group, an alkylthio group, a mono-valent a heterocyclic group and a halogen atom. The aryl group having a substituent includes, for example, a-hexadecylphenyl group, a 3,5-dimethoxyphenyl group and a pentafluorophenyl group. When the aryl group has a substituent, the substituent is preferably an alkyl group.

The mono-valent heterocyclic group is an atomic group remaining after removing from a heterocyclic compound which may have a substituent one hydrogen atom bonding directly to a carbon atom or a hetero atom constituting the ring, and includes groups having a condensed ring and groups obtained by directly bonding two or more selected from the group consisting of independent heterocyclic rings and condensed rings. The number of carbon atoms which the mono-valent heterocyclic group has is usually 2 to 30, preferably 3 to 20. The number of carbon atoms does not include the number of carbon atoms of the substituent. The mono-valent heterocyclic group is preferably a mono-valent aromatic heterocyclic group.

The mono-valent heterocyclic group includes, for example, a 2-furyl group, a 3-furyl group, a 2-thienyl group, a 3-thienyl group, a 2-pyrrolyl group, a 3-pyrrolyl group, a 2-oxazolyl group, a 2-thiazolyl group, a 2-imidazolyl group, a 2-pyridyl group, a 3-pyridyl group, a 4-pyridyl group, a 2-benzofuryl group, a 2-benzothienyl group, a 2-thienothienyl group and a 4-(2,1,3-benzothiadiazolyl) group.

The mono-valent heterocyclic group may have a substituent, and the substituent includes, for example, an alkyl group, an alkoxy group, an alkylthio group, an aryl group and a halogen atom. The mono-valent heterocyclic group having a substituent includes, for example, a 5-octyl-2-thienyl group and a 5-phenyl-2-furyl group. When the mono-valent heterocyclic group has a substituent, the substituent is preferably an alkyl group.

The halogen atom includes, for example, a fluorine atom, a chlorine atom, a bromine atom and an iodine atom.

The silyl group may have a substituent. The substituent which the silyl group may have includes, for example, an alkyl group and an aryl group. The silyl group having a substituent includes, for example, a trimethylsilyl group, a triethylsilyl group, a triisopropylsilyl group, a tert-butyldimethylsilyl group, a phenylsilyl group and a triphenylsilyl group.

The number of carbon atoms of the silyl group is usually 0 to 90, preferably 3 to 90.

The amino group may have a substituent. The substituent which the amino group may have includes, for example, an alkyl group and an aryl group. The amino group having a substituent includes, for example, a dimethylamino group, a diethylamino group, a diisopropylamino group and a diphenylamino group. The number of carbon atoms of the amino group is usually 0 to 90, preferably 3 to 90.

The alkenyl group may be a linear alkenyl group or a branched alkenyl group, and may also be a cycloalkenyl group. The number of carbon atoms which the alkenyl group has is usually 2 to 30 (in the case of branched alkenyl group and cycloalkenyl group, usually 3 to 30), and preferably 2 to 20 (in the case of branched alkenyl group and cycloalkenyl group, 3 to 20). The number of carbon atoms does not include the number of carbon atoms of the substituent.

The alkenyl group includes, for example, a vinyl group, a 1-propenyl group, a 2-propenyl group, a 1-hexenyl group, a 1-dodecenyl group, a 1-hexadecenyl group and a 1-cyclohexenyl group.

The alkenyl group may have a substituent, and the substituent includes, for example, an aryl group, a halogen atom and a silyl group.

The alkynyl group may be a linear alkynyl group or a branched alkynyl group. The number of carbon atoms which the alkynyl group has is usually 2 to 30 (in the case of branched alkynyl group, usually 4 to 30), and preferably 2 to 20 (in the case of branched alkynyl group, 4 to 20). The number of carbon atoms does not include the number of carbon atoms of the substituent.

The alkynyl group includes, for example, an ethynyl group, a 1-propynyl group, a 1-hexynyl group, a 1-dodecynyl group and a 1-hexadecynyl group.

The alkynyl group may have a substituent, and the substituent includes, for example, an aryl group, a halogen atom and a silyl group.

The alkylcarbonyl group includes, for example, groups obtained by bonding the above-described alkyl group with a carbonyl group.

The alkylcarbonyl group includes, for example, linear alkylcarbonyl groups such as an acetyl group, a n-propanoyl group, a n-butanoyl group, a n-hexanoyl group, a n-octanoyl group, a n-dodecanoyl group, a n-hexadecanoyl group and the like, branched alkylcarbonyl groups such as an isobutanoyl group, a sec-butanoyl group, a tert-butanoyl group, a 2-ethylhexanoyl group and the like, and cycloalkylcarbonyl groups such as a cyclopentylcarbonyl group, a cyclohexylcarbonyl group and the like.

The number of carbon atoms of the alkylcarbonyl group is usually 2 to 30.

The alkoxycarbonyl group includes, for example, groups obtained by bonding the above-described alkoxy group with a carbonyl group.

The alkoxycarbonyl group includes, for example, linear alkoxycarbonyl groups such as a methoxycarbonyl group, an ethoxycarbonyl group, a n-propyloxycarbonyl group, a n-butoxycarbonyl group, a n-hexyloxycarbonyl group, a n-octyloxycarbonyl group, a n-dodecyloxycarbonyl group, a n-hexadecyloxycarbonyl group and the like, branched alkoxycarbonyl groups such as an isopropyloxycarbonyl group, an isobutyloxycarbonyl group, a sec-butyloxycarbonyl group, a tert-butyloxycarbonyl group, a 2-ethylhexyloxycarbonyl group and the like, and cycloalkoxycarbonyl groups such as a cyclopentyloxycarbonyl group, a cyclohexyloxycarbonyl group and the like.

The number of carbon atoms of the alkoxycarbonyl group is usually 2 to 30.

It is preferable that Ring A and Ring B are the same heterocyclic ring since then synthesis of the polymer compound of the present invention is easy.

It is preferable that Ring A and Ring B are constituted of a 5-membered and/or 6-membered heterocyclic ring, more preferably constituted only of a 5-membered heterocyclic ring since then an organic film solar battery produced by using the polymer compound of the present invention is more excellent in ff (fill factor).

In the formula (1), Ring C represents an aromatic hydrocarbon ring obtained by condensing two or more benzene rings, and the aromatic hydrocarbon ring may have a substituent.

The number of carbon atoms of the aromatic hydrocarbon ring is preferably 10 to 30, more preferably 10 to 24, further preferably 10 to 18. The number of carbon atoms does not include the number of carbon atoms of the substituent.

The aromatic hydrocarbon ring includes, for example, a naphthalene ring, an anthracene ring, a pyrene ring and a fluorene ring.

The substituent which the aromatic hydrocarbon ring may have includes, for example, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and the definition and specific examples of these substituents are the same as the definition and specific examples of the alkyl group, the alkoxy group, the alkylthio group, the aryl group, the mono-valent heterocyclic group, the halogen atom, the silyl group, amino group, the alkenyl group, the alkynyl group, the alkylcarbonyl group and the alkoxycarbonyl group as the above-described substituent which the heterocyclic ring may have.

Ring C has preferably an alkyl group, an alkoxy group, an alkylthio group, an amino group or a hydroxyl group, more preferably has an alkyl group or an alkoxy group, further preferably has an alkoxy group.

Ring C preferably has 1 to 4 alkyl groups, alkoxy groups, alkylthio groups, amino groups or hydroxyl groups, more preferably has 1 to 2 alkyl groups, alkoxy groups, alkylthio groups, amino groups or hydroxyl groups.

In the formula (1), $Z^1$ and $Z^2$ represent each independently a group represented by the formula (Z-1), a group represented by the formula (Z-2), a group represented by the formula (Z-3), a group represented by the formula (Z-4) or a group represented by the formula (Z-5).

(Z-1)

(Z-2)

(Z-3)

(Z-4)

(Z-5)

It is preferable that $Z^1$ and $Z^2$ represent the same group since then synthesis of the polymer compound of the present invention is easy.

$Z^1$ and $Z^2$ are preferably a group represented by the formula (Z-1), the formula (Z-2) or the formula (Z-3), more preferably a group represented by the formula (Z-1) or the formula (Z-2), further preferably a group represented by the formula (Z-1) since then an organic film solar battery produced by using the polymer compound of the present invention is more excellent in ff (fill factor).

In the formulae (Z-1) to (Z-5), R represents an alkyl group, an alkoxy group, an alkylthio group, an aryl group or a mono-valent heterocyclic group, and these groups may have a substituent.

The definition and specific examples of the alkyl group, the alkoxy group, the alkylthio group, the aryl group and the mono-valent heterocyclic group are the same as the definition and specific examples of the alkyl group, the alkoxy group, the alkylthio group, the aryl group and the mono-valent heterocyclic group as the above-described substituent which the heterocyclic ring may have.

R is preferably an alkyl group or an aryl group since then an organic film solar battery produced by using the polymer compound of the present invention is more excellent in ff (fill factor).

R is preferably an alkyl group or an aryl group, more preferably an alkyl group, further preferably a linear alkyl group since then synthesis of the polymer compound of the present invention is easy.

The structural unit represented by the formula (1) is preferably a structural unit represented by the formula (2a) since then synthesis of the polymer compound of the present invention is easy.

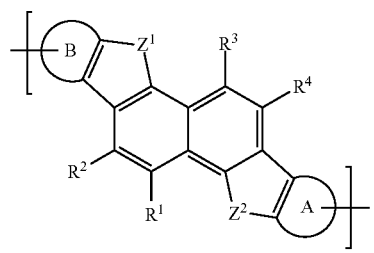

(2a)

In the formula (2a), $R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent. Here, at least one selected from the group consisting of $R^1$, $R^2$, $R^3$ and $R^4$ is an alkyl group, an alkoxy group, an alkylthio group, an amino group or a hydroxyl group.

The definition and specific examples of the alkyl group, the alkoxy group, the alkylthio group, the aryl group, the mono-valent heterocyclic group, the halogen atom, the silyl group, the amino group, the alkenyl group, the alkynyl group, the alkylcarbonyl group and the alkoxycarbonyl group are the same as the definition and specific examples of the alkyl group, the alkoxy group, the alkylthio group, the aryl group, the mono-valent heterocyclic group, the halogen atom, the silyl group, the amino group, the alkenyl group, the alkynyl group, the alkylcarbonyl group and the alkoxycarbonyl group as the above-described substituent which the heterocyclic ring may have.

The structural unit represented by the formula (2a) is preferably a structural unit represented by the formula (3a) since then synthesis of the polymer compound of the present invention is easy.

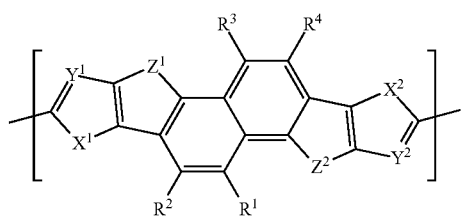
(3a)

In the formula (3a), $X^1$ and $X^2$ represent each independently an oxygen atom, a sulfur atom or a selenium atom. $Y^1$ and $Y^2$ represent each independently a nitrogen atom or a group represented by $-CR^5=$. $R^5$ represents a hydrogen atom, an alkyl group, an alkoxy group, an alkylthio group, an aryl group, a mono-valent heterocyclic group or a halogen atom.

The definition and specific examples of the alkyl group, the alkoxy group, the alkylthio group, the aryl group, the mono-valent heterocyclic group and the halogen atom are the same as the definition and specific examples of the alkyl group, the alkoxy group, the alkylthio group, the aryl group, the mono-valent heterocyclic group and the halogen atom as the above-described substituent which the heterocyclic ring may have.

The structural unit represented by the formula (1) is also preferably a structural unit represented by the formula (2b) or a structural unit represented by the formula (2c) since then synthesis of the polymer compound of the present invention is easy.

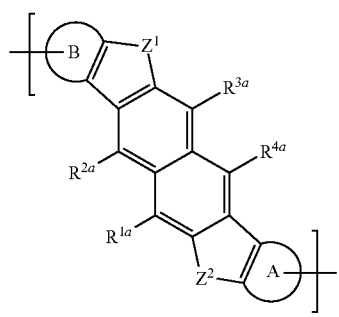
(2b)

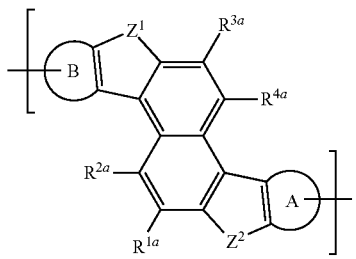
(2c)

In the formulae (2b) and (2c), $R^{1a}$, $R^{2a}$, $R^{3a}$ and $R^{4a}$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent. Here, at least one selected from the group consisting of $R^{1a}$, $R^{2a}$, $R^{3a}$ and $R^{4a}$ in the formula (2b) is an alkyl group, an alkoxy group, an alkylthio group, an amino group or a hydroxyl group, and at least one selected from the group consisting of $R^{1a}$, $R^{2a}$, $R^{3a}$ and $R^{4a}$ in the formula (2c) is an alkyl group, an alkoxy group, an alkylthio group, an amino group or a hydroxyl group.

The definition and specific examples of the alkyl group, the alkoxy group, the alkylthio group, the aryl group, the mono-valent heterocyclic group, the halogen atom, the silyl group, the amino group, the alkenyl group, the alkynyl group, the alkylcarbonyl group and the alkoxycarbonyl group are the same as the definition and specific examples of the alkyl group, the alkoxy group, the alkylthio group, the aryl group, the mono-valent heterocyclic group, the halogen atom, the silyl group, the amino group, the alkenyl group, the alkynyl group, the alkylcarbonyl group and the alkoxycarbonyl group as the above-described substituent which the heterocyclic ring may have.

$X^1$ and $X^2$ are preferably an oxygen atom or a sulfur atom, more preferably a sulfur atom since then synthesis of the polymer compound of the present invention is easy.

$Y^1$ and $Y^2$ are preferably $-CR^5=$, more preferably $-CH=$ since then synthesis of the polymer compound of the present invention is easy.

The structural unit represented by the formula (1) (may also be a structural unit represented by the formulae (2a) to (2c), or a structural unit represented by the formula (3a)) includes, for example, structural units represented by the formulae (1-1) to (1-38).

The structural unit represented by the formula (1) is preferably a structural unit represented by the formulae (1-1) to (1-5), (1-7) to (1-10), (1-29), (1-32), (1-33) and (1-35) to (1-38), more preferably a structural unit represented by the formulae (1-2) to (1-5), (1-7) to (1-9), (1-29), (1-33) and (1-35) to (1-38), further preferably a structural unit represented by the formulae (1-4) to (1-5), (1-8), (1-9), (1-33), (1-36) and (1-37) since then an organic film solar battery produced by using the polymer compound of the present invention is more excellent in ff (fill factor).

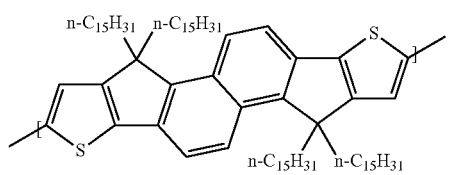
(1-1)
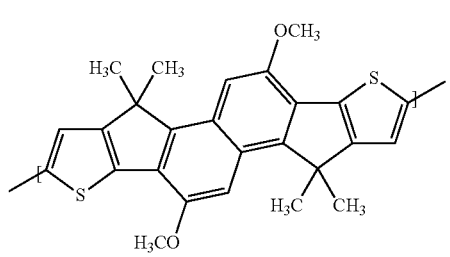
(1-2)
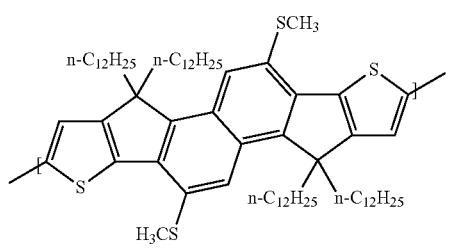
(1-3)
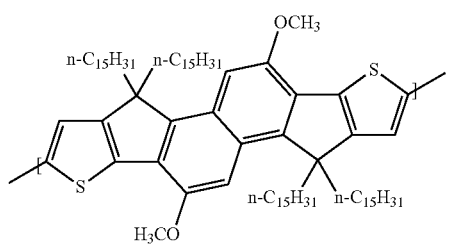
(1-4)
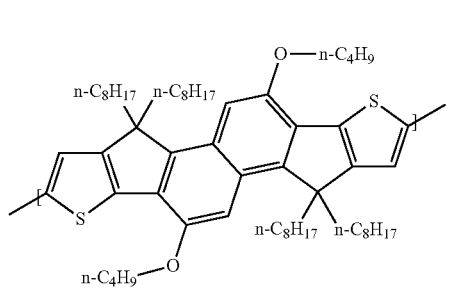
(1-5)
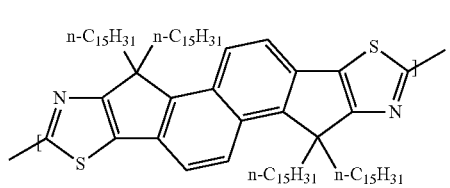
(1-6)
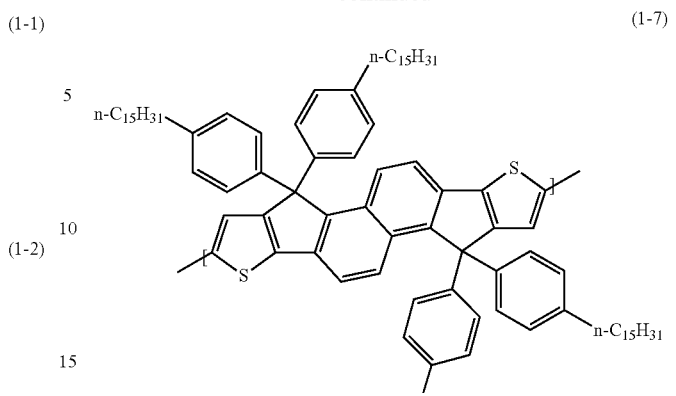
(1-7)
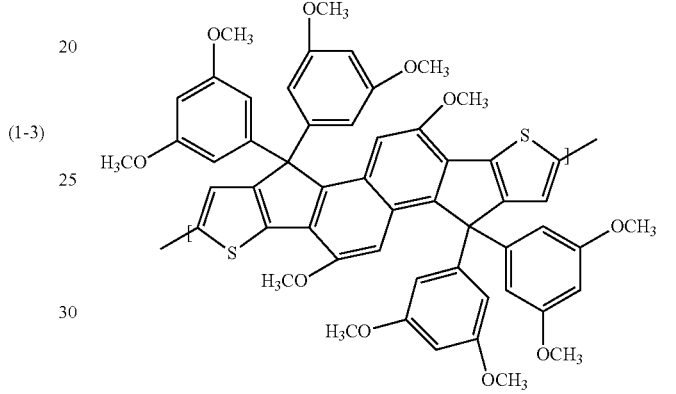
(1-8)
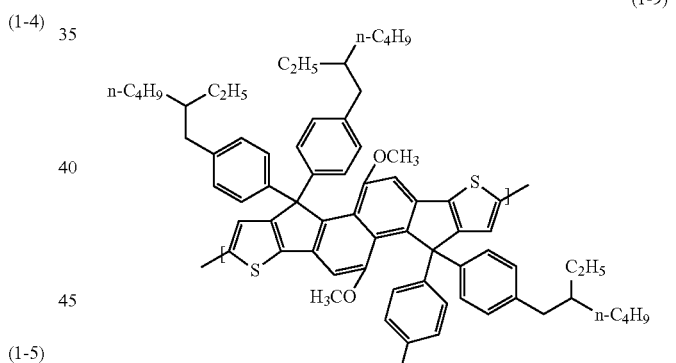
(1-9)
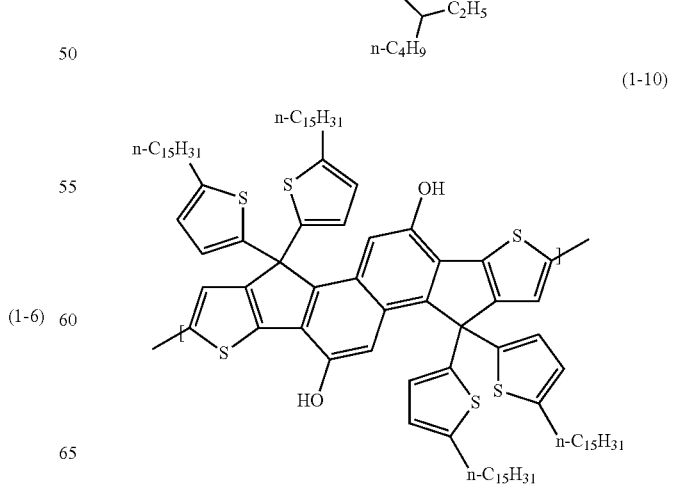
(1-10)

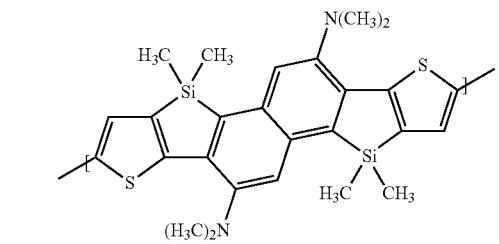 (1-11)
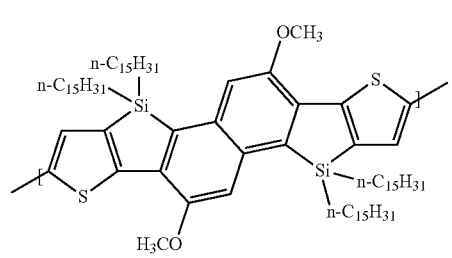 (1-12)
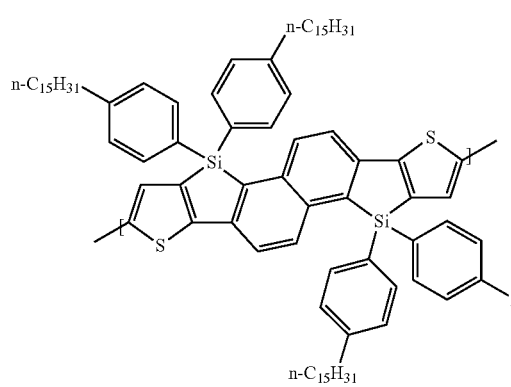 (1-13)
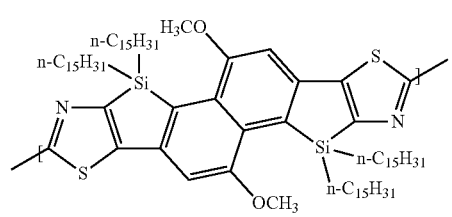 (1-14)
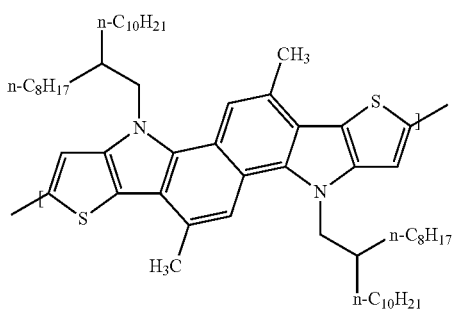 (1-15)
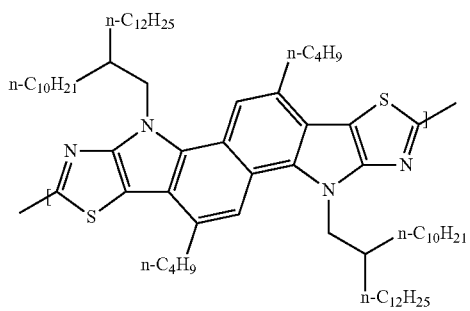 (1-16)
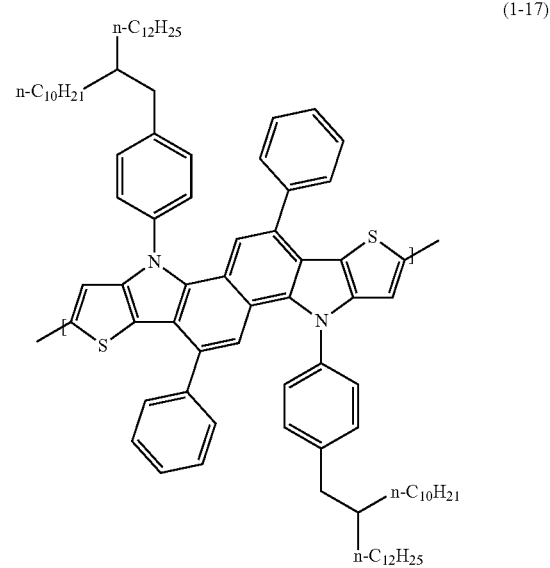 (1-17)
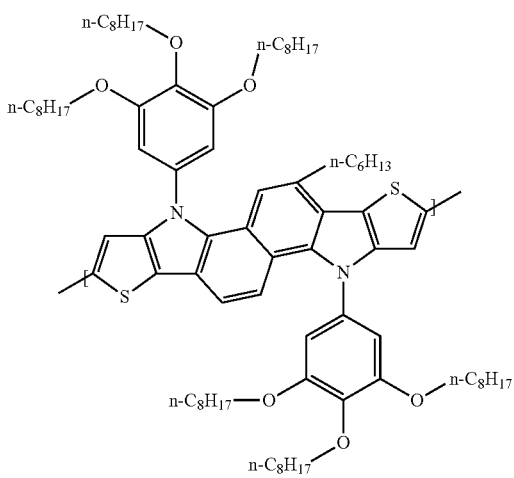 (1-18)
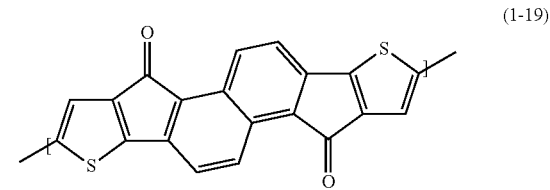 (1-19)

(1-20) 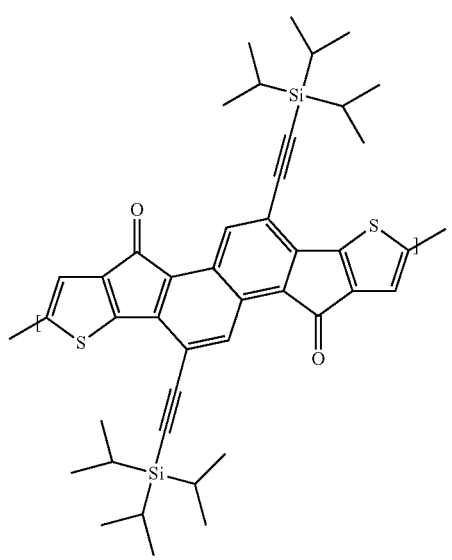
(1-21) 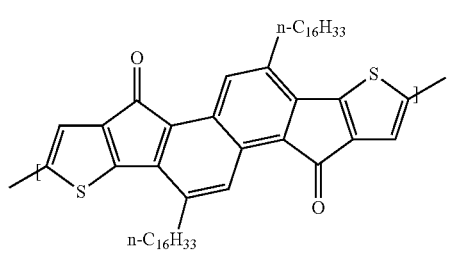
(1-22) 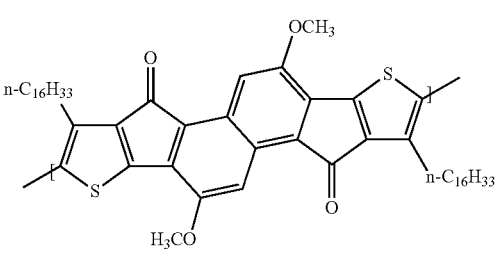
(1-23) 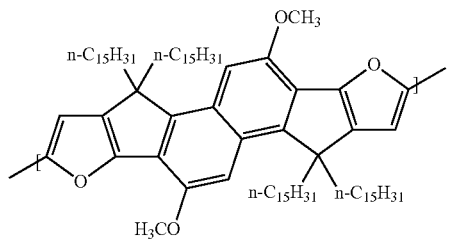
(1-24) 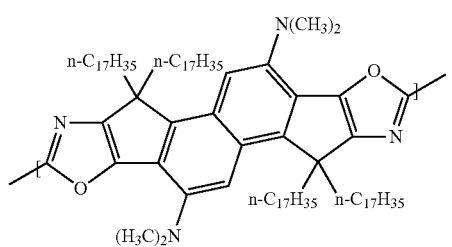
(1-25) 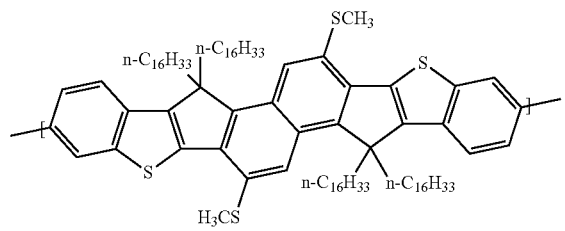
(1-26) 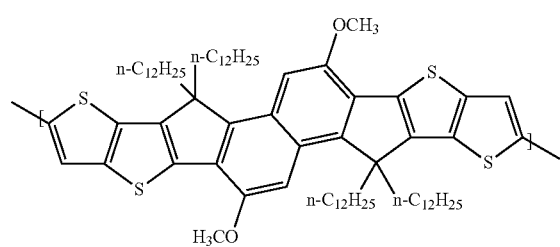
(1-27) 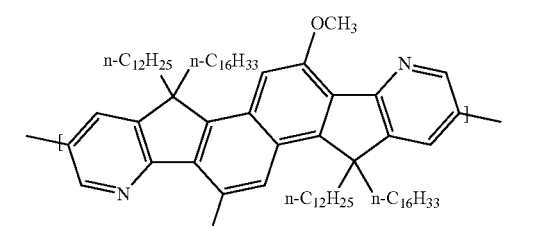
(1-28) 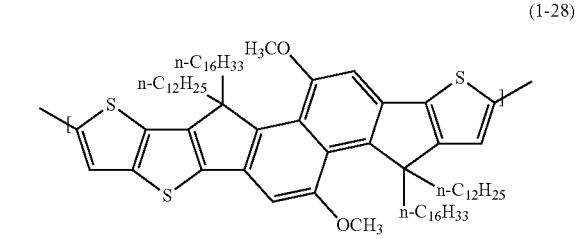
(1-29) 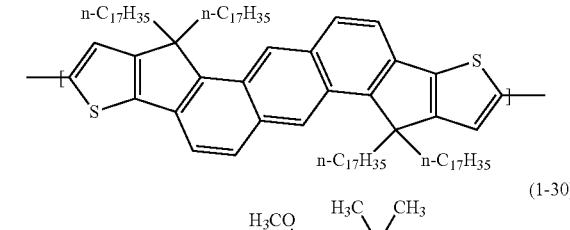
(1-30) 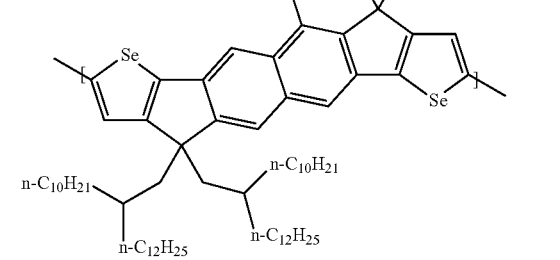

-continued (1-31)
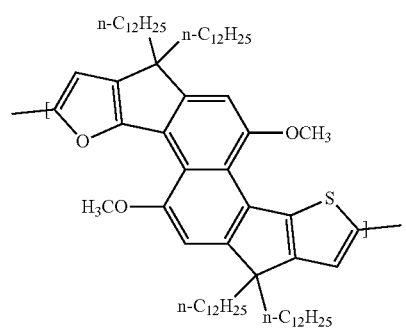

(1-32)
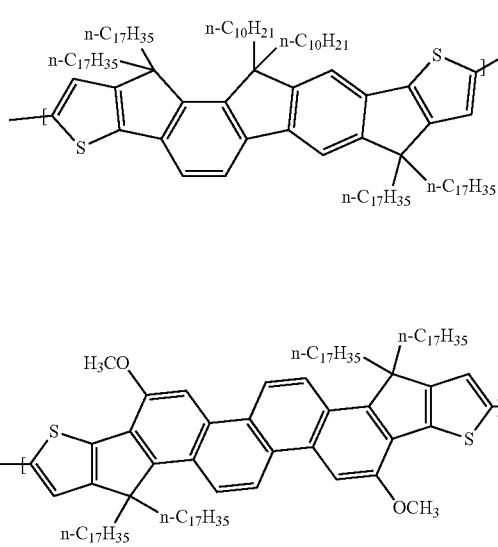

(1-33)
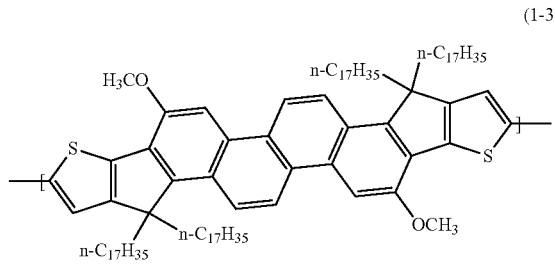

(1-34)
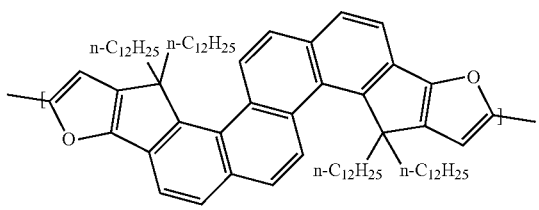

(1-35)
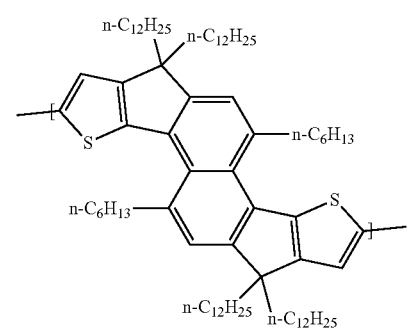

-continued (1-36)
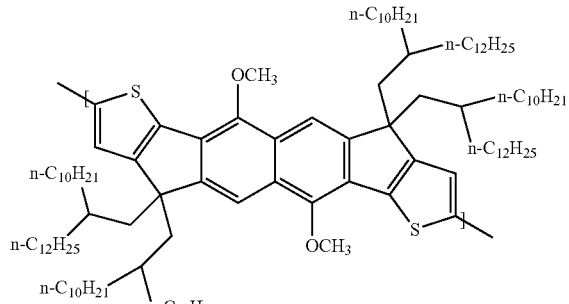

(1-37)
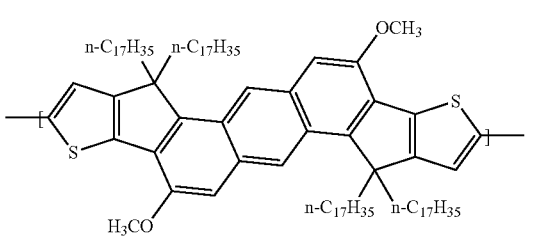

(1-38)
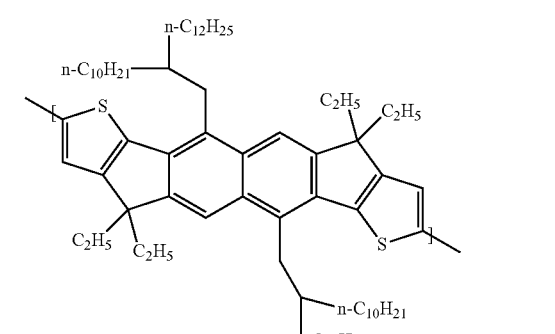

(Second Structural Unit)

It is preferable that the polymer compound of the present invention further contains a structural unit represented by the formula (4) (different from the structural unit represented by the formula (1)) (hereinafter, referred to as "second structural unit" in some cases), in addition to the structural unit represented by the formula (1).

 (4)

In the formula (4), Ar represents an arylene group or a di-valent heterocyclic group, and these groups may have a substituent.

When the polymer compound of the present invention contains a second structural unit, it is preferable that the structural unit represented by the formula (1) (may also be a structural unit represented the formulae (2a) to formula (2c), or a structural unit represented by the formula (3a)) and the structural unit represented by the formula (4) are conjugated.

In the present specification, conjugation denote a condition in which an unsaturated bond, a single bond and an unsaturated bond are chained in this order, two π bonds on the π orbital are adjacent and respective π electrons are disposed parallel, and π electrons are not delocalized on an unsaturated bond but π electrons are spread onto an adjacent single bond to attain delocalization of π electrons. Here, the unsaturated bond means a double bond and a triple bond.

The arylene group is an atomic group remaining after removing from an aromatic hydrocarbon which may have a substituent two hydrogen atoms directly bonding to carbon atoms constituting the ring, and includes groups having a condensed ring, groups obtained by directly bonding two or more selected from the group consisting of independent benzene rings and condensed rings, and groups obtained by bonding two or more selected from the group consisting of independent benzene rings and condensed rings via vinylene and the like. The number of carbon atoms which the arylene group has is usually 6 to 60, preferably 6 to 20. The number of carbon atoms does not include the number of carbon atoms of the substituent.

The arylene group may have a substituent, and the substituent includes, for example, an alkyl group, an alkoxy group, an alkylthio group, a mono-valent heterocyclic group and a halogen atom. The definition and specific examples of these substituents are the same as the definition and specific examples of the alkyl group, the alkoxy group, the alkylthio group, the mono-valent heterocyclic group and the halogen atom as the above-described substituent which the heterocyclic ring may have.

The arylene group includes, for example, arylene groups represented by the following formulae 1 to 12.

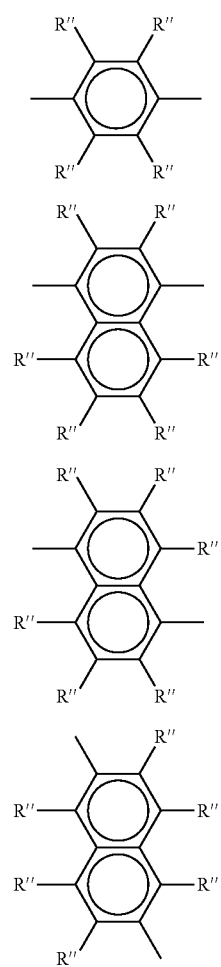

-continued

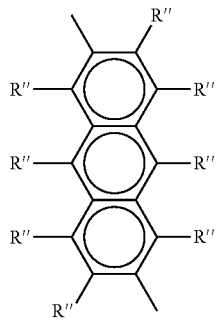

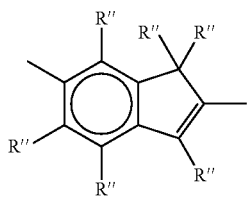

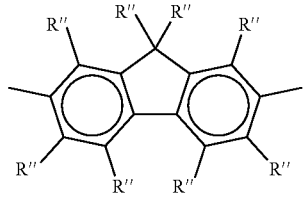

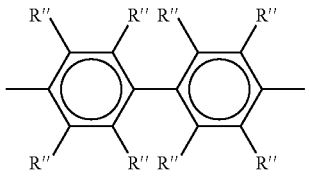

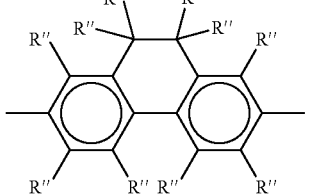

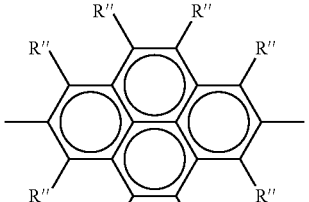

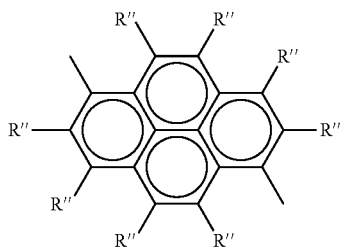

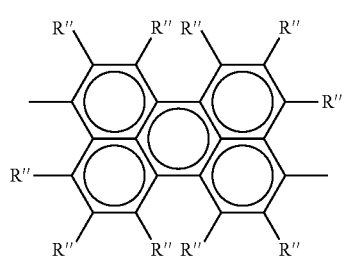

12

In the formulae 1 to 12, R" represents a hydrogen atom, an alkyl group, an alkoxy group, an alkylthio group, an aryl group, a mono-valent heterocyclic group or a halogen atom. A plurality of R" may be the same or different.

The definition and specific examples of the alkyl group, the alkoxy group, the alkylthio group, the aryl group, the mono-valent heterocyclic group and the halogen atom are the same as the definition and specific examples of the alkyl group, the alkoxy group, the alkylthio group, the aryl group, the mono-valent heterocyclic group and the halogen atom as the above-described substituent which the heterocyclic ring may have.

The di-valent heterocyclic group is an atomic group remaining after moving from a heterocyclic compound which may have a substituent two hydrogen atoms directly bonding to carbon atoms or hetero atoms constituting the ring, and include groups having a condensed ring and groups obtained by directly bonding two or more selected from the group consisting of independent heterocyclic rings and condensed rings. The number of carbon atoms which the di-valent heterocyclic group has is usually 2 to 30, preferably 3 to 20. The number of carbon atoms does not include the number of carbon atoms of the substituent. The di-valent heterocyclic group is preferably a di-valent aromatic heterocyclic group.

The di-valent heterocyclic group may have a substituent, and the substituent includes, for example, an alkyl group, an alkoxy group, an alkylthio group, an aryl group and a halogen atom. The definition and specific examples of these substituents are the same as the definition and specific examples of the alkyl group, the alkoxy group, the alkylthio group, the aryl group and the halogen atom as the above-described substituent which the heterocyclic ring may have.

The di-valent heterocyclic group includes, for example, di-valent heterocyclic groups represented by the following formulae 13 to 64.

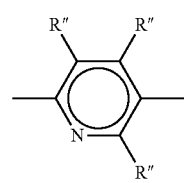

13

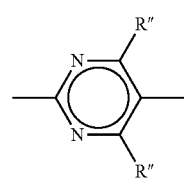

14

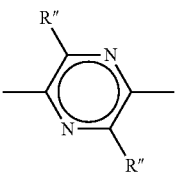

15

16

17

18

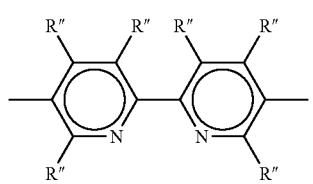

19

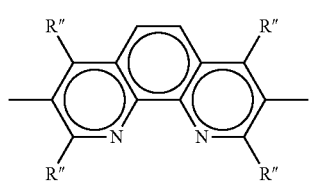

20

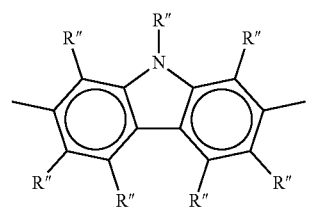

21

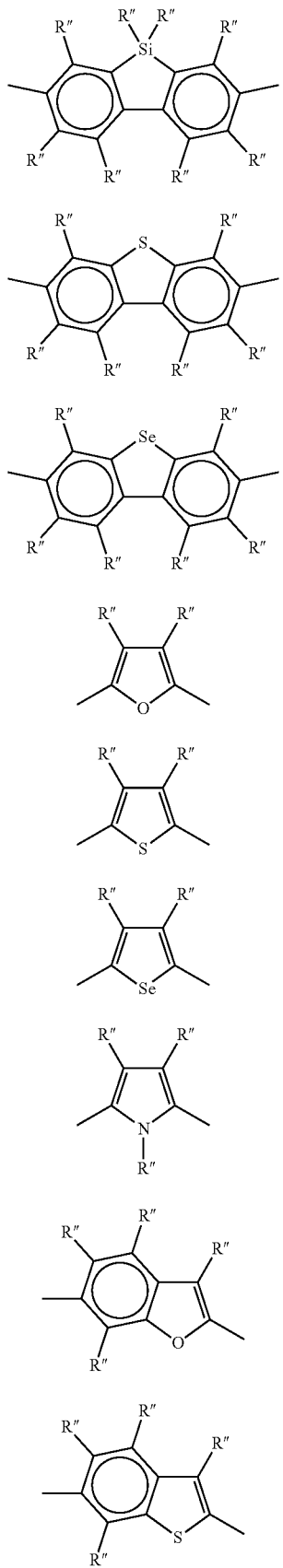
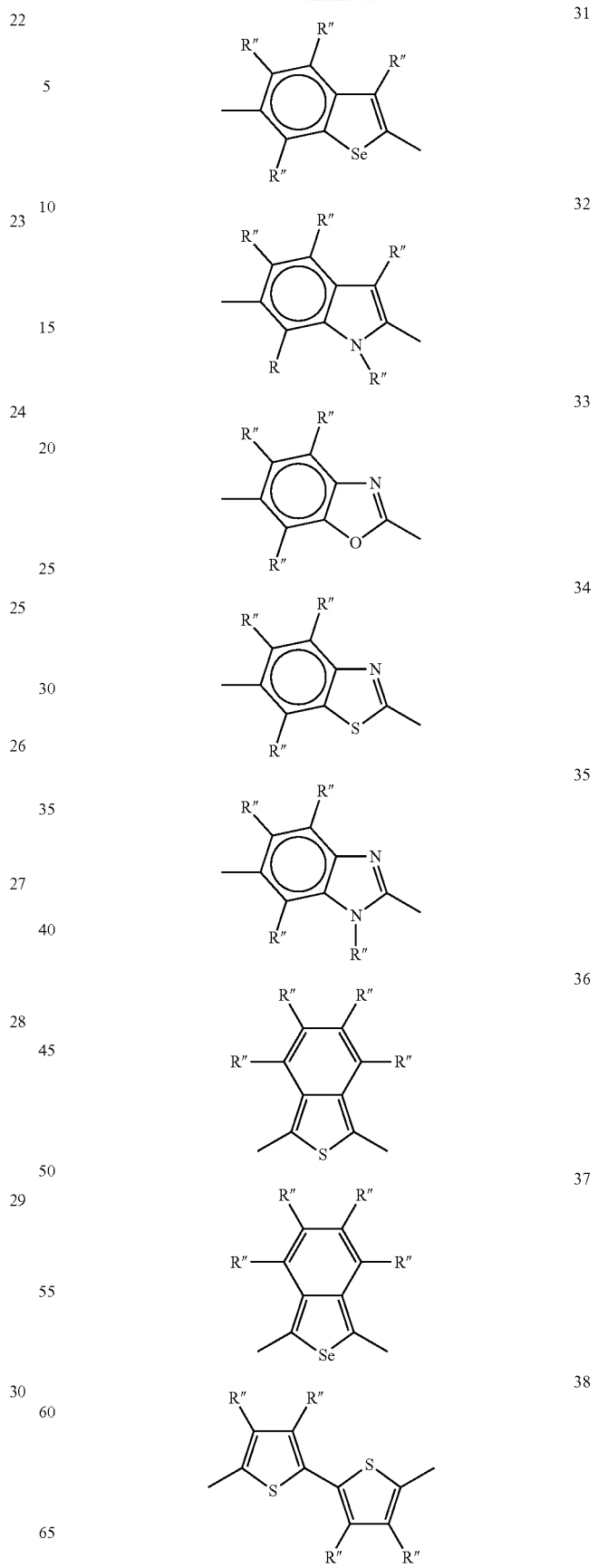

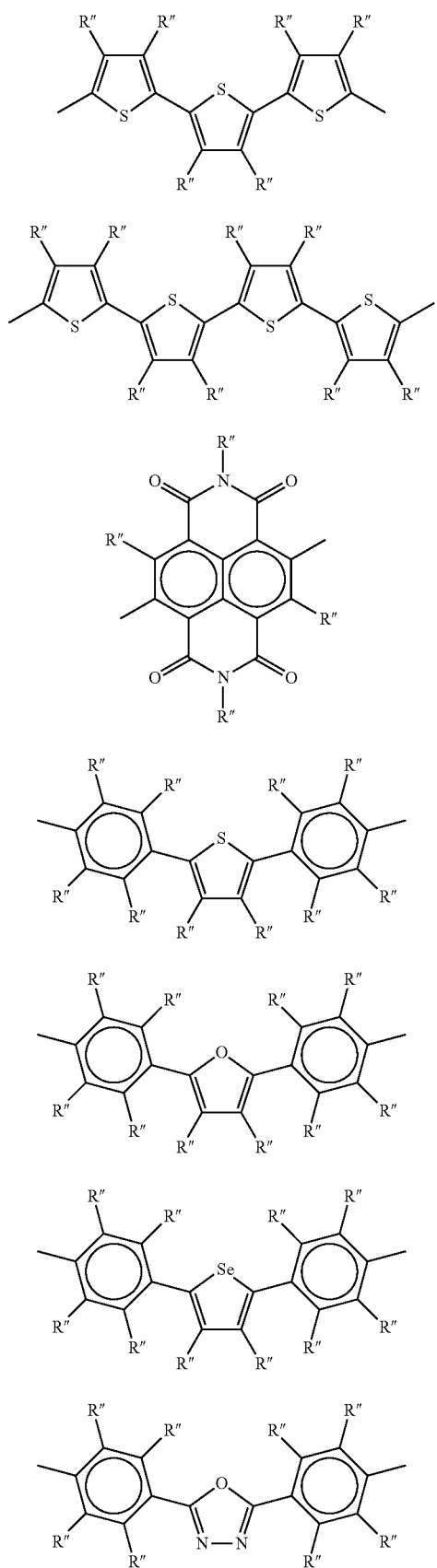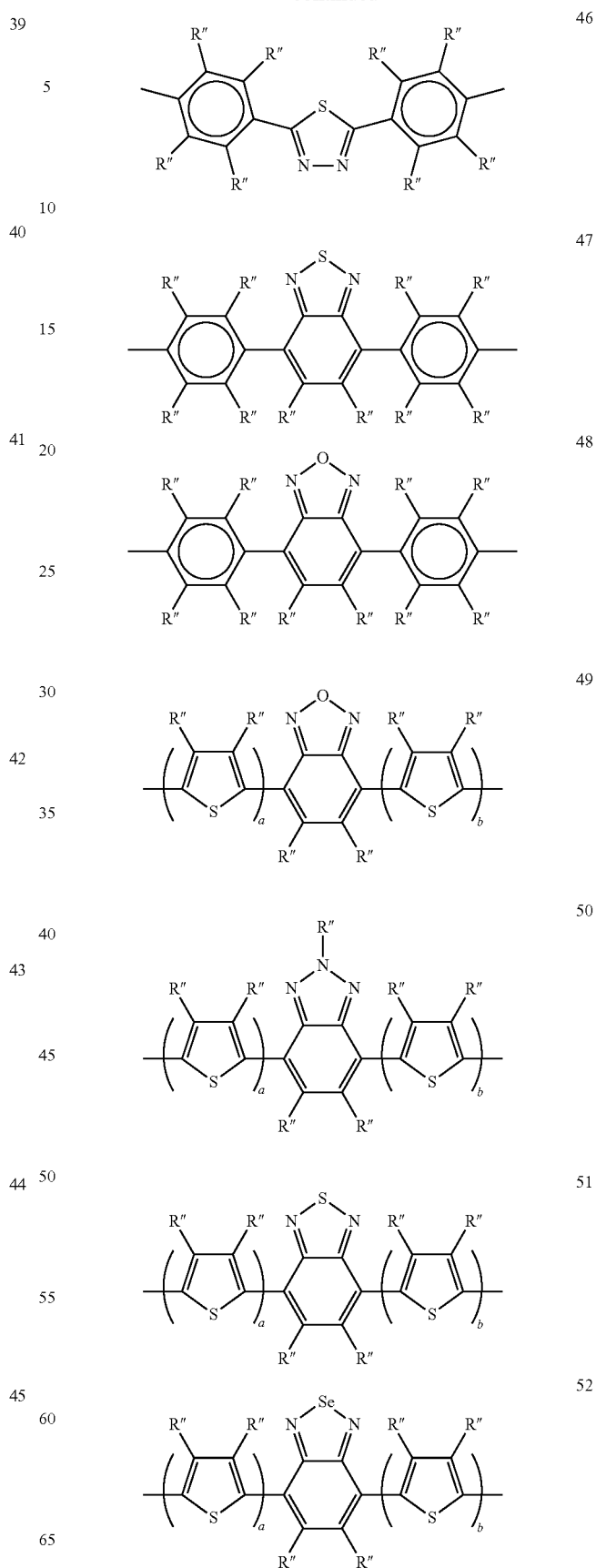

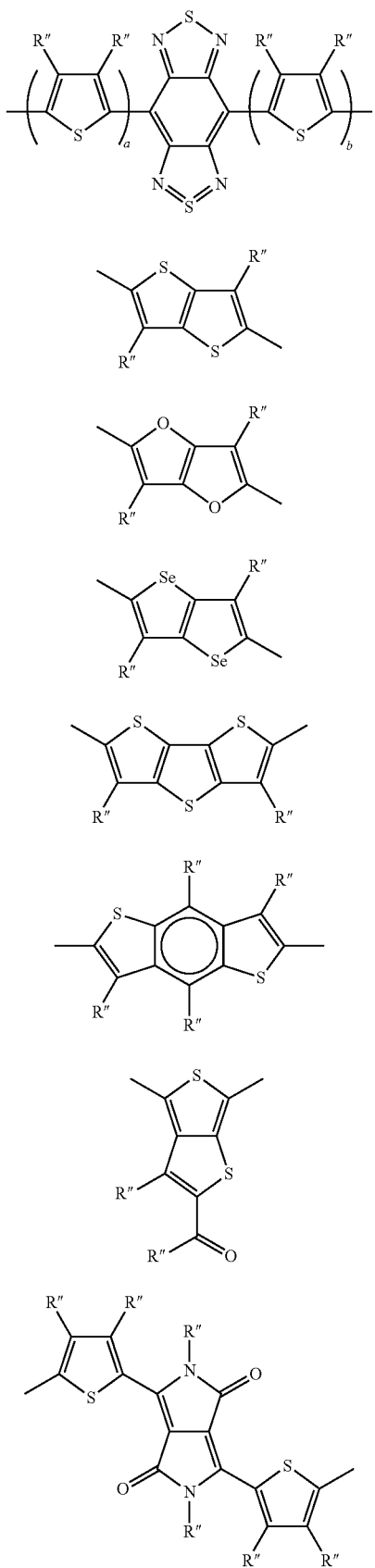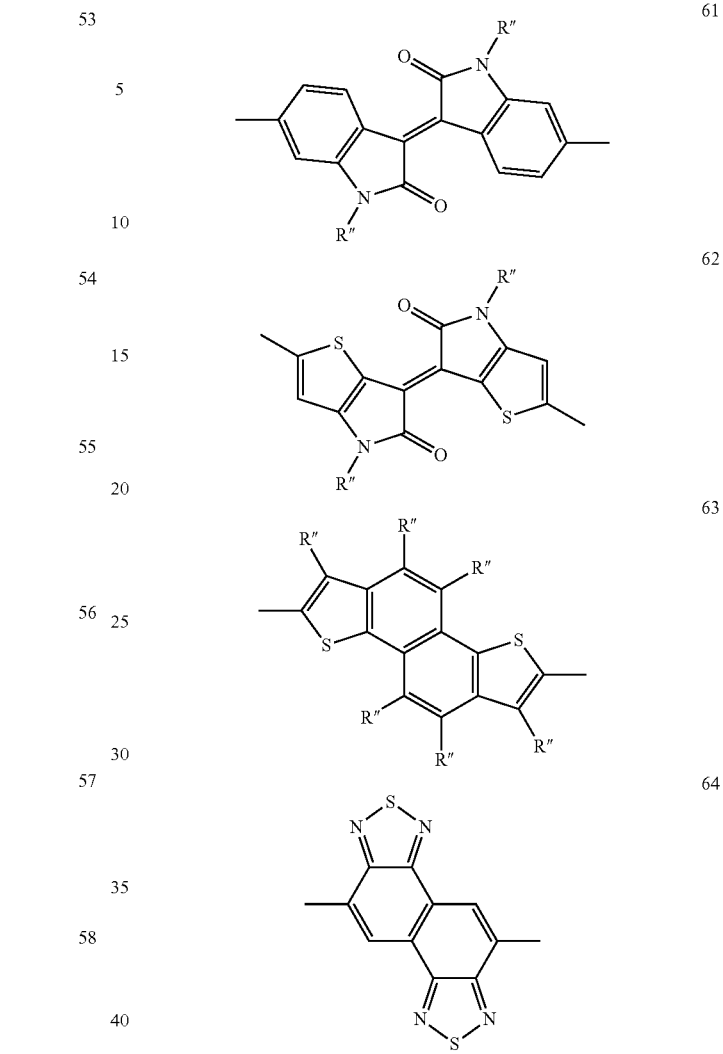

In the formulae 13 to 64, R" represents the same meaning as described above. a and b represent each independently the repetition number, usually an integer of 0 to 5, preferably an integer of 0 to 3, more preferably an integer of C to 1.

The second structural unit is preferably a di-valent heterocyclic group, more preferably a di-valent heterocyclic group represented by the formulae 49 to 53, the formulae 59 to 62 and the formula 64, further preferably a di-valent heterocyclic group represented by the formula 51 and the formula 64 since then an organic film solar battery produced by using the polymer compound of the present invention is more excellent in ff (fill factor).

The polystyrene-equivalent number-average molecular weight (Mn) of the polymer compound of the present invention measured by gel permeation chromatography (hereinafter, referred to as "GPC") is usually $1 \times 10^3$ to $1 \times 10^7$. The number-average molecular weight is preferably $3 \times 10^3$ or more from the standpoint of forming an excellent film. The number-average molecular weight is preferably $1 \times 10^6$ or less from the standpoint of enhancing solubility in a solvent and making film formation easy.

The polymer compound of the present invention has high solubility in a solvent (preferably, organic solvent), and specifically, solubility by which a solution containing the polymer compound of the present invention in an amount of 0.1 wt % or more can be prepared is preferable, and solubility by which a solution containing the polymer compound in an amount of 0.4 wt % or more can be prepared is more preferable.

Regarding the content of a structural unit represented by the formula (1) in the polymer compound of the present invention, it may be permissible that at least one unit is contained in the polymer compound, it is preferable that three or more units are contained in the polymer compound, it is more preferable that five or more units are contained in the polymer compound.

The polymer compound of the present invention may be a homopolymer or a copolymer.

The polymer compound of the present invention may be any kind of copolymer, and, for example, may be any of a block copolymer, a random copolymer, an alternative copolymer or a graft copolymer. The polymer compound of the present invention is preferably a copolymer composed of a structural unit represented by the formula (1) and a structural unit represented by the formula (4), more preferably an alternative copolymer of a structural unit represented by the formula (1) with a structural unit represented by the formula (4) since then an organic film solar battery produced by using the polymer compound of the present invention is more excellent in ff (fill factor).

When a group which is active on the polymerization reaction remains at the molecular chain end of the polymer compound of the present invention, there is a possibility that ff (fill factor) of an organic film solar battery produced by using the polymer compound lowers. Therefore, it is preferable that the molecular chain end is a stable group such as an aryl group, a mono-valent aromatic heterocyclic group or the like.

<Method of Producing Polymer Compound>

The method of producing the polymer compound of the present invention will be illustrated.

Though the polymer compound of the present invention may be produced by any method, for example, a compound represented by the formula: $^{11}$-A$^{11}$-X$^{12}$ and a compound represented by the formula: X$^{13}$-A$^{12}$-X$^{14}$ are, if necessary dissolved in an organic solvent, and if necessary a base is added, and the polymer compound can be synthesized by a known polymerization method such as aryl coupling and the like using a suitable catalyst.

A$^{11}$ represents a structural unit represented by the formula (1), and A$^{12}$ represents a structural unit represented by the formula (4). X$^{11}$, X$^{12}$, X$^{13}$ and X$^{14}$ represent each independently a polymerization reactive group.

The polymerization reactive group includes, for example, a halogen atom, a borate residue, and an organotin residue substituted with three alkyl groups. Here, the boric acid residue means a group represented by —B(OH)$_2$.

The halogen atom as the polymerization reactive group includes, for example, a fluorine atom, a chlorine atom, a bromine atom, an iodine atom.

The borate residue as the polymerizable functional group denotes an atomic group obtained by removing from an ester of boronic acid (HB(OH)$_2$) a hydrogen atom bonded to boron.

The number of carbon atoms of the borate residue is usually 2 to 40. The borate residue includes, for example, groups represented by the following formulae.

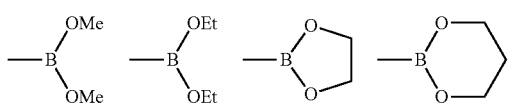

-continued

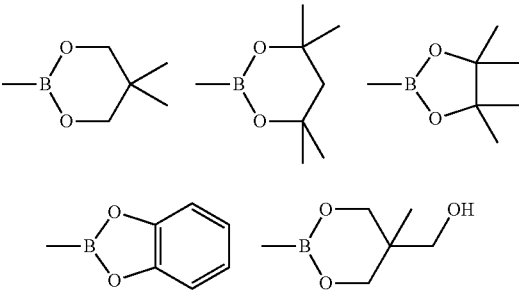

(wherein Me represents a methyl group and Et represents an ethyl group.)

The organotin residue substituted with three alkyl groups as the polymerization reactive group includes, for example, an organotin residue substituted with three methyl groups and an organotin residue substituted with three butyl groups. The number of carbon atoms of the organotin residue is usually 3 to 60.

The polymerization method such as aryl coupling and the like includes, for example, a method of polymerization by the Suzuki coupling reaction (Chemical Review, 1995, vol. 95, pp. 2457-2483) and a method of polymerization by the Stille coupling reaction (European Polymer Journal, 2005, vol. 41, pp. 2923-2933).

The polymerization reactive group is, in the case of use of a nickel catalyst or a palladium catalyst such as in the Suzuki coupling reaction and the like, preferably a halogen atom, a borate residue or a boric acid residue, and from the standpoint of simplicity of the polymerization reaction, preferably a bromine atom, an iodine atom or a borate residue.

When the polymer compound of the present invention is polymerized by the Suzuki coupling reaction, the ratio (A/B) of the total molar number (A) of a bromine atom and an iodine atom as the polymerization reactive group to the total molar number (B) of a borate residue as the polymerization reactive group is preferably 0.7 to 1.3, more preferably 0.8 to 1.2.

The polymerization reactive group is, in the case of use of a palladium catalyst such as in the Stille coupling reaction and the like, preferably a halogen atom or an organotin residue substituted with three alkyl groups, and from the standpoint of simplicity of the polymerization, preferably a bromine atom, an iodine atom or an organotin residue substituted with three alkyl groups.

When the polymer compound of the present invention is polymerized by the Stille coupling reaction, the ratio (C/D) of the total molar number (C) of a bromine atom and an iodine atom as the polymerization reactive group to the total molar number (D) of an organotin residue substituted with three alkyl groups as the polymerization reactive group is preferably 0.7 to 1.3, more preferably 0.8 to 1.2.

The organic solvent used for polymerization includes, for example, benzene, toluene, xylene, chlorobenzene, dichlorobenzene, tetrahydrofuran and dioxane. These organic solvents may be used singly or two or more of them may be used in combination.

The base used for polymerization includes, for example, inorganic bases such as sodium carbonate, potassium carbonate, cesium carbonate, potassium fluoride, cesium fluoride, tripotassium phosphate and the like, and organic bases such as tetrabuylammonium fluoride, tetrabuylammonium chloride, tetrabuylammonium bromide, tetraethylammonium hydroxide, tetrabutylammonium hydroxide and the like.

The catalyst used for polymerization is preferably a catalyst compound of a transition metal complex such as a palladium complex such as tetrakis(triphenylphosphine)palladium, tris(dibenzylideneacetone)dipalladium, palladium acetate, dichlorobistriphenylphosphinepalladium and the like, and if necessary, a ligand such as triphenylphosphine, tritert-butylphosphine, tricyclohexylphosphine and the like. As these catalyst, those previously synthesized may be used, or those prepared in the reaction system may be used as they are. These catalysts may be used singly or two or more of them may be used in combination.

The reaction temperature of polymerization is preferably 0 to 200° C., more preferably 0 to 150° C., further preferably 0 to 120° C.

The reaction time of polymerization is usually 1 hour or longer, preferably 2 to 500 hours.

The post treatment of polymerization can be conducted by a known method, and includes, for example, a method in which into a lower alcohol such as methanol and the like, a reaction solution obtained in the above-described polymerization is added and allowed to deposit a precipitate which is then filtrated and dried.

When the purity the polymer compound of the present invention is low, it is preferable that the polymer compound is purified by a method such as recrystallization, continuous extraction by a Soxhlet extractor, column chromatography and the like.

<Compound>

The compound of the present invention is a compound represented by the formula (5a), and can be suitably used in the above-described method of producing a polymer compound, as a raw material of the polymer compound of the present invention.

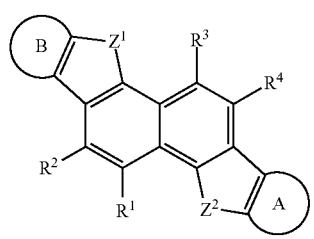

(5a)

In the formula (5a), $R^1$, $R^2$, $R^3$, $R^4$, Ring A, Ring B, $Z^1$ and $Z^2$ represent the same meaning as described above.

The substituent which the heterocyclic ring represented by Ring A and Ring B may have includes, for example, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue or an organotin residue, and these groups may have a substituent.

The compound represented by the formula (5a) is preferably a compound represented by the formula (6a) since then synthesis of the compound of the present invention is easy.

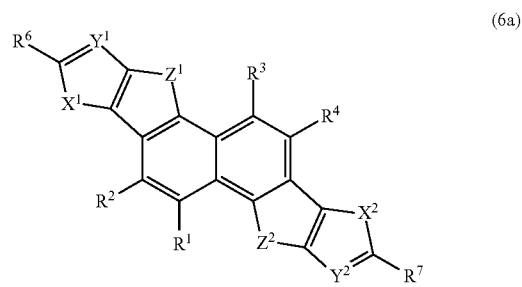

(6a)

In the formula (6a), $R^1$, $R^2$, $R^3$, $R^4$, $X^1$, $X^2$, $Y^1$, $Y^2$, $Z^1$ and $Z^2$ represent the same meaning as described above. $R^6$ and $R^7$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue or an organotin residue, and these groups may have a substituent.

The definition and specific examples of the alkyl group, the alkoxy group, the alkylthio group, the aryl group, the mono-valent heterocyclic group, the halogen atom, the silyl group, the amino group, the alkenyl group, the alkynyl group, the alkylcarbonyl group and the alkoxycarbonyl group are the same as the definition and specific examples of the alkyl group, the alkoxy group, the alkylthio group, the aryl group, the mono-valent heterocyclic group, the halogen atom, the silyl group, the amino group, the alkenyl group, the alkynyl group, the alkylcarbonyl group and the alkoxycarbonyl group as the above-described substituent which the heterocyclic ring may have. The definition and specific examples of the borate residue, the boric acid residue or the organotin residue are the same as the definition and specific examples of the borate residue, the boric acid residue or the organotin residue as the above-described polymerization reactive group.

The compound represented by the formula (5a) is preferably a compound represented by the formulae (5a-1) to (5a-33), more preferably a compound represented by the formulae (5a-1) to (5a-22) in which $Z^1$ and $Z^2$ are a group represented by the formula (Z-1), further preferably a compound represented by the formulae (5a-1) to (5a-14) since when the above-described polymer compound of the present invention is produced using the compound of the present invention, an organic film solar battery produced by using the polymer compound is more excellent in ff (fill factor).

(5a-1)
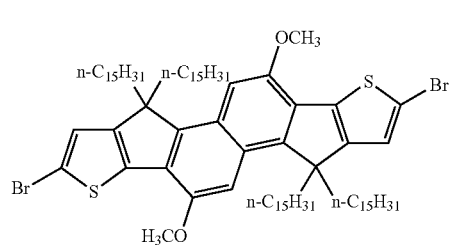
(5a-2)
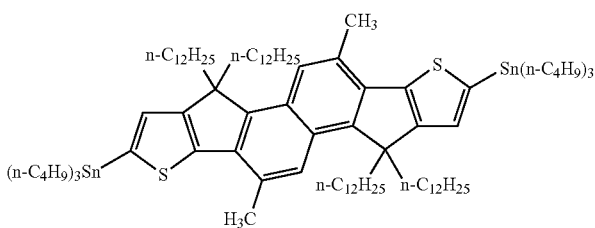
(5a-3)
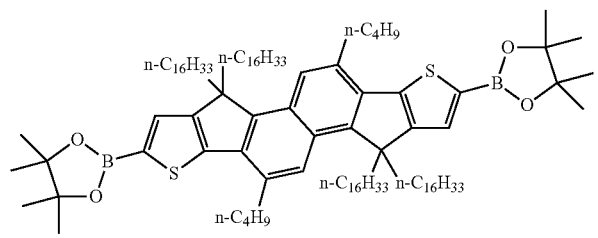
(5a-4)
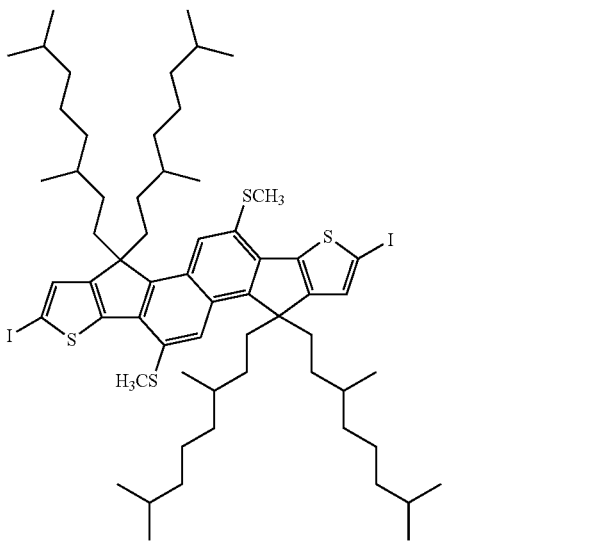
(5a-5)
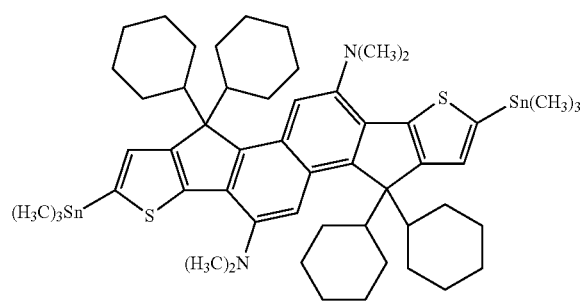
(5a-6)
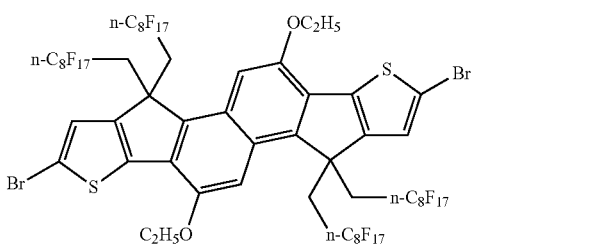
(5a-7)
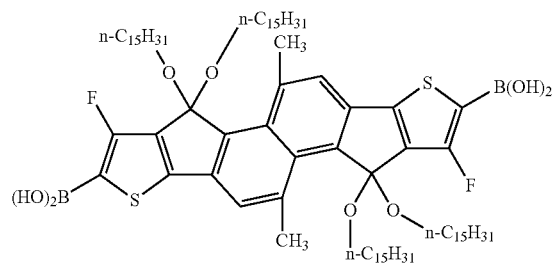
(5a-8)
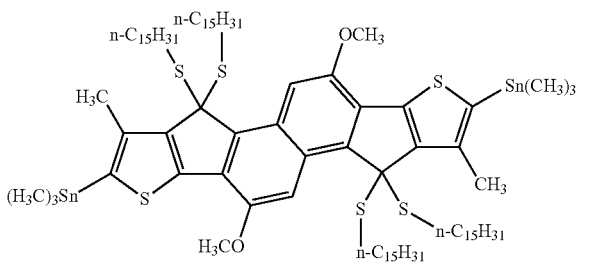
(5a-9)
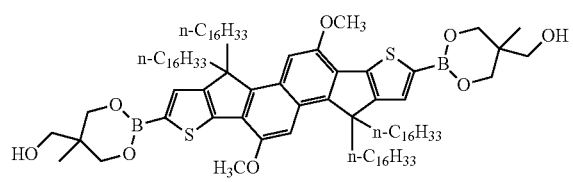
(5a-10)
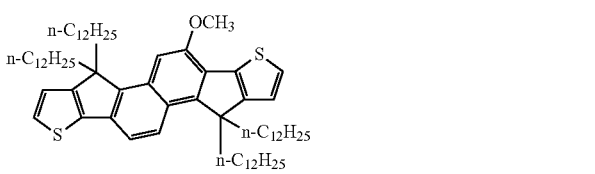

-continued
(5a-11)
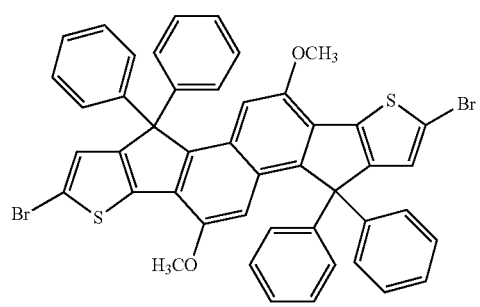
(5a-12)
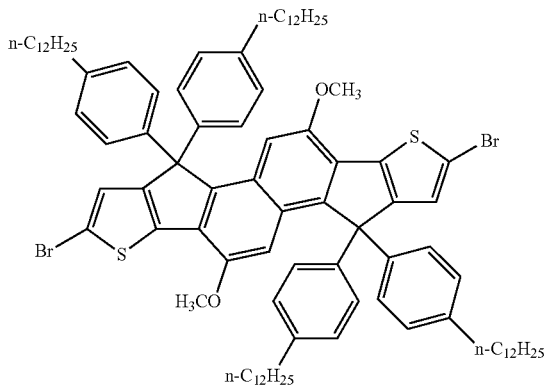
(5a-13)
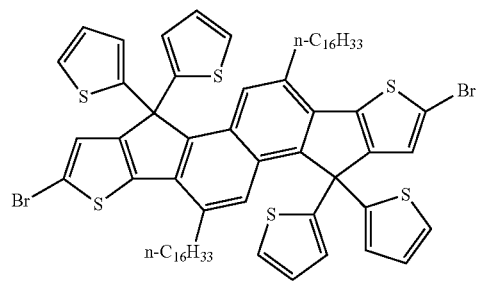
(5a-14)
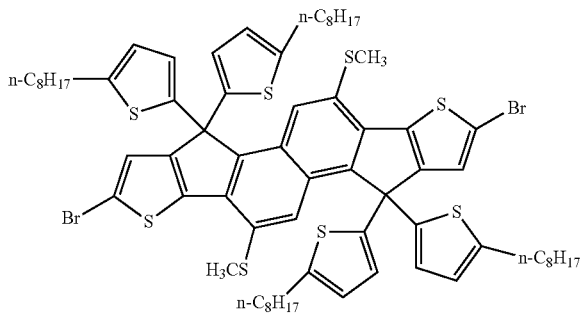
(5a-15)
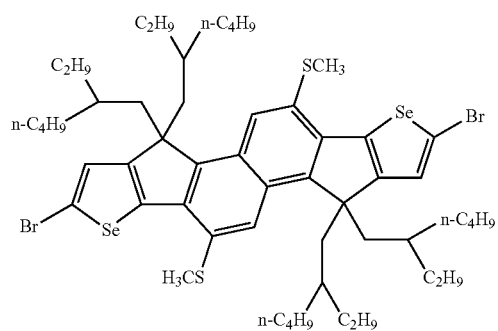
(5a-16)
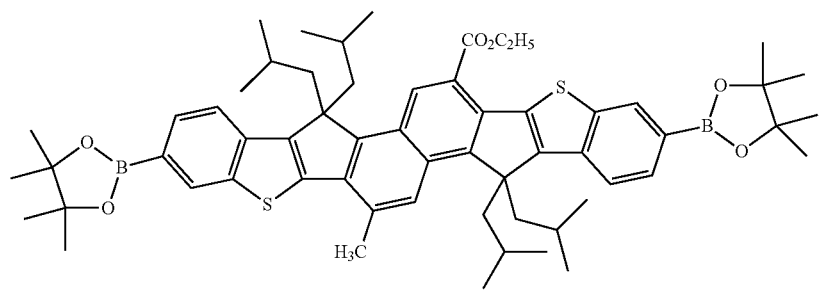
(5a-17)
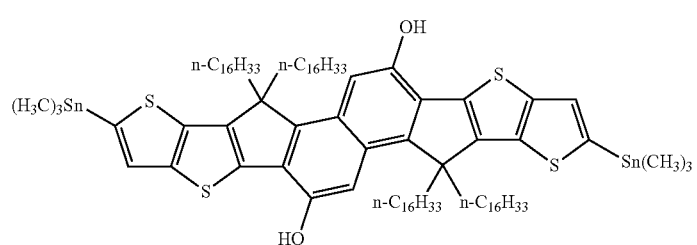

-continued
(5a-18)
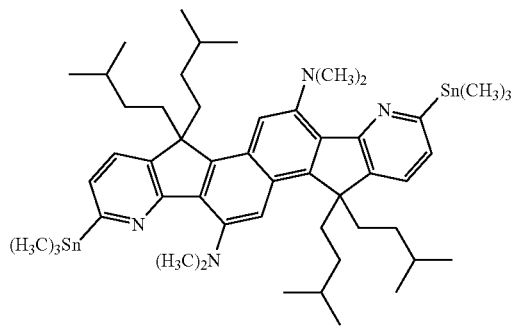
(5a-19)
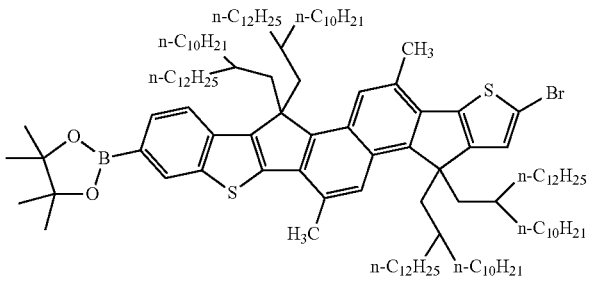
(5a-20)
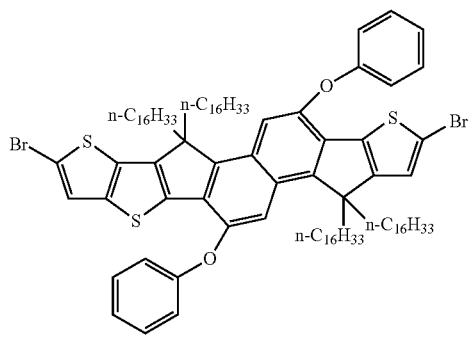
(5a-21)
(5a-22)
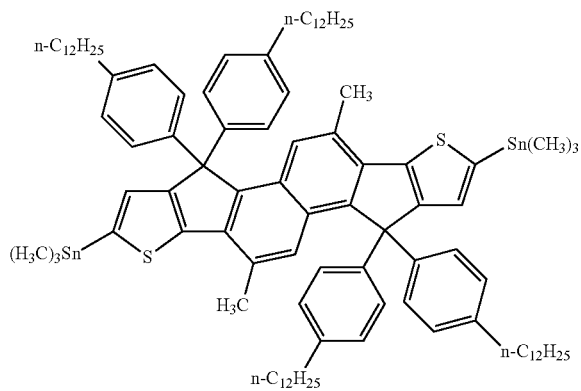
(5a-23)
(5a-24)
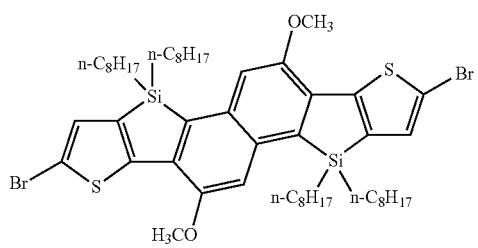
(5a-25)
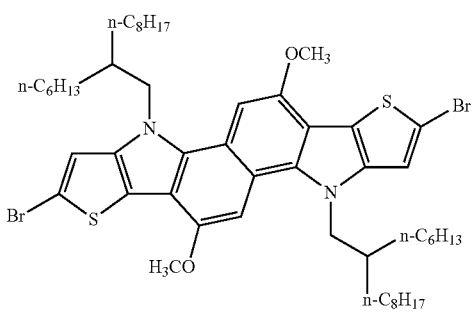

(5a-26)
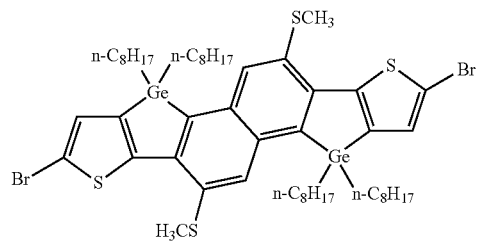

(5a-27)
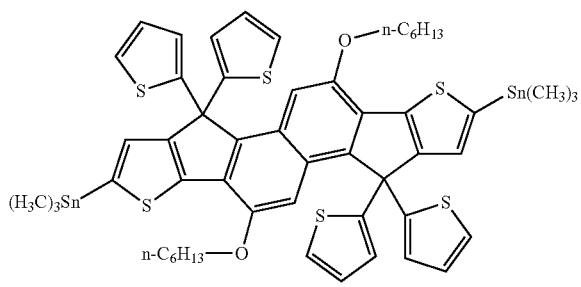

(5a-28)
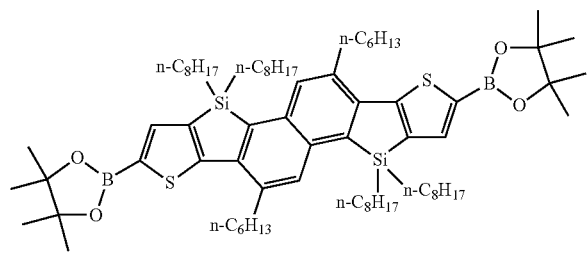

(5a-29)

(5a-30)
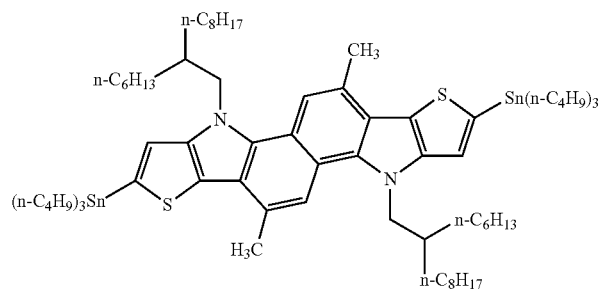

(5a-31)

(5a-32)
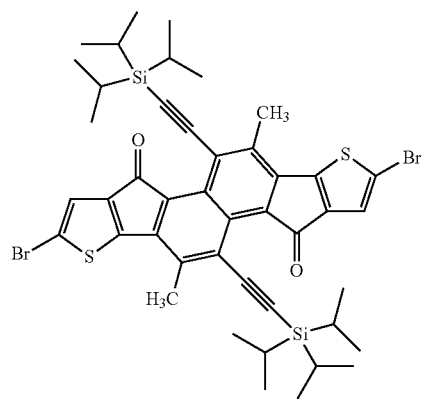

(5a-33)
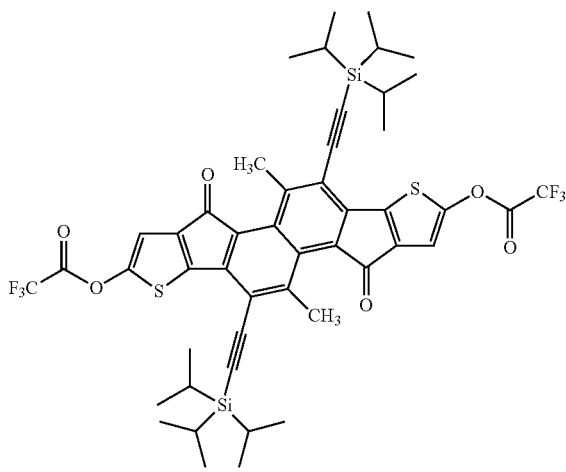

<Method of Producing Compound>

Next, the method of producing a compound of the present invention will be explained.

Though the compound represented by the formula (5a) may be produced by any method, for example, the compound can be produced by a bromination reaction, the Suzuki coupling reaction, the Wolff-Kishner reducing reaction, the Buchwald-Hartwig amination reaction or an oxidative cyclization reaction as explained below.

The compound represented by the formula (S5) (compound of the formula (5a) in which $Z^1$ and $Z^2$ are a group represented by the formula (Z-5)) can be produced, for example, by a method comprising a first step in which a compound represented by the formula (S1), a compound represented by the formula (S2) and a compound represented by the formula (S3) are reacted by the Suzuki coupling reaction and a second step in which the compound represented by the formula (S4) obtained in the first step is subjected to intramolecular cyclization.

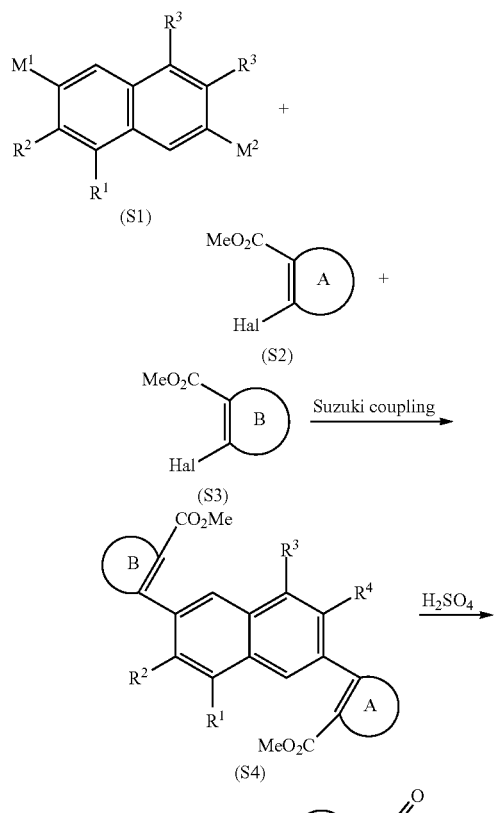

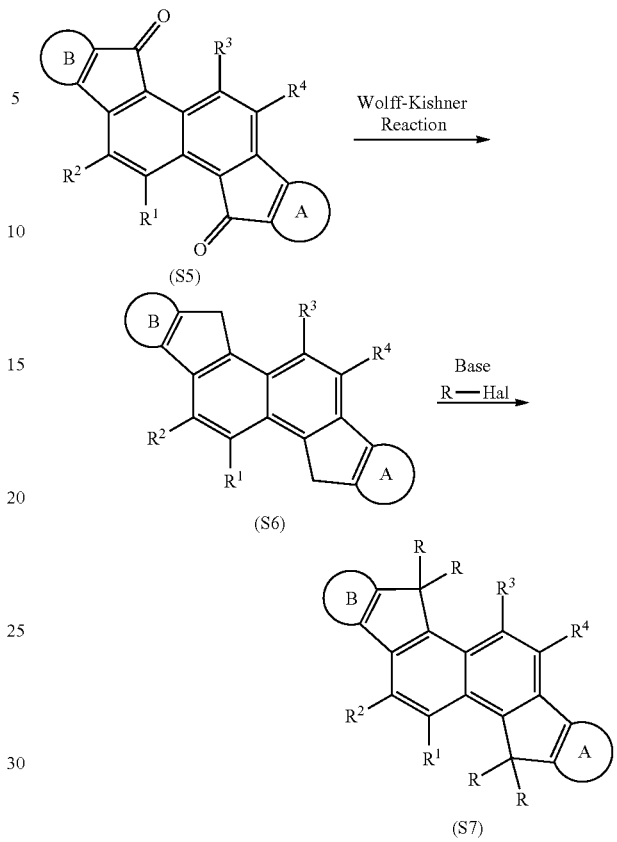

In the formulae (S1) to (S5), $R^1$, $R^2$, $R^3$, $R^4$, Ring A and Ring B represent the same meaning as described above. $M^1$ and $M^2$ represent each independently a borate residue or a boric acid residue (group represented by —$B(OH)_2$). Hal represents an iodine atom, a bromine atom or a chlorine atom. Hal in the formula (S2) and Hal in the formula (S3) may be the same or different.

The compound represented by the formula (S7) (compound of the formula (5a) in which $Z^1$ and $Z^2$ are a group represented by the formula (Z-1)) can be produced, for example, by a method comprising a first step in which the compound represented by the formula (S5) is reacted by the Wolff-Kishner cyclization reaction and a second step in which the compound represented by the formula (S6) obtained in the first step, a base such as sodium alkoxide and the like, and an alkyl halide are reacted.

In the formulae (S5) to (S7), $R^1$, $R^2$, $R^3$, $R^4$, R, Ring A, Ring B and Hal represent the same meaning as described above.

The compound represented by the formula (S7) (compound of the formula (5a) in which $Z^1$ and $Z^2$ are a group represented by the formula (Z-1)) can be produced, in addition, by a method comprising a first step in which a compound represented by the formula (S1), a compound represented by the formula (S8) and a compound represented the formula (S9) are reacted by the Suzuki coupling reaction, a second step in which a compound represented by the formula (S10) obtained in the first step and butyllithium are reacted to cause lithiation, and further reacted with a ketone, and a third step in which a compound represented by the formula (S11) obtained in the second step and an acid such as trifluoroboric acid, sulfuric acid and the like are reacted to cause cyclization.

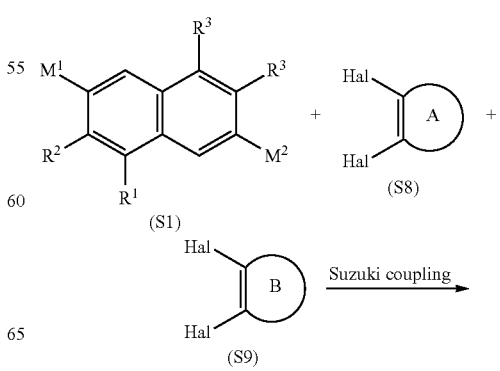

In the formulae (S1) and (S7) to (S11), $R^1$, $R^2$, $R^3$, $R^4$, R, $M^1$, $M^2$, Ring A, Ring B and Hal represent the same meaning as described above. A plurality of Hal present in the formula (S8) may be the same or different, a plurality of Hal present in the formula (S9) may be the same or different, and Hal in the formula (S8) and Hal in the formula (S9) may be the same or different.

The compound represented by the formula (S13) (compound of the formula (5a) in which $Z^1$ and $Z^2$ are a group represented by the formula (Z-2) or the formula (Z-3)) can be produced, for example, by a method comprising a first step in which a compound represented by the formula (S10) described above and a halogenating agent such as N-bromosuccinimide and the like are reacted and a second step in which the compound represented by the formula (S12) obtained in the first step and butyllithium are reacted to cause lithiation, and further, reacted with a compound represented the formula: $R_2ECl_2$ and the like.

In the formulae (S10), (S12) and (S13), $R^1$, $R^2$, $R^3$, $R^4$, R, Ring A, Ring B and Hal represent the same meaning as described above. E represents a silicon atom or a germanium atom. A plurality of Hal present in the formula (S10) may be the same or different, and a plurality of Hal present in the formula (312) may be the same or different.

The compound represented by the formula (S15) (compound of the formula (5a) in which $Z^1$ and $Z^2$ are a group represented by the formula (Z-4)) can be produced, for example, by reacting a compound represented by the formula (S12) described above and a compound represented by the formula (S14) by the Buchwald-Hartwig amination reaction.

In the formulae (S12), (S14) and (S15), $R^1$, $R^2$, $R^3$, $R^4$, R, Ring A, Ring B and Hal represent the same meaning as described above. A plurality of Hal present in the formula (S12) may be the same or different.

The compound represented by the formula (S7) (compound of the formula (5a) in which $Z^1$ and $Z^2$ are a group represented by the formula (Z-1)) can be produced by subjecting a compound represented by the formula (S16) to intramolecular cyclization. Preferably, the compound represented by the formula (S7) can be produced by a method comprising a step of contacting a compound represented by the formula (S16) with an acid.

The compound represented by the formula (S16) can be produced by reacting a compound represented by the formula (S19), a compound represented by the formula (S23) and a compound represented by the formula (S24) by the Suzuki coupling reaction.

Further, the compound represented by the formula (S7) can be produced by a method comprising a first step in which a compound represented by the formula (S19), a compound represented by the formula (S23) and a compound represented by the formula (S24) are reacted by the Suzuki coupling reaction and a second step in which the compound represented by the formula (S16) obtained in the first step is subjected to intramolecular cyclization. The compound represented by the formula (S7) in the second step can be produced, preferably, by a method of contacting a compound represented by the formula (S16) with an acid.

In the formulae (S7), (S16), (S19), (S23) and (S24), $R^1$, $R^2$, $R^3$, $R^4$, R, Ring A, Ring B and Hal represent the same meaning as described above. $M^3$ and $M^4$ represent each independently a borate residue or a boric acid residue (group represented by —B(OH)$_2$). $R^p$ represents an alkyl group, a silyl group or an acetyl group. A plurality of Hal present in the formula (S24) may be the same or different. $R^p$ in the formula (S19) and $R^p$ in the formula (S23) may be the same or different.

The borate residue represented by $M^3$ and $M^4$ in the formulae (S19) and (S23) denotes an atomic group obtained by removing from an ester of boronic acid (HB(OH)$_2$) a hydrogen atom bonded to boron.

The number of carbon atoms of the borate residue is usually 2 to 40.

The borate residue includes groups represented by the following formulae:

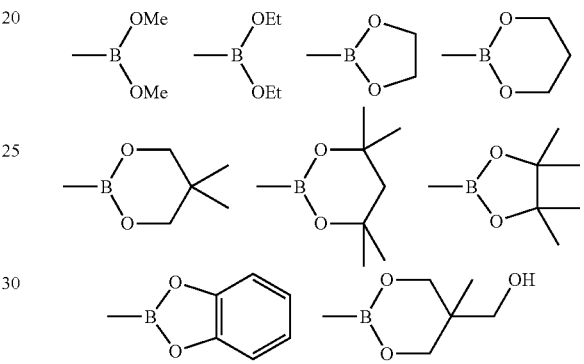

(wherein Me represents a methyl group and Et represents an ethyl group.)
and the like.

The halogen atom represented by Hal in the formula (S24) includes a fluorine atom, a chlorine atom, a bromine atom and an iodine atom. The halogen atom is preferably a bromine atom or an iodine atom, more preferably a bromine atom from the standpoint of easiness of synthesis of the compound of the present invention.

The step of reacting a compound represented by the formula (S19), a compound represented by the formula (S23) and a compound represented by the formula (S24) by the Suzuki coupling reaction to obtain a compound represented by (S16) will be explained below.

The Suzuki coupling reaction is conducted in the presence of a catalyst and a base, usually in a solvent.

As the catalyst, a palladium catalyst is usually used. The palladium catalyst includes, for example, Pd(0) catalyst, Pd(II) catalyst and the like. The palladium catalyst includes, specifically, palladium[tetrakis(triphenylphosphine)], dichlorobis(triphenylphosphine)palladium, palladium acetate, tris(dibenzylideneacetone)dipalladium, bis(dibenzylideneacetone)palladium and the like, and preferable from the standpoint of easiness of reaction operation and from the standpoint of reaction speed are dichlorobis(triphenylphosphine)palladium, palladium acetate and tris(dibenzylideneacetone)dipalladium.

The addition amount of the palladium catalyst may be an effective amount as a catalyst, and is usually 0.001 to 10 mol, preferably 0.01 to 1 mol with respect to 1 mol of the compound represented by the formula (S24).

When the palladium catalyst is used, a phosphorus compound such as triphenylphosphine, tri(o-tolyl)phosphine,

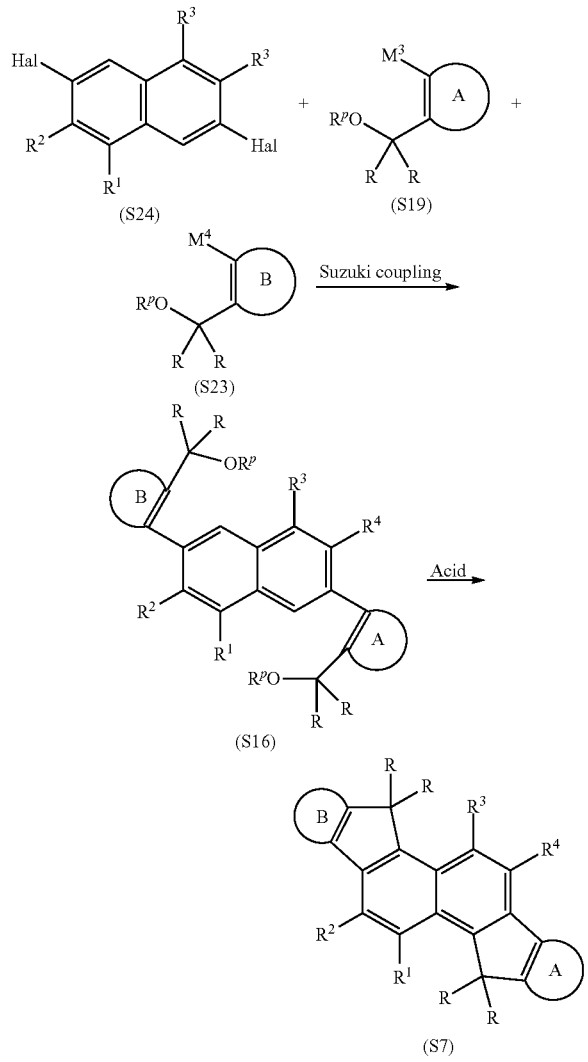

tri(o-methoxyphenyl)phosphine, tri(t-butyl)phosphine and the like can be added as a ligand. In this case, the addition amount of a ligand is usually 0.001 to 10 mol, preferably 0.01 to 1 mol with respect to 1 mol of the total molar number of the palladium catalyst.

The base includes inorganic bases, organic bases, inorganic salts and the like. The inorganic base includes, for example, potassium carbonate, sodium carbonate, barium hydroxide and the like. The organic base includes, for example, triethylamine, tributylamine and the like. The inorganic salt includes, for example, cesium fluoride and the like.

The addition amount of the base is usually 0.5 to 100 mol %, preferably 0.9 to 20 mol, more preferably 1 to 10 mol % with respect to the sum of molar numbers of one or more compounds represented by the formula (S24).

When a solvent is used in the reaction, the solvent includes, for example, aromatic hydrocarbon solvents such as toluene and the like; amide solvents such as N,N-dimethylformamide (dMF) and the like; ether solvents such as tetrahydrofuran (tHF), dimethoxyethane, 1,4-dioxane and the like; water, and the like, and THF and 1,4-dioxane are more preferable.

These solvents may be used singly or two or more of them can be used in admixture.

By adding the base in the form of an aqueous solution, the reaction may be performed in a two-phase system. When an inorganic salt is used as the base, it is usually added in the form of an aqueous solution and reacted from the standpoint of solubility of the inorganic salt. In the case of performing the reaction in a two-phase system by adding the base in the form of an aqueous solution, a phase transfer catalyst such as a quaternary ammonium salt and the like may also be added, if necessary.

The use amount of the solvent is, for example, in the range of 0.5 to 500 parts by weight, preferably in the range of 1 to 300 parts by weight with respect to 1 part by weight of the compound represented by the formula (S24).

The use amount of the compound represented by (S19) is usually 1 to 100 mol with respect to 1 mol of the compound represented by the formula (S24). The use amount of the compound represented by (S23) is usually 1 to 100 mol with respect to 1 mol of the compound represented by the formula (S24).

The temperature for conducting the reaction is, depending on the solvent, usually about 50 to 160° C., preferably 60 to 120° C. The reaction may also be conducted under conditions in which the temperature is raised to around the boiling point of the solvent and the solvent is refluxed. The reaction is usually conducted until a compound represented by the formula (S24), a compound represented by the formula (S19) or a compound represented by the formula (S23) in the reaction mixtures is not reduced or the resultant compound represented by the formula (S16) does not increase by confirming by an analysis means such as liquid chromatography, gas chromatography and the like. The time of the reaction is, specifically, in the range of 1 minute to 48 hours.

It is preferable that the reaction is conducted in the reaction system in which a catalyst is not deactivated under an inert atmosphere such as an argon gas, a nitrogen gas and the like. For example, it is preferable that the reaction is conducted in the system deaerated sufficiently with an argon gas, a nitrogen gas or the like.

The compound represented by the formula (S16) can be obtained by carrying out usual post treatments such as extraction of the product with an organic solvent and distilling off of the solvent. Further, the compound represented by the formula (S16) can be isolated and purified by usual purification means such as recrystallization, various chromatographies and the like.

Next, the step of subjecting the compound represented by the formula (S16) to intramolecular cyclization to produce a compound represented by the formula (S17) will be illustrated.

When an acid is used in the step, the reaction may be conducted in the presence of only an acid, or conducted in the presence of an acid and a solvent.

The acid includes Lewis acids and Bronsted acids. As the acid, for example, known acids used in the Friedel-Crafts reaction can be used. Specific examples of the acid include hydrochloric acid, hydrobromic acid, hydrofluoric acid, sulfuric acid, nitric acid, formic acid, acetic acid, propionic acid, oxalic acid, benzoic acid, benzenesulfonic acid, p-toluenesulfonic acid, trifluoroacetic acid, trifluoromethanesulfonic acid, boron tribromide, boron trifluoride diethyl ether complex, aluminum chloride, aluminum bromide, tin(IV) chloride, silicon(IV) chloride, iron(III) chloride, titanium tetrachloride, zinc chloride, beryllium chloride, cadmium chloride, gallium chloride, antimony chloride, and mixtures thereof, and the like.

Of acids, Lewis acids are preferable, and boron tribromide, boron trifluoride diethyl ether complex and aluminum chloride are more preferable.

These acids may be used singly or two or more of them can be used in admixture.

The use amount of the acid is usually 2 to 100 mol with respect to 1 mol of the compound represented by the formula (S16).

When a solvent is used, the solvent includes saturated hydrocarbon solvents such as pentane, hexane, heptane, octane, cyclohexane and the like; unsaturated hydrocarbon solvents such as benzene, toluene, ethylbenzene, xylene and the like; halogenated saturated hydrocarbon solvents such as carbon tetrachloride, chloroform, dichloromethane, chlorobutane, bromobutane, chloropentane, bromopentane, chlorohexane, bromohexane, chlorocyclohexane, bromocyclohexane and the like; halogenated unsaturated hydrocarbon solvents such as chlorobenzene, dichlorobenzene, trichlorobenzene and the like. Of them, halogenated saturated hydrocarbon solvents are preferable, dichloromethane is more preferable.

These solvents may be used singly or two or more of them can be used in admixture.

When a solvent is used, the use amount of the solvent is, for example, in the range of 0.5 to 500 parts by weight and the like, preferably in the range of 1 to 300 parts by weight and the like with respect to 1 part by weight of the compound represented by the formula (S16).

When a solvent is used, the compound represented by the formula (S16) and an acid are mixed each in any order into a solvent. It is preferable that an acid is mixed with a mixture which is prepared by mixing the compound represented by the formula (S16) with a solvent.

The reaction temperature is usually in the range of −80 to 300° C., preferably in the range of 50 to 200° C., more preferably in the range of 50° C. to 100° C. Though the reaction time is not limited, the reaction is usually conducted until a compound represented by the formula (S16) in the mixture is not reduced or the resultant compound represented by the formula (S7) does not increase by confirming by an analysis means such as liquid chromatography, gas chromatography and the like. Specifically, the reaction time is in the range of 1 minute to 120 hours.

The compound represented by the formula (S7) can be obtained by carrying out post treatments such as extraction of the product with an organic solvent, distilling off of the solvent and the like. Further, the compound represented by the formula (S7) can be isolated and purified by usual purification means such as recrystallization, various chromatographies and the like.

<Organic Semiconductor Material>

The organic semiconductor material of the present invention may be a material containing one polymer compound of the present invention singly or a material containing two or more polymer compounds of the present invention. The organic semiconductor material of the present invention may further contain a compound having carrier transportability (may be low molecular weight compound or polymer compound) in addition to the polymer compound of the present invention. When the organic semiconductor material of the present invention contains other components than the polymer compound of the present invention, the polymer compound of the present invention is preferably contained in an amount of 30 wt % or more, more preferably in an amount of 50 wt % or more, further preferably in an amount of 70 wt % or more.

The compound having carrier transportability includes low molecular weight compounds such as arylamine derivatives, stilbene derivatives, oligothiophene and derivatives thereof, oxadiazole derivatives, fullerenes and derivatives thereof and the like; polymer compounds such as polyvinylcarbazole and derivatives thereof, polyaniline and derivatives thereof, polythiophene and derivatives thereof, polypyrrole and derivatives thereof, polyphenylenevinylene and derivatives thereof, polythienylenevinylene and derivatives thereof, polyfluorene and derivatives thereof and the like.

The organic semiconductor material may contain, as a polymer binder, a polymer compound material different from the polymer compound of the present invention, for improving its property. As the polymer binder, those not excessively lowering carrier transportability are preferable.

Examples of the polymer binder include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride and polysiloxane.

<Organic Semiconductor Device>

The organic semiconductor device of the present invention is an organic semiconductor device having a first electrode and a second electrode and having an active layer between the first electrode and the second electrode, wherein the active layer contains the polymer compound of the present invention.

The organic semiconductor device of the present invention may further contain an electrode in addition to the first electrode and the second electrode.

Since the polymer compound of the present invention has high mobility, if an organic film containing the polymer compound of the present invention is used in an organic semiconductor device, electrons and holes injected from an electrode, and charges generated by optical absorption can be transported. Utilizing these properties, the polymer compound of the present invention can be suitably used in various organic semiconductor devices such as a photoelectric conversion device, an organic transistor, an organic electroluminescent device, an organic field-effect transistor sensor, an organic conductivity modulation sensor and the like. These devices will be illustrated individually below.

(Photoelectric Conversion Device)

A photoelectric conversion device containing the polymer compound of the present invention has at least one active layer containing the polymer compound of the present invention between a pair of electrodes at least one of which is transparent or semi-transparent.

A preferable embodiment of the photoelectric conversion device containing the polymer compound of the present invention has a pair of electrodes at least one of which is transparent or semi-transparent and an active layer formed of a composition composed of a p-type organic semiconductor and an n-type organic semiconductor. It is preferable that the polymer compound of the present invention is used as a p-type organic semiconductor. The motion mechanism of the photoelectric conversion device of this embodiment will be explained. Incident optical energy from a transparent or semi-transparent electrode is absorbed in an electron accepting compound such as fullerene derivatives and the like (n-type organic semiconductor) and/or an electron donating compound such as the polymer compound of the present invention and the like (p-type organic semiconductor), to generate excitons binding electrons and holes. When the generated excitons move and reach the heterojunction interface at which the electron accepting compound and the electron donating compound are adjacent, electrons and holes separate due to differences of respective HOMO energy and LUMO energy at the interface, and independently movable charges (electrons and holes) are generated. The generated charges move to respective electrodes, thus, electric energy (current) can be taken outside.

The photoelectric conversion device produced by using the polymer compound of the present invention is usually formed on a substrate. This substrate may advantageously be one which does not chemically change in forming an electrode and in forming a layer of an organic substance. The material of the substrate includes, for example, glass, plastic, polymer film and silicon. In the case of an opaque substrate, it is preferable that the opposite electrode (namely, remote electrode from substrate) is transparent or semi-transparent.

Another embodiment of the photoelectric conversion device containing the polymer compound of the present invention is a photoelectric conversion device having a first active layer containing the polymer compound of the present invention and a second active layer adjacent to the first active layer and containing an electron accepting compound such as fullerene derivatives and the like, between a pair of electrodes at least one which is transparent or semi-transparent.

The material of the above-described transparent or semi-transparent electrode includes an electrically conductive metal oxide film, a semi-transparent metal film and the like. Specifically, films fabricated by using an electrically conductive materials such as indium oxide, zinc oxide, tin oxide, and a composite thereof: indium.tin.oxide (hereinafter, referred to as "ITO" in some cases), indium.zinc.oxide and the like, and NESA, gold, platinum, silver, copper and the like are used, and ITO, indium.zinc.oxide and tin oxide are preferable. The electrode fabrication method includes a vacuum vapor deposition method, a sputtering method, an ion plating method, a plating method and the like. As the electrode material, transparent electrically conductive films made of organic substances such as polyaniline and derivatives thereof, polythiophene and derivatives thereof and the like may be used.

One electrode may not be transparent, and as the material of this electrode, metals, electrically conductive polymers and the like can be used. Specific examples of the electrode material include metals such as lithium, sodium, potassium, rubidium, cesium, magnesium, calcium, strontium, barium, aluminum, scandium, vanadium, zinc, yttrium, indium, cerium, samarium, europium, terbium, ytterbium and the like, and alloys composed of these two or more metals, or alloys composed of at least one of the above-described metals and at least one metal selected from the group consisting of gold, silver, platinum, copper, manganese, titanium, cobalt, nickel, tungsten and tin; graphite, graphite intercalation compound, polyaniline and derivatives thereof, and polythiophene and derivatives thereof. The alloy includes a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy and the like.

An additional intermediate layer other than the active layer may be used as a means for improving photoelectric conversion efficiency. The material used as the intermediate layer includes halides of alkali metals and alkaline earth metals such as lithium fluoride and the like, oxides such as titanium oxide and the like, PEDOT (poly3,4-ethylenedioxythiophene), and the like.

The active layer may contain one polymer compound of the present invention or may contain two or more polymer compounds of the present invention in combination. Compounds other than the polymer compound of the present invention may be mixed and used as an electron donating compound and/or an electron accepting compound in the active layer. The electron donating compound and the electron accepting compound are determined relatively based on energy levels of these compounds.

The above-described electron donating compound includes, for example, pyrazoline derivatives, arylamine derivatives, stilbene derivatives, triphenyldiamine derivatives, oligothiophene and derivatives thereof, polyvinylcarbazole and derivatives thereof, polysilane and derivatives thereof, polysiloxane derivatives having an aromatic amine residue on the side chain or main chain, polyaniline and derivatives thereof, polythiophene and derivatives thereof, polypyrrole and derivatives thereof, polyphenylenevinylene and derivatives thereof and polythienylenevinylene and derivatives thereof, in addition to the polymer compound of the present invention.

The above-described electron accepting compound includes, for example, carbon materials, metal oxides such as titanium oxide and the like, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, phenanthrene derivatives such as 2,9-dimethyl-4,7-diphenyl-1,10-phenanthroline (vasocuproine) and the like, fullerene, and fullerene derivatives, in addition to the polymer compound of the present invention, and includes preferably titanium oxide, carbon nano tube, fullerene and fullerene derivatives, particularly preferably fullerene and fullerene derivatives.

The fullerene and fullerene derivatives include $C_{60}$, $C_{70}$, $C_{76}$, $C_{78}$, $C_{84}$ and derivatives thereof. Specific structures of fullerene derivatives include those as shown below.

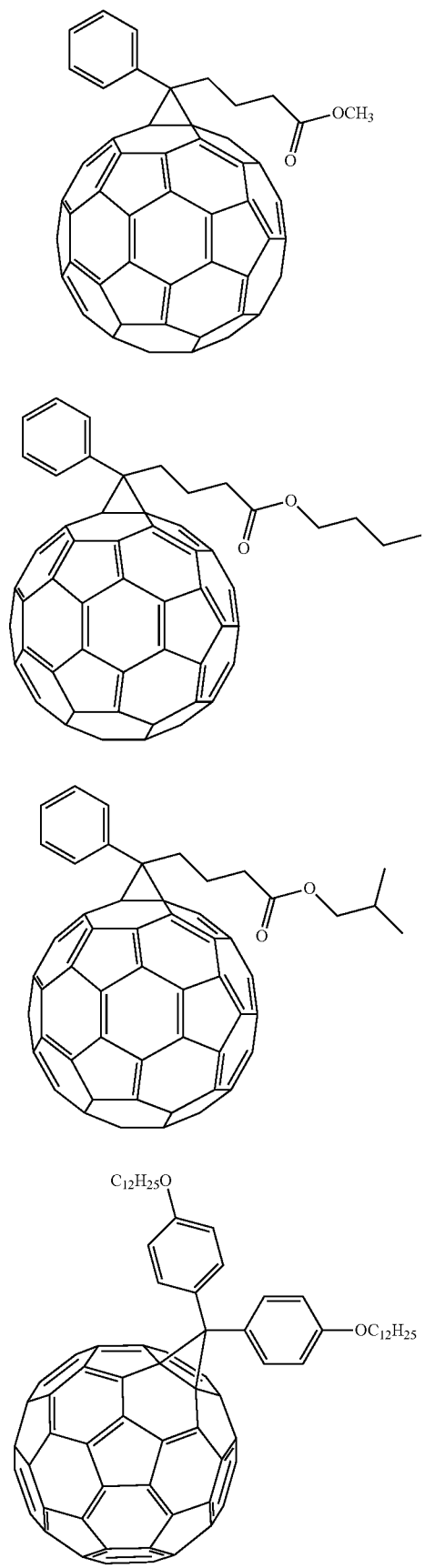

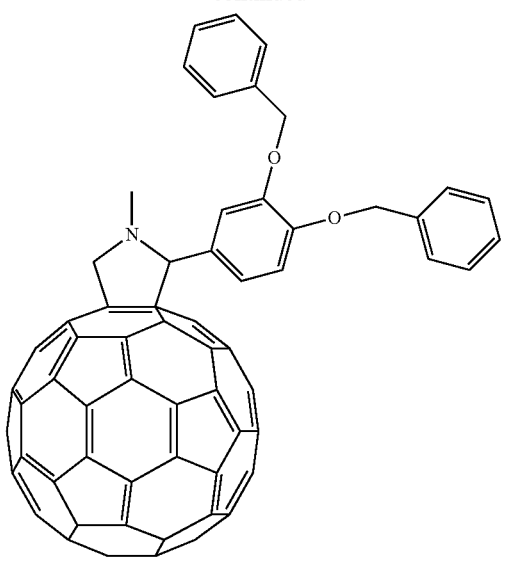

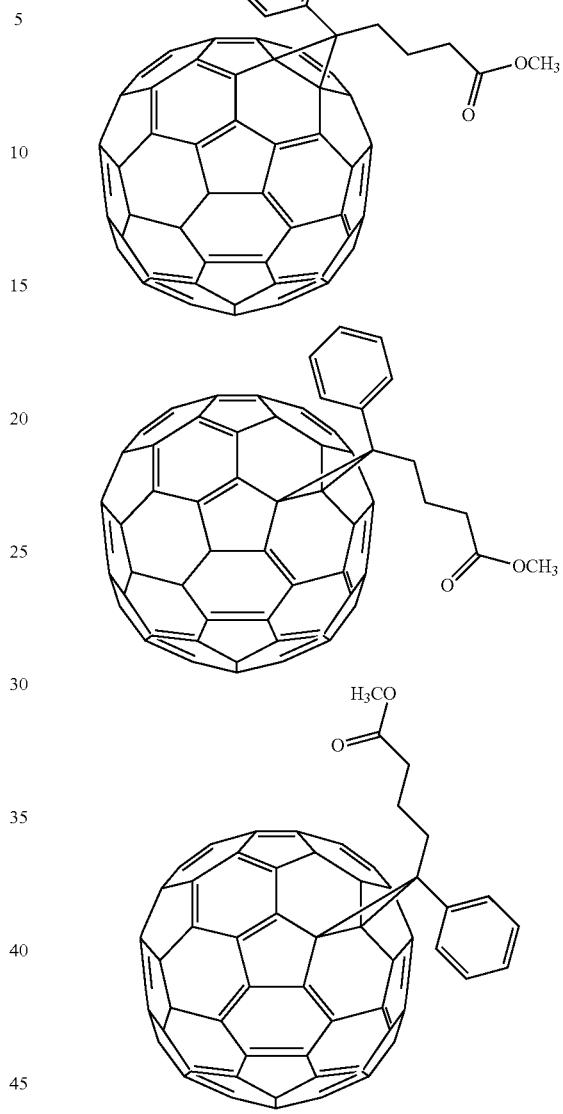

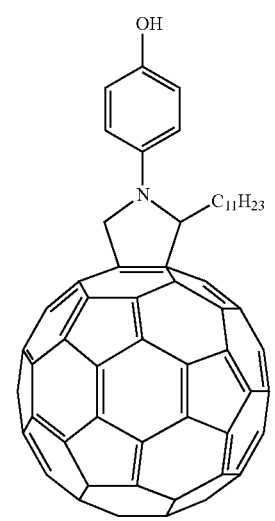

Examples of fullerene derivatives include [6,6]phenyl-C61 butyric acid methyl ester (C60PCBM, [6,6]-Phenyl C61 butyric acid methyl ester), [6,6]phenyl-C70 butyric acid methyl ester (C70PCBM, [6,6]-Phenyl C70 butyric acid methyl ester), [6,6]phenyl-C84 butyric acid methyl ester (C84PCBM, [6,6]-Phenyl C84 butyric acid methyl ester), [6,6]thienyl-C60 butyric acid methyl ester ([6,6]-Thienyl C60 butyric acid methyl ester) and the like.

When the polymer compound of the present invention and a fullerene derivative are contained in the active layer, the proportion of the fullerene derivative is preferably 10 to 1000 parts by weight, more preferably 20 to 500 parts by weight with respect to 100 parts by weight of the polymer compound of the present invention.

The thickness of the active layer is, usually, preferably 1 nm to 100 μm, more preferably 2 nm to 1000 nm, further preferably 5 nm to 500 nm, more preferably 20 nm to 200 nm.

The production method of the active layer may be any method and includes, for example, a method of film formation from a solution containing the polymer compound of the present invention, and a method of film formation by a vacuum vapor deposition method.

A preferable method of producing a photoelectric conversion device is a method of producing a photoelectric conversion device having a first electrode and a second electrode and having an active layer between the first electrode and the second electrode, comprising a step in which a solution (ink) containing the polymer compound of the present invention and a solvent is coated on the first electrode by a coating method for form an active layer, and a step in which the second electrode is formed in the active layer.

The solvent used form film formation from a solution may advantageously be one which dissolves the polymer compound of the present invention. The solvent includes, for example, unsaturated hydrocarbon solvents such as toluene, xylene, mesitylene, tetralin, decalin, bicyclohexyl, n-butylbenzene, sec-butylbenzene, tert-butylbenzene and the like, halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane, bromocyclohexane and the like, halogenated unsaturated hydrocarbon solvents such as chlorobenzene, dichlorobenzene, trichlorobenzene and the like, and ether solvents such as tetrahydrofuran, tetrahydropyran and the like. The polymer compound of the present invention can be usually dissolved at a concentration of 0.1 wt % or more in the above-described solvent.

In the case of film formation using a solution, coating methods such as a slit coat method, a knife coat method, a spin coat method, a casting method, a micro gravure coat method, a gravure coat method, a bar coat method, a roll coat method, a wire bar coat method, a dip coat method, a spray coat method, a screen printing method, a gravure printing method, a flexo printing method, an offset printing method, an inkjet printing method, a dispenser printing method, a nozzle coat method, a capillary coat method and the like can be used, and a slit coat method, a capillary coat method, a gravure coat method, a micro gravure coat method, a bar coat method, a knife coat method, a nozzle coat method, an inkjet printing method and a spin coat method are preferable.

From the standpoint of film formability, the surface tension of the solvent at 25° C. is preferably larger than 15 mN/m, more preferably larger than 15 mN/m and smaller than 100 mN/m, further preferably larger than 25 mN/m and smaller than 60 mN/m.

(Organic Film Solar Battery)

A photoelectric conversion device using the polymer compound of the present invention can be irradiated with a light such as solar light and the like from a transparent or semi-transparent electrode, to generate photovoltaic power between electrodes, and can be operated as an organic film solar battery. By integrating several organic film solar batteries, an organic film solar battery module can be obtained and used.

By irradiating with a light from a transparent or semi-transparent electrode under condition of application of voltage between electrodes or under condition of no application of voltage, photocurrent flows, and the battery can be operated as an organic optical sensor. By integrating several organic optical sensors, an organic image sensor can also be obtained and used.

The organic film solar battery can take basically an identical module structure to a conventional solar battery module. The solar battery module generally has a structure in which a cell is constituted on a supporting substrate of a metal, ceramic and the like, its upper side is covered with a filling resin, a protective glass or the like, and a light is incorporated from the opposite side of the supporting substrate, however, a structure in which a transparent material such as reinforced glass and the like is used as the supporting substrate, a cell is constituted thereon and a light is incorporated from its transparent supporting substrate is also possible. Specifically, module structures called super straight type, substraight type and potting type and a substrate-integrated module structure and the like used in an amorphous silicon solar battery and the like are known. Also an organic film solar battery produced by using the polymer compound of the present invention can appropriately select these module structures depending on the use object, the use place and environments.

Typical super straight type or substraight type modules have a structure in which cells are disposed at a constant distance between supporting substrates of which one side or both sides are transparent and having undergone an antireflection treatment, adjacent cells are mutually connected via a metal lead or flexible wiring and the like, a collector electrode is disposed at the outer peripheral part, and generated electric power is taken outside. Between the substrate and the cell, various kinds of plastic materials such as ethylene vinyl acetate (EVA) and the like may be used in the form of a film or filling resin depending on the object, for protection of the cell and improvement of power collection efficiency. When used at a place needing no covering of the surface with a hard material such as a place receiving little impact from the outside, the surface protective layer is constituted of a transparent plastic film or the above-described filling resin is hardened to give protective function, and one of supporting substrates can be omitted. The periphery of the supporting substrate is fixed in the form of a sandwich by metal frames for confirming interior tight seal and rigidity of a module, and a space between the supporting substrate and the frame is tightly sealed with a sealing material. If a flexible material is used in the cell itself or the supporting substrate, the filling material and the sealing material, it is also possible to constitute a solar batter on a curved surface.

In the case of a solar battery using a flexible supporting body such as a polymer film and the like, cells are formed in sequence while feeding a supporting body in the form of a roll, and cut into desired size, then, peripheral parts are sealed with a flexible material having a moisture-proof property, thus, a battery body can be fabricated. The solar battery using a flexible supporting body can take a module structure called "SCAF" described in Solar Energy Materials and Solar Cells, 48, pp. 383-391. Further, the solar battery using a flexible supporting body can also be adhered and fixed to curved glass and the like and used.

FIG. 1 is a schematic cross-sectional view of the photoelectric conversion device of the present invention. The photoelectric conversion device 300 has a substrate 1, a first electrode 7a formed on the substrate 1, an active layer 2 formed on the first electrode 7a, and a second electrode 7b formed on the active layer 2.

(Organic Electroluminescent Device)

The polymer compound of the present invention can also be used in an organic electroluminescent device (hereinafter, referred to as "organic EL device"). The organic EL device has a light emitting layer between a pair of electrodes at least one of which is transparent or semi-transparent. The organic EL device may contain a hole transporting layer and an electron transporting layer, in addition to the light emitting layer. The polymer compound of the present invention is contained in any of the light emitting layer, the hole transporting layer and the electron transporting layer. The light emitting layer may contain a charge transporting material (denoting a generic name for an electron transporting material and a hole transporting material), in addition to the polymer compound of the present invention. The organic EL device includes a device having an anode, a light emitting layer and a cathode, a device having an anode, a light emitting layer, an electron transporting layer and a cathode wherein an electron transporting layer containing an electron transporting material is further disposed next to the light emitting layer between the cathode and the light emitting layer, a device having an anode, a hole transporting layer, a light emitting layer and a cathode wherein a hole transporting layer containing a hole transporting material is further disposed next to the light emitting layer between the anode and the light emitting layer, a device having an anode, a hole transporting layer, a light emitting layer, and electron transporting layer and cathode; and the like.

(Organic Transistor)

The organic transistor includes one having a constitution having a source electrode and a drain electrode, an active layer acting as a current pathway between these electrodes and containing the polymer compound of the present invention, and a gate electrode controlling the quantity of current passing the current pathway. The organic transistor having such a constitution includes a field effect organic transistor, an electrostatic induction organic transistor and the like.

The field effect organic transistor is usually an organic transistor having a source electrode and a drain electrode, an active layer acting as a current pathway between these electrodes and containing the polymer compound of the present invention, a gate electrode controlling the quantity of current passing the current pathway, and an insulation layer disposed between the active layer and the gate electrode. Particularly, an organic transistor in which a source electrode and a drain electrode are disposed in contact with an active layer, and further, a gate electrode is disposed sandwiching an insulation layer in contact with the active layer is preferable.

The electrostatic induction organic transistor is usually an organic transistor having a source electrode and a drain electrode, an active layer acting as a current pathway between these electrodes and containing the polymer compound of the present invention, and a gate electrode controlling the quantity of current passing the current pathway, wherein the gate electrode is disposed in the active layer. Particularly, an organic transistor in which a source electrode, a drain electrode and the above-described gate electrode are disposed in contact with the above-described active layer is preferable.

The gate electrode may advantageously have a structure by which a current pathway flowing from a source electrode to a drain electrode can be formed and the quantity of current passing the current pathway can be controlled by voltage applied to the gate electrode, and for example, is a comb-shaped electrode.

The polymer compound of the present invention can be used a material of an organic field-effect transistor (OFET) sensor. In the OFET sensor of the present invention, an organic field-effect transistor is used as a signal conversion device in outputting an input signal as an electric signal, and sensitivity or selectivity is imparted to any one in a metal-insulation film-semiconductor structure. The OFET sensor of the present invention includes a biosensor, a gas sensor, an ion sensor, a humidity sensor, a pressure sensor and the like.

The biosensor has a substrate and an organic transistor disposed on the substrate, the above-described organic transistor has an organic semiconductor layer, a source region and a drain region disposed in contact with the above-described organic semiconductor, a channel region disposed in the above-described organic semiconductor layer and acting as a channel between the above-described source region and the above-described drain region, a gate electrode capable of applying electric filed on the above-described channel region, and a gate insulation film disposed between the above-described channel region and the above-described gate electrode, and a sensitive region as a probe specifically showing mutual action with a standard substance is disposed on the above-described channel region and/or the above-described gate insulation film, and when the concentration of the standard substance changes, a characteristic change occurs in the sensitive region, thus, the biosensor functions as a biosensor device.

As a method of detecting the standard substance in a specimen, a method of using a biosensor in which biomolecules such as nucleic acids, proteins and the like and artificially synthesized functional groups are fixed as a probe to the surface of a solid phase support is widely used.

In this method, the standard substance is captured to the surface of a solid phase support by utilizing specific affinity of biomolecules such as a mutual action of complementary nucleic acid chains, an antigen-antibody reaction, an enzyme-substrate reaction, a receptor-ligand mutual action and the like, therefore, a substance showing specific affinity with the standard substance is selected as a probe.

The probe is fixed to the surface of a solid phase support by a method suitable to the kinds of the probe and the solid phase support. Alternatively, it is also possible to synthesize a probe on the surface of a solid phase support (for example, nucleic acid elongating reaction and the like), and in any cases, the probe-fixed solid phase support surface is brought into contact with a specimen, and culturing is performed under suitable conditions, thus, a probe-standard substance complex is formed on the surface of the solid phase support. The above-described channel region and/or the above-described gate insulation film may itself function as a probe.

The gas sensor has a substrate and an organic transistor disposed on the substrate, and the above-described organic transistor has an organic semiconductor layer, a source region and a drain region disposed in contact with the above-described organic semiconductor, a channel region disposed in the above-described organic semiconductor layer and acting as a channel between the above-described source region and the above-described drain region, a gate electrode capable of applying electric field to the above-described channel region, and a gate insulation film disposed between the above-described channel region and the above-described gate electrode, and the above-described channel region and/or the above-described gate insulation film is used as a gas sensitive part, and when a gas is adsorbed to or desorbed from the channel region and/or the above-described gate insulation film, a characteristic change of electric conductivity, dielectric constant and the like occurs, thus, the gas sensor functions as a gas sensor device.

The gas to be detected includes an electron accepting gas and an electron donating gas.

Examples of the electron accepting gas include halogens such as $F_2$, $Cl_2$ and the like; nitrogen oxides; sulfur oxides; organic acids such as acetic acid and the like.

Examples of the electron donating gas include ammonia; amines such as aniline and the like; carbon monoxide; hydrogen, and the like.

The polymer compound of the present invention can be used in a pressure sensor. The pressure sensor has a substrate and an organic transistor disposed on the substrate, and the above-described organic transistor has an organic semiconductor layer, a source region and a drain region disposed in contact with the above-described organic semiconductor, a channel region disposed in the above-described organic semiconductor layer and acting as a channel between the above-described source region and the above-described drain region, a gate electrode capable of applying electric field to the above-described channel region, and a gate insulation film disposed between the above-described channel region and the above-described gate electrode, and the above-described channel region and/or the above-described gate insulation film is used as a pressure sensitive part, and when the pressure sensitive part senses pressure, a characteristic change occurs, thus, the pressure sensor functions as a pressure sensitive device.

When the gate insulation film is used as a pressure sensitive part, an organic material is preferable as a pressure sensitive part of a pressure sensor since organic materials are softer and have a higher stretching property than inorganic materials in general.

When the above-described channel region is used as a pressure sensitive part, an orientation layer may be provided for enhancing the crystallinity of an organic semiconductor. The orientation layer includes a monomolecular film and the like formed of a silane coupling agent such as hexamethyldisilazane and the like on a gate insulation film.

The polymer compound of the present invention can be used as a conductivity modulation sensor. The conductivity modulation sensor of the present invention is one using a conductivity measuring device as a signal conversion device in outputting an input signal as an electric signal, and sensitivity or selectivity against sensor target input is imparted to the above-described polymer compound or a covering film covered on at least a part of the above-described polymer compound, and input of a sensor target is detected as a change of conductivity of the above-described polymer compound, and the sensor includes a biosensor, a gas sensor, an ion sensor, a humidity sensor and the like.

The polymer compound of the present invention can be used in an amplifying circuit containing an organic field-effect transistor (OFET) for amplifying the output signal from various sensors such as a biosensor, a gas sensor, an ion sensor, a humidity sensor, a pressure sensor and the like separately formed.

The polymer compound of the present invention can be used as a sensor array containing a plurality of various sensors such as the above-described biosensor, gas sensor, ion sensor, humidity sensor, pressure sensor and the like.

The polymer compound of the present invention can also be used as an amplifying circuit-equipped sensor array containing a plurality of various sensors such as a biosensor, a gas sensor, an ion sensor, a humidity sensor, a pressure sensor and the like separately formed and containing as an amplifying circuit an organic field-effect transistor (OFET) for separately amplifying the output signal from each sensor.

EXAMPLES

Examples for illustrating the present invention further in detail are shown below, but the present invention is not limited to them.

(NMR Analysis)

NMR analysis was conducted using an NMR apparatus (manufactured by Varian, INOVA300). A measuring target compound was dissolved in deuterated chloroform to prepare a solution for measurement.

(Molecular Weight Analysis)

The number-average molecular weight and the weight-average molecular weight of a polymer compound were measured using gel permeation chromatography (GPC, manufactured by Waters, trade name: Alliance GPC 2000). The polymer compound to be measured was dissolved in orthodichlorobenzene, and the solution was injected into GPC.

As a mobile phase of GPC, orthodichlorobenzene was used. As the column, TSKgel GMHHR-H(S) HT was used (two columns were connected, manufactured by Tosoh Corp.). As the detector, an UV detector was used.

Synthesis Example 1

Synthesis of Compound 2

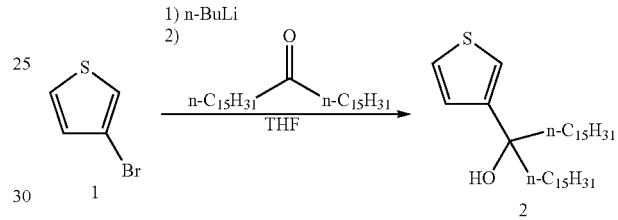

A nitrogen gas atmosphere was prepared in a reaction vessel, then, a compound 1 (16.0 g, 98.1 mmol) and dehydrated diethyl ether (280 mL) were added, and a uniform solution was made. While keeping the resultant solution at −68° C., a 1.65 M n-butyllithium hexane solution (65.4 mL, 0.108 mol) was dropped over a period of 10 minutes. Thereafter, the mixture was stirred at −68° C. for 5 hours. Thereafter, into this was added 16-hentriacontanone (48.7 g, 0.108 mol), and the mixture was stirred at −78° C. for 10 minutes, then, stirred at room temperature (25° C.) for 5 hours. Thereafter, water (200 mL) was added to this to stop the reaction, and a 10 wt % acetic acid aqueous solution was added to render the reaction solution acidic. Thereafter, the reaction product was extracted using hexane. The resultant organic layer was washed with water, dried over anhydrous magnesium sulfate and filtrated. The resultant filtrate was concentrated by an evaporator, then, the solvent was distilled off to obtain 70 g of a compound 2. The yield was 100%.

$^1$H-NMR (300 MHz, CDCl$_3$): δ (ppm)=0.879 (t, 6H), 1.253 (m, 52H), 1.746 (m, 4H), 6.960 (d, 1H), 7.266 (d, 1H).

Synthesis Example 2

Synthesis of Compound 3

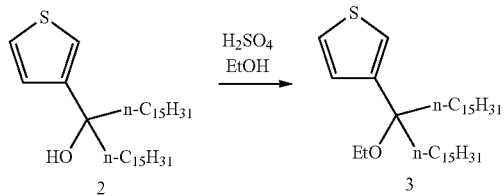

A nitrogen gas atmosphere was prepared in a reaction vessel, then, a compound 2 (53 g, 98 mmol) and dehydrated ethanol (500 mL) were added, and a suspension was formed.

To the resultant suspension was added 96 wt % concentrated sulfuric acid (3.0 mL, 56 mmol), then, the mixture was stirred at room temperature for 3 hours. Thereafter, water (200 mL) was added to this to stop the reaction, and the reaction product was extracted using hexane. The resultant organic layer was washed with water, dried over anhydrous magnesium sulfate and filtrated. The resultant filtrate was concentrated by an evaporator, then, the solvent was distilled off. The resultant residue was purified by silica gel column chromatography using hexane as a mobile phase, to obtain 20.7 g of a compound 3.

The yield was 37%.

$^1$H-NMR (300 MHz, CDCl$_3$): δ (ppm)=0.88 (t, 6H), 1.13 (t, 3H), 1.24 (m, 52H), 1.77 (m, 4H), 3.15 (q, 2H), 7.05 (m, 2H), 7.24 (d, 1H).

Synthesis Example 3

Synthesis of Compound 4

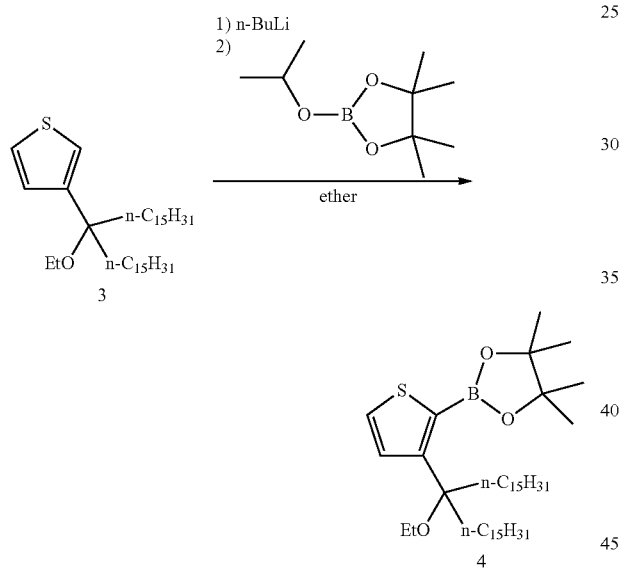

A nitrogen gas atmosphere was prepared in a reaction vessel, then, a compound 3 (2.0 g, 3.6 mmol) and dehydrated diethyl ether (35 mL) were added, and a uniform solution was made. While keeping the resultant solution at −68° C., a 1.65 M n-butyllithium hexane solution (2.3 mL, 3.7 mol) was dropped over a period of 10 minutes. Thereafter, the mixture was stirred at −68° C. for 10 minutes, then, stirred at room temperature (25° C.) for 1.5 hours. Thereafter, while keeping the resultant solution at −68° C., 2-isopropoxy-4,4,5,5-tetramethyl-1,3,2-dioxaborolane (0.69 g, 3.7 mmol) was added. Thereafter, the mixture was stirred at −68° C. for 10 minutes, then, stirred at room temperature (25° C.) for 2 hours. Thereafter, water (100 mL) was added to this to stop the reaction, and the reaction product was extracted using diethyl ether. The resultant organic layer was washed with water, dried over anhydrous magnesium sulfate and filtrated. The resultant filtrate was concentrated by an evaporator, then, the solvent was distilled off, to obtain 2.45 g of a compound 4. The yield was 100%.

$^1$H-NMR (300 MHz, CDCl$_3$): δ (ppm)=1.335 (s, 12H), 1.989 (m, 4H), 3.224 (q, 2H), 7.264 (d, 1H), 7.422 (d, 1H).

Synthesis Example 4

Synthesis of Compound 5

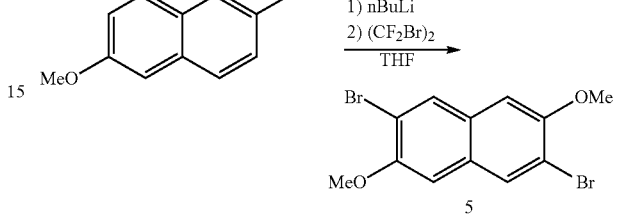

A nitrogen gas atmosphere was prepared in a reaction vessel, then, 2,6-dimethoxynaphthalene (4.00 g, 32.2 mmol) and dehydrated THF (200 mL) were added, and a uniform solution was made. Thereafter, a 1.65 M n-butyllithium hexane solution (52 mL, 85 mmol) was dropped into this over a period of 30 minutes, and the mixture was stirred at room temperature for 78 hours. Thereafter, to this was added 1,2-dibromo-1,1,2,2-tetrafluoroethane (22 g, 85 mmol), and the mixture was stirred at room temperature (25° C.) for 2 hours. Thereafter, water (200 mL) was added to this to stop the reaction, and the reaction product was extracted using chloroform. The resultant organic layer was washed with water, dried over anhydrous magnesium sulfate and filtrated. The resultant filtrate was concentrated by an evaporator, then, the solvent was distilled off. The resultant residue was crystallized using a mixed solvent of chloroform and methanol, to obtain 5.43 g of a compound 5. The yield was 73%.

$^1$H-NMR (300 MHz, CDCl$_3$): δ (ppm)=7.02 (s, 2H), 7.94 (s, 2H).

Synthesis Example 5

Synthesis of Compound 6

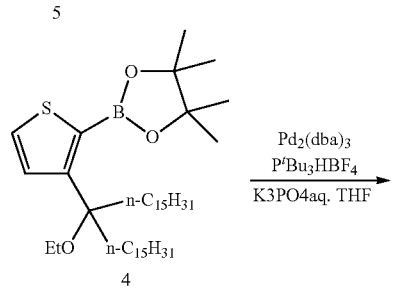

-continued

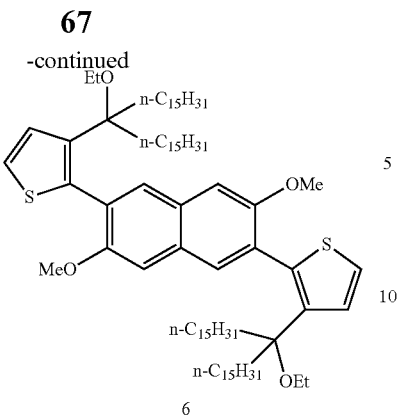

6

A nitrogen gas atmosphere was prepared in a reaction vessel equipped with a reflux tube, then, a compound 5 (4.20 g, 12.1 mmol) and dry THF (360 mL) were added, and the mixture was deaerated for 30 minutes by argon bubbling. Thereafter, to this were added tris(dibenzylideneacetone)dipalladium(0) (556 mg, 0.607 mmol), tri-tert-butylphosphonium tetrafluoroborate (739 mg, 2.43 mmol) and a 3 M potassium phosphate aqueous solution (60 mL, 0.180 mol), and the mixture was heated at 80° C. Thereafter, a dry THF (30 mL) solution of a compound 4 (33.45 g, 48.6 mmol) deaerated for 30 minutes by argon bubbling was dropped into this at 80° C. over a period of 5 minutes, and the mixture was stirred at the same temperature for 4.5 hours.

Thereafter, the reaction product was extracted using hexane (200 mL). The resultant organic layer was washed with saturated saline, dried over anhydrous magnesium sulfate and filtrated. The resultant filtrate was concentrated by an evaporator, then, the solvent was distilled off. The resultant residue was purified by silica gel column chromatography using a mixed solvent of hexane and chloroform as a mobile phase, to obtain 7.3 g of a compound 6. The yield was 46%.

$^1$H-NMR (300 MHz, CDCl$_3$): δ (ppm)=0.88 (t, 12H), 0.98 (t, 6H), 1.24 (m, 104H), 1.56 (m, 8H), 3.22 (q, 4H), 3.78 (s, 6H), 7.15 (d, 2H), 7.28 (d, 2H), 7.36 (d, 2H), 7.85 (d, 2H).

Example 1

Synthesis of Compound 7

-continued

7

A nitrogen gas atmosphere was prepared in a reaction vessel, then, a compound 6 (4.73 g, 3.61 mmol) and dry methylene chloride (120 mL) were added. Thereafter, to this was added a 1 M boron tribromide methylene chloride solution (14.4 mL, 14.4 mmol) at −50° C., and the mixture was stirred at −50° C. for 4 hours. Thereafter, to this was added water at −50° C., and the temperature was raised up to room temperature, then, the reaction product was extracted using chloroform. The resultant organic layer was washed with water, dried over anhydrous magnesium sulfate and filtrated. The resultant filtrate was concentrated by an evaporator, then, the solvent was distilled off. The resultant residue was purified by silica gel column chromatography using hexane as a mobile phase, to obtain 2.33 g of a compound 7. The yield was 53%.

$^1$H-NMR (300 MHz, CDCl$_3$): δ (ppm)=0.88 (t, 12H), 1.24 (m, 104H), 2.26 (m, 8H), 4.10 (s, 6H), 7.03 (d, 2H), 7.35 (d, 2H).

Example 2

Synthesis of Compound 8

8

A nitrogen gas atmosphere was prepared in a reaction vessel, then, a compound 7 (2.66 g, 2.18 mmol) and dry THF (220 mL) were added. Thereafter, to this was added N-bromosuccinimide (0.855 g, 4.80 mmol) at room temperature, and the mixture was stirred for 3 hours at room temperature. Thereafter, to this were added a saturated sodium thiosulfate aqueous solution (2 mL) and water (100 mL), and the mixture was stirred for 5 minutes, then, the reaction product was extracted using hexane. The resultant organic layer was washed with water, dried over anhydrous magnesium sulfate and filtrated. The resultant filtrate was concentrated by an evaporator, then, the solvent was distilled off. The resultant residue was purified by silica gel column chromatography using hexane as a mobile phase, and recrystallized using a mixed solvent of hexane and methanol, to obtain 0.67 g of a compound 8. The yield was 22%.

$^1$H-NMR (300 MHz, CDCl$_3$): δ (ppm)=0.85 (t, 12H), 1.24 (m, 104H), 2.16 (m, 8H), 4.08 (s, 6H), 7.04 (s, 2H), 7.25 (s, 2H).

Example 3

Synthesis of Polymer Compound A

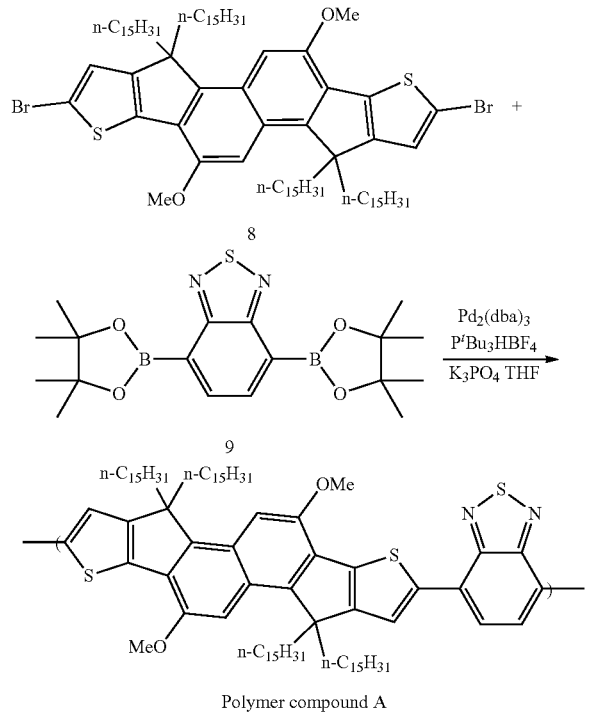

Polymer compound A

A nitrogen gas atmosphere was prepared in a reaction vessel equipped with a reflux tube, then, a compound 8 (137.6 mg, 0.1 mmol) and dry THF (3.5 mL) were added, and the mixture was deaerated for 30 minutes by argon gas bubbling. Thereafter, to this were added tris(dibenzylideneacetone)dipalladium(0) (4.58 mg, 5 μmol), tri-tert-butylphosphonium tetrafluoroborate (5.80 mg, 20 μmol) and, a 3 M potassium phosphate aqueous solution (0.5 mL, 1.5 mmol) deaerated for 30 minutes by argon bubbling. The resultant reaction solution was heated up to 80° C., then, a dry THF solution (2.5 mL) of a compound 9 (38.8 mg, 1 mmol) deaerated for 30 minutes by argon gas bubbling was dropped, then, the mixture was stirred at 80° C. for 3 hours. Thereafter, to this was added an o-chlorobenzene solution (8 mL) of phenylboric acid (10 mg, 0.082 mmol) deaerated for 30 minutes by argon bubbling, and the mixture was stirred at 80° C. for 1.5 hours. Thereafter, to this were added sodium N,N-diethyldithiocarbamate tri-hydrate (0.8 g) and water (7.5 g), and the mixture was stirred at 80° C. for 3 hours. The organic layer was separated from the resultant reaction solution, then, the resultant organic layer was washed with water and a 10 wt % acetic acid aqueous solution. The resultant organic layer was dropped into acetone (104 mL), to obtain a deposit. The resultant deposit was purified by a silica gel column using o-dichlorobenzene as a developing solvent, then, the resultant o-dichlorobenzene solution was poured into methanol, to obtain a solid. The resultant solid was filtrated, and washed by a Soxhlet apparatus using acetone as a solvent and dried, to obtain 34.0 mg of a polymer compound A.

The resultant polymer compound A had a polystyrene-equivalent number-average molecular weight of $1.7 \times 10^4$ and a weight-average molecular weight of $5.0 \times 10^4$.

Example 4

Synthesis of Polymer Compound B

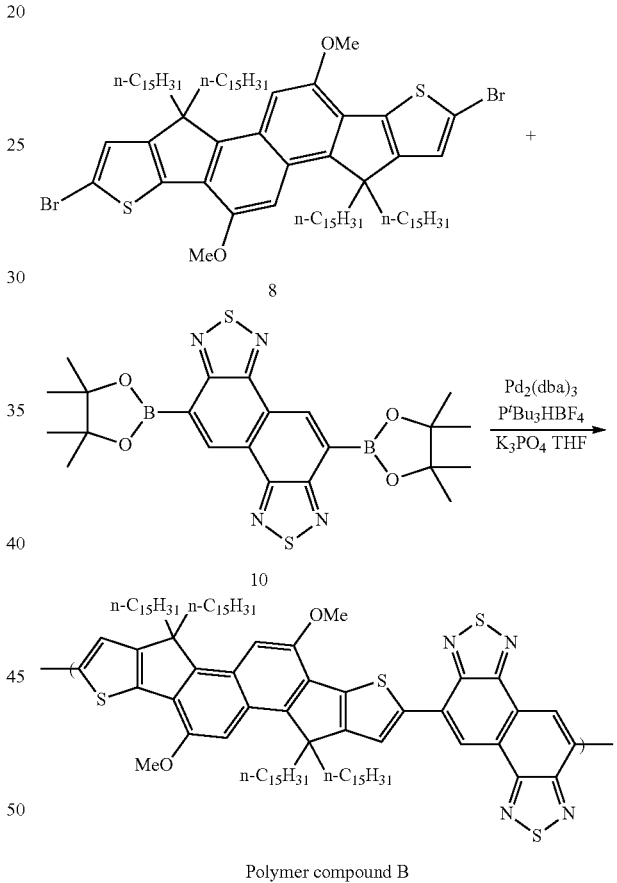

Polymer compound B

A nitrogen gas atmosphere was prepared in a reaction vessel equipped with a reflux tube, then, a compound 8 (137.6 mg, 0.1 mmol) and dry THF (10 mL) were added, and the mixture was deaerated for 30 minutes by argon gas bubbling. Thereafter, to this were added tris(dibenzylideneacetone)dipalladium(0) (4.58 mg, 5 μmol), tri-tert-butylphosphonium tetrafluoroborate (5.80 mg, 20 μmol) and, a 3 M potassium phosphate aqueous solution (0.5 mL, 1.5 mmol) deaerated for 30 minutes by argon gas bubbling. The resultant reaction solution was heated up to 80° C., then, a compound 10 (49.6 mg, 1.0 mmol) was added, and the mixture was stirred at 80° C. for 3 hours. Thereafter, an o-chlorobenzene solution (8 mL) of phenylboric acid (10 mg, 0.082 mmol) deaerated for 30 minutes by argon gas bubbling was added to this, and the mixture was stirred at 80° C. for 1.5 hours. Thereafter, to this were added sodium N,N-diethyldithiocarbamate tri-hydrate (0.8 g) and water (7.5 g), and the mixture was stirred at 80° C. for 3 hours. The organic layer was separated from the resultant reaction solution, then, the resultant organic layer was washed with water and a 10 wt % acetic acid aqueous solution. The resultant organic layer was dropped into acetone (104 mL), to obtain a deposit. The resultant deposit was purified by a silica gel column using o-dichlorobenzene as a developing solvent, then, the resultant o-dichlorobenzene solution was poured into methanol, to obtain a solid. The resultant solid was filtrated, washed by a Soxhlet apparatus using acetone as a solvent and dried, to obtain 50.8 mg of a polymer compound B.

The resultant polymer compound B had a polystyrene-equivalent number-average molecular weight of $1.1 \times 10^4$ and a weight-average molecular weight of $2.2 \times 10^4$.

Comparative Example 1

Synthesis of Polymer Compound C

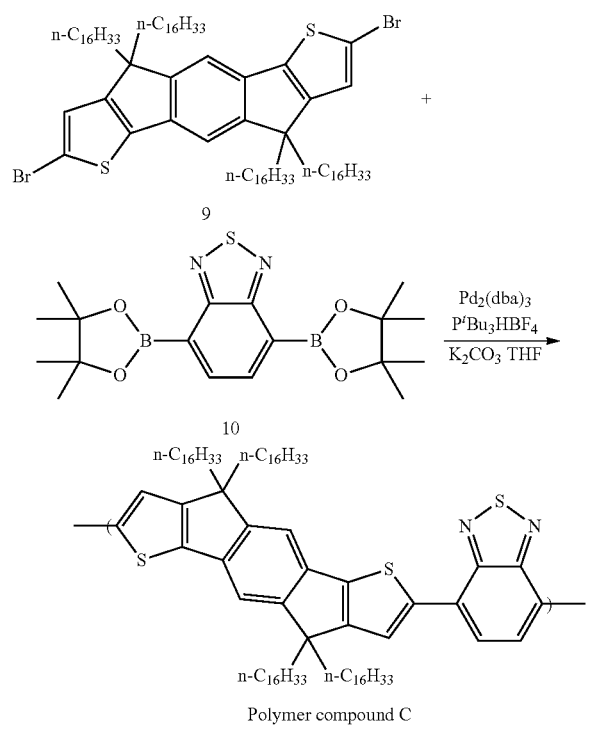

Polymer compound C

A nitrogen gas atmosphere was prepared in a reaction vessel, then, a compound 10 (0.300 g, 0.227 mmol), a compound 9 (0.0881 g, 0.227 mmol) synthesized according to a method described in "J. Am. Chem. Soc., 2010, 132, 11437-11439", tetrahydrofuran (30 mL), tris(dibenzylideneacetone)dipalladium (4.2 mg) and tri-tert-butylphosphonium tetrafluoroborate (5.3 mg) were added, and the mixture was stirred. Thereafter, a 2 mol/L potassium carbonate aqueous solution (1.13 mL) was dropped into this, and the mixture was refluxed for 5 hours. Thereafter, to this was added phenylboronic acid (10.0 mg), and the mixture was refluxed for 1 hour. Thereafter, to this was added sodium N,N-diethyldithiocarbamate tri-hydrate (0.1 g), and the mixture was refluxed for 3 hours. The resultant reaction solution was poured into water, toluene was added, and the toluene layer was extracted. The resultant toluene solution was washed with an acetic acid aqueous solution and water, then, purified by using a silica gel column. The resultant toluene solution was dropped into acetone, to obtain a deposit. The resultant deposit was washed by a Soxhlet extractor using acetone as a solvent, to obtain a polymer compound C. The gained amount was 270 mg, and the polystyrene-equivalent number-average molecular weight was $3.0 \times 10^4$ and the weight-average molecular weight was $1.1 \times 10^5$.

Example 5

Fabrication and Evaluation of Organic Film Solar Battery 1

The polymer compound A and an electron accepting compound fullerene C60PCBM (phenyl C61-butyric acid methyl ester) (Phenyl C61-butyric acid methyl ester, manufactured by Frontier Carbon Corporation) were dissolved in orthodichlorobenzene at a weight ratio of polymer compound A/C60PCBM=2/1, and the resultant solution was filtrated through a Teflon (registered trademark) filter having a pore diameter of 0.45 μm, to prepared an ink 1 (sum of polymer compound A and C60PCBM was 2.25 wt %).

A glass substrate carrying thereon a patterning of ITO having a thickness of about 150 nm formed by a sputtering method was washed with an organic solvent, an alkali detergent and ultrapure water, and dried. Thereafter, the glass substrate was treated with ultraviolet-ozone (UV-$O_3$) using an ultraviolet-ozone (UV-$O_3$) apparatus.

Next, a PEDOT:PSS solution (CleviosP VP AI4083 manufactured by Heraeus) was filtrated through a filter having a pore diameter of 0.45 μm. The PEDOT:PSS solution after filtration was spin-coated on the ITO side of the substrate to form a film having a thickness of 50 nm. Thereafter, by heating on a hot plate at 120° C. for 10 minutes in atmosphere, an organic layer functioning as a hole transporting layer was formed.

Next, the above-described ink 1 was spin-coated on the organic layer of the substrate to form an active layer having a thickness of 100 nm.

Next, calcium was vapor-deposited with a thickness of 4 nm, then, aluminum was vapor-deposited with a thickness of 100 nm by a vacuum vapor depositing machine, to fabricate an organic film solar battery 1 as a photoelectric conversion device. The degree of vacuum in metal vapor deposition was $1.0 \times 10^{-3}$ to $9 \times 10^{-3}$ Pa. The resultant organic film solar battery 1 was in the form of 2 mm×2 mm square.

The organic solar battery 1 obtained above was irradiated with a constant light using Solar Simulator (manufactured by BUNKOUKEIKI Co., Ltd., trade name: OTENTO-SUNII: AM 1.5 G filter, irradiance 100 mW/cm$^2$), and the generating current and voltage were measured and photoelectric conversion efficiency, short circuit current density, open voltage and fill factor were calculated. Jsc (short circuit current density) was 6.16 mA/cm$^2$, Voc (open end voltage) was 0.848 V, ff (fill factor) was 0.677 and photoelectric conversion efficiency (η) was 3.53%. The results are shown in Table 1.

Example 6

Fabrication and Evaluation of Organic Film Solar Battery 2

An ink 2 was prepared and an organic film solar battery 2 was fabricated and evaluated in the same manner as in Example 5 excepting that the polymer compound B was used instead of the polymer compound A. Jsc (short circuit current density) was 6.97 mA/cm², Voc (open end voltage) was 0.757 V, ff (fill factor) was 0.680 and photoelectric conversion efficiency (η) was 3.60%. The results are shown in Table 1.

Comparative Example 2

Fabrication and Evaluation of Organic Film Solar Battery 3

An ink 3 was prepared and an organic film solar battery 3 was fabricated and evaluated in the same manner as in Example 5 excepting that the polymer compound C was used instead of the polymer compound A. Jsc (short circuit current density) was 3.23 mA/cm², Voc (open end voltage) was 0.790 V, ff (fill factor) was 0.559 and photoelectric conversion efficiency (η) was 1.42%. The results are shown in Table 1.

Synthesis Example 6

Synthesis of Compound 12

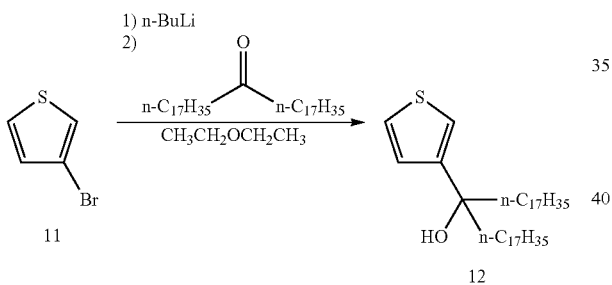

A nitrogen gas atmosphere was prepared in a reaction vessel, then, a compound 11 (32 g, 0.20 mol) and dehydrated diethyl ether (470 mL) were added, and a uniform solution was made. While keeping the resultant solution at −68° C., a 1.60 M n-butyllithium hexane solution (135 mL, 0.22 mol) was dropped over a period of 30 minutes. Thereafter, the mixture was stirred at −68° C. for 2 hours. Thereafter, to this was added 18-hentriacontanone (69.7 g, 0.14 mol), and the mixture was stirred at −78° C. for 10 minutes, then, stirred at room temperature (25° C.) for 5 hours. Thereafter, water (200 mL) was added to this to stop the reaction, and a 10 wt % acetic acid aqueous solution was added to render the reaction solution acidic. Thereafter, the reaction product was extracted using hexane. The resultant organic layer was washed with water, dried over anhydrous magnesium sulfate and filtrated. The resultant filtrate was concentrated by an evaporator, then, the solvent was distilled off to obtain, 125 g of a compound 12. The yield was 100%.

¹H-NMR (300 MHz, CDCl₃): δ (ppm)=0.88 (t, 6H), 1.25 (m, 60H), 1.75 (m, 4H), 6.96 (d, 1H), 7.27 (d, 1H).

Synthesis Example 7

Synthesis of Compound 13

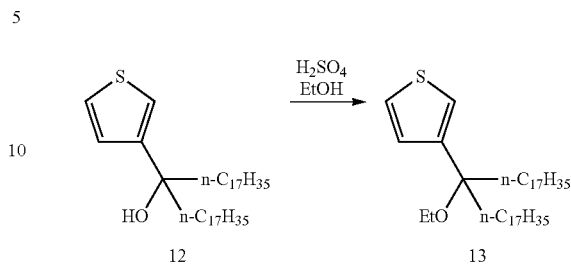

A nitrogen gas atmosphere was prepared in a reaction vessel, then, a compound 12 (232 g, 0.39 mol) and dehydrated ethanol (880 mL) and hexane (350 mL) were added, and a suspension was formed. To the resultant suspension was added 96 wt % concentrated sulfuric acid (31 mL, 0.59 mol), then, the mixture was stirred at room temperature for 6 hours. Thereafter, water (200 mL) was added to this to stop the reaction, and the reaction product was extracted using hexane. The resultant organic layer was washed with water, dried over anhydrous magnesium sulfate and filtrated. The resultant filtrate was concentrated by an evaporator, then, the solvent was distilled off. The resultant residue was purified by silica gel column chromatography using hexane as a mobile phase, to obtain 104 g of a compound 13. The yield was 43%.

¹H-NMR (300 MHz, CDCl₃): δ (ppm)=0.88 (t, 6H), 1.13 (t, 3H), 1.24 (m, 60H), 1.77 (m, 4H), 3.15 (q, 2H), 7.05 (m, 2H), 7.24 (d, 1H).

Synthesis Example 8

Synthesis of Compound 14

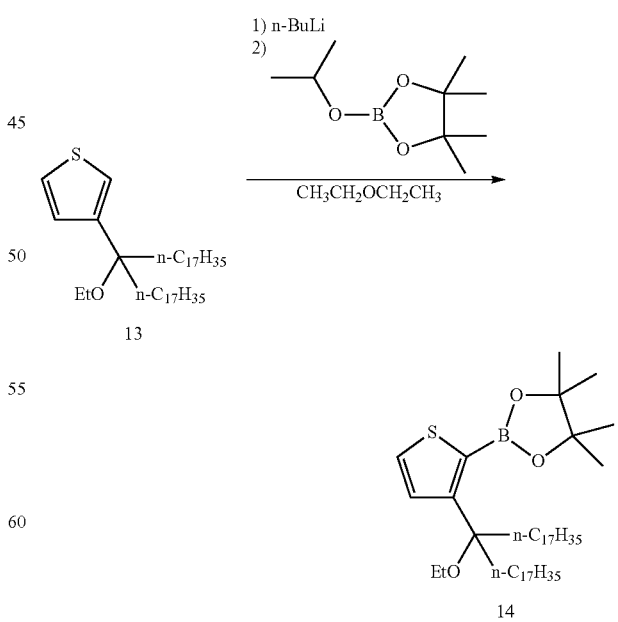

A nitrogen gas atmosphere was prepared in a reaction vessel, then, a compound 13 (104 g, 0.17 mol) and dehydrated diethyl ether (1020 mL) were added, and a uniform solution was made. While keeping the resultant solution at −68° C., a 1.60 M n-butyllithium hexane solution (136 mL, 0.22 mol) was dropped over a period of 10 minutes. Thereafter, the mixture was stirred at −68° C. for 10 minutes, then, mixed at room temperature (25° C.) for 1.5 hours. Thereafter, while keeping the resultant solution at −68° C., 2-isopropoxy-4,4,5,5-tetramethyl-1,3,2-dioxaborolane (62.5 g, 0.34 mmol) was added. Thereafter, the mixture was stirred at −68° C. for 10 minutes, then, stirred at room temperature (25° C.) for 2 hours. Thereafter, water (100 mL) was added to this to stop the reaction, and the reaction product was extracted using diethyl ether. The resultant organic layer was washed with water, dried over anhydrous magnesium sulfate and filtrated. The resultant filtrate was concentrated by an evaporator, then, the solvent was distilled off to obtain, 117 g of a compound 14. The yield was 93%.

$^1$H-NMR (300 MHz, CDCl$_3$): δ (ppm)=1.34 (s, 12H), 1.99 (m, 4H), 3.22 (q, 2H), 7.26 (d, 1H), 7.42 (d, 1H).

Synthesis Example 9

Synthesis of Compound 15

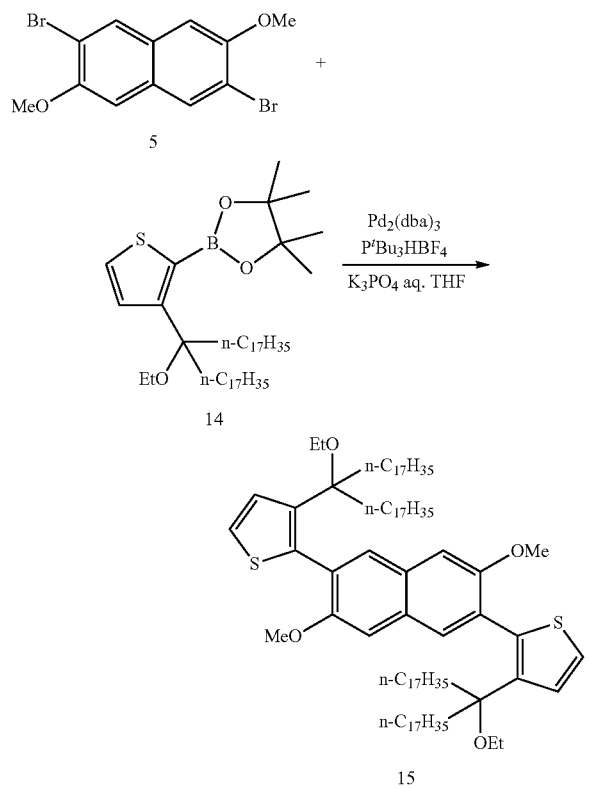

A nitrogen gas atmosphere was prepared in a reaction vessel equipped with a reflux tube, then, a compound 5 (17.6 g, 50.84 mmol) and dry THF (388 mL) were added, and the mixture was deaerated for 30 minutes by argon bubbling. Thereafter, to this were added tris(dibenzylideneacetone)dipalladium(0) (470 mg, 0.51 mmol), tri-tert-butylphosphonium tetrafluoroborate (700 mg, 2.03 mmol) and a 3 M potassium phosphate aqueous solution (187 mL, 0.560 mol), and the mixture was heated at 80° C. Thereafter, a dry THF (13 mL) solution of a compound 14 (96.6 g, 127 mmol) deaerated for 30 minutes by argon bubbling was dropped into this at 80° C. over a period of 5 minutes, and the mixture was stirred at the same temperature for 4.5 hours.

Thereafter, the reaction product was extracted using hexane (200 mL). The resultant organic layer was washed with saturated saline, dried over anhydrous magnesium sulfate and filtrated. The resultant filtrate was concentrated by an evaporator, then, the solvent was distilled off. The resultant residue was purified by silica gel column chromatography using a mixed solvent of hexane and chloroform as a mobile phase, to obtain 27 g of a compound 15. The yield was 37%.

$^1$H-NMR (300 MHz, CDCl$_3$): δ (ppm)=0.88 (t, 12H), 0.98 (t, 6H), 1.24 (m, 120H), 1.56 (m, 8H), 3.22 (q, 4H), 3.78 (s, 6H), 7.15 (d, 2H), 7.28 (d, 2H), 7.36 (d, 2H), 7.85 (d, 2H).

Example 7

Synthesis of Compound 16

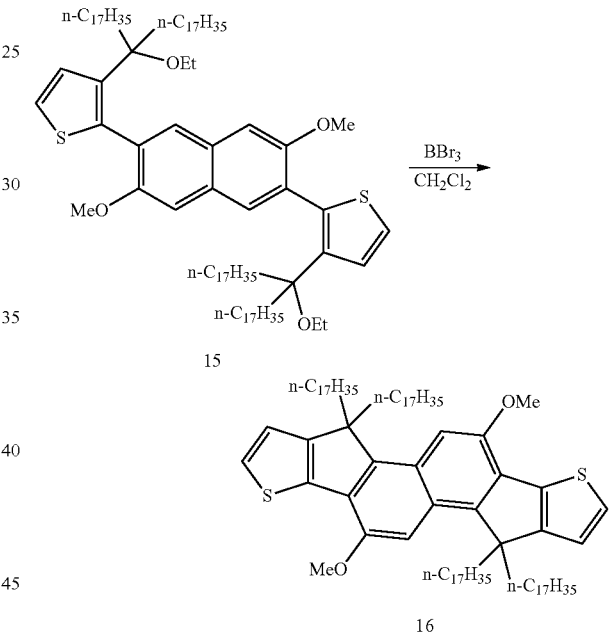

A nitrogen gas atmosphere was prepared in a reaction vessel, then, a compound 15 (24.8 g, 17.4 mmol) and dry methylene chloride (420 mL) were added. Thereafter, to this was added a 1 M boron tribromide methylene chloride solution (69.8 mL, 69.7 mmol) at −10° C., and the mixture was heated up to room temperature, then, stirred at room temperature for 1 hour. Thereafter, water was added to this, and the reaction product was extracted using chloroform. The resultant organic layer was washed with water, dried over anhydrous magnesium sulfate and filtrated. The resultant filtrate was concentrated by an evaporator, then, the solvent was distilled off. The resultant residue was purified by silica gel column chromatography using hexane as a mobile phase, to obtain 17.8 g of a compound 16. The yield was 77%.

$^1$H-NMR (300 MHz, CDCl$_3$): δ (ppm)=0.88 (t, 12H), 1.24 (m, 120H), 2.26 (m, 8H), 4.10 (s, 6H), 7.03 (d, 2H), 7.35 (d, 2H).

Example 8

Synthesis of Compound 17

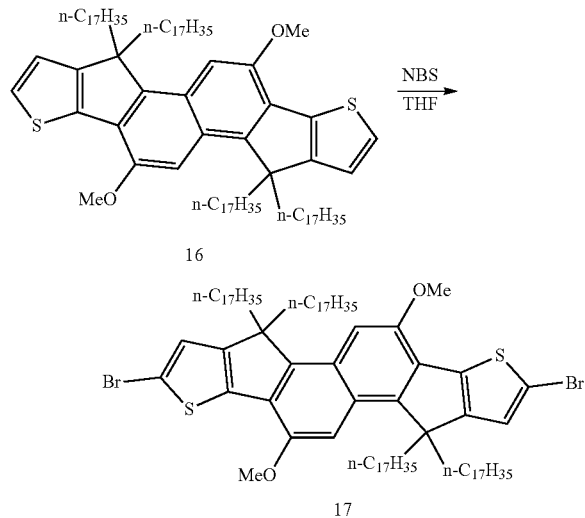

A nitrogen gas atmosphere was prepared in a reaction vessel, then, a compound 16 (17.9 g, 14.7 mmol) and dry THF (700 mL) were added. Thereafter, to this was added N-bromosuccinimide (5.41 g, 32.2 mmol) at room temperature, and the mixture was stirred for 3 hours at room temperature. Thereafter, to this were added a saturated sodium thiosulfate aqueous solution (10 mL) and water (200 mL), and the mixture was stirred for 5 minutes, then, the reaction product was extracted using hexane. The resultant organic layer was washed with water, dried over anhydrous magnesium sulfate and filtrated. The resultant filtrate was concentrated by an evaporator, then, the solvent was distilled off. The resultant residue was purified by silica gel column chromatography using hexane as a mobile phase, and recrystallized using hexane, to obtain 18.1 g of a compound 17. The yield was 90.

$^1$H-NMR (300 MHz, CDCl$_3$): δ (ppm)=0.85 (t, 12H), 1.24 (m, 120H), 2.16 (m, 8H), 4.08 (s, 6H), 7.04 (s, 2H), 7.25 (s, 2H).

Example 9

Synthesis of Compound 18

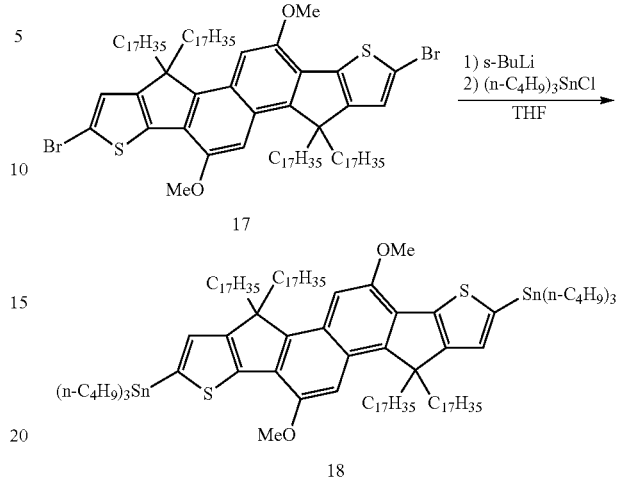

A nitrogen gas atmosphere was prepared in a reaction vessel, then, dehydrated THF (147 mL, 93.9 mmol) was added, and the mixture was cooled down to −65° C. Thereafter, to this was added a 1 M sec-butyllithium hexane solution (8.06 mL, 8.06 mmol), and the mixture was stirred at −65° C. for 0.5 hours, then, a compound 17 (2.0 g, 1.34 mmol) was added, and the mixture was stirred at −50° C. for 1 hours. To this was added tributyltin chloride (2.62 g, 8.06 mmol), and the mixture was heated up to room temperature. After stirring for 2 hours, water (20 mL) was added to stop the reaction, and the reaction product was extracted using toluene. The resultant organic layer was washed with water, dried over anhydrous magnesium sulfate and filtrated. The resultant filtrate was concentrated by an evaporator, then, the solvent was distilled off. The resultant residue was purified by ODS column chromatography using a THF-acetonitrile mixed solvent as a mobile phase, to obtain 2.4 g of a compound 16. The yield was 95%.

$^1$H-NMR (300 MHz, CDCl$_3$): δ (ppm)=7.31 (s, 2H), 7.06 (s, 2H), 4.09 (s, 6H), 2.20 (m, 8H), 1.20 (m, 156H), 0.88 (m, 30H)

Example 10

Synthesis of Polymer Compound D

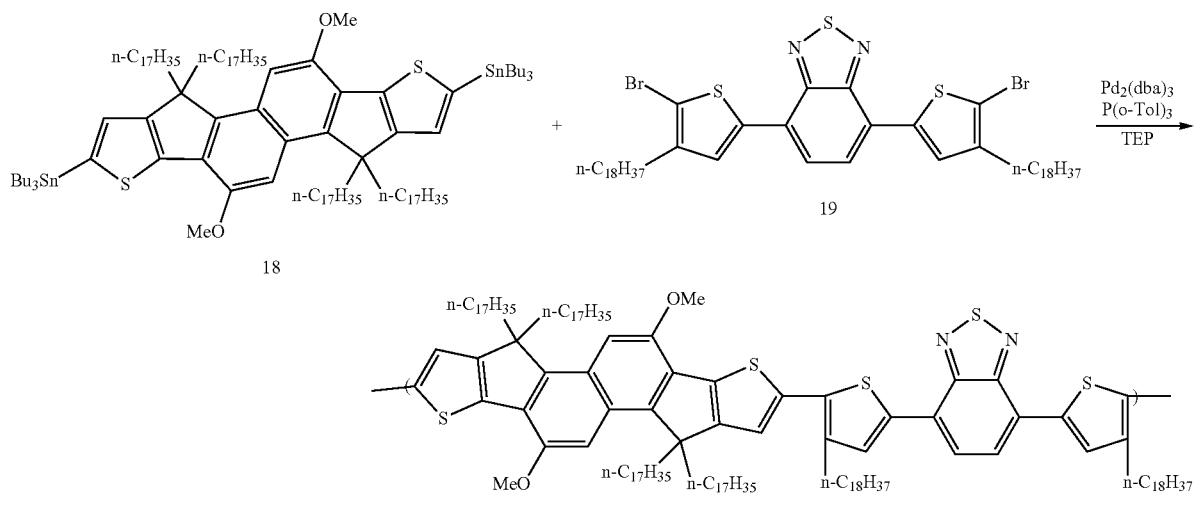

Polymer compound D

A gas in a 100 mL three-necked flask equipped with a reflux tube was purged with a nitrogen gas, then, a compound 18 (194.4 mg, 0.10 mmol), a compound 19 (98.1 mg, 0.10 mmol) synthesized by a method described in a non-patent document Journal of Polymer Science Part A: Polymer Chemistry, Vol 49, 3852-3862 (2011) and dry toluene (10 mL) were added, and the mixture was deaerated for 30 minutes by bubbling with an argon gas. Tris(dibenzylideneacetone)dipalladium(0) (3.7 mg) and tris(o-toluyl)phosphine (5.0 mg) were added, and the mixture was stirred at 110° C. for 3 hours. Thereafter, to the resultant mixed solution were added tris(dibenzylideneacetone)dipalladium(0) (3.7 mg), tris(o-toluyl)phosphine (5.0 mg) and a toluene solution (4.2 mL) of phenyl bromide (160 mg) deaerated by bubbling for 30 minutes with an argon gas, and the mixture was stirred at 110° C. for 1 hour, and sodium N,N-diethyldithiocarbamate tri-hydrate (0.8 g) and water (7.6 g) were added, and the mixture was stirred at 110° C. for 1 hour. The resultant reaction solution was allowed to stand still, and the separated organic layer was washed with water and a 10 wt % acetic acid aqueous solution. Thereafter, the separated organic layer was dropped into acetone (43 mL), to obtain a deposit. The resultant deposit was purified by a silica gel column using toluene as a developing solvent, thereafter, the resultant toluene solution was poured into methanol (84 mL), to deposit a solid, and the resultant solid was filtrated. Using a Soxhlet extractor, the resultant solid was washed with acetone for 3 hours and dried, to obtain 194 mg of a compound 14. The resultant polymer compound D had a polystyrene-equivalent number-average molecular weight of $3.0 \times 10^4$ and a weight-average molecular weight of $5.4 \times 10^4$.

Example 11

Synthesis of Polymer Compound E

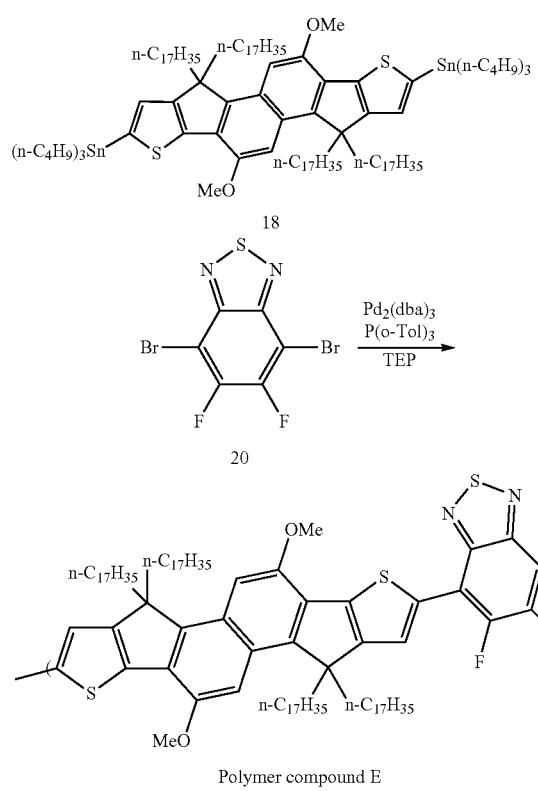

Polymer compound E

A gas in a 100 mL three-necked flask equipped with a reflux tube was purged with a nitrogen gas, then, a compound 12 (194.4 mg, 0.10 mmol), a compound 13 (33.0 mg, 0.10 mmol) synthesized by a method described in a patent document WO2012/169605A1 and dry toluene (10 mL) were added, and the mixture was deaerated for 30 minutes by bubbling with an argon gas. Tris(dibenzylideneacetone)dipalladium(0) (3.7 mg) and tris(o-toluyl)phosphine (5.0 mg) were added, and the mixture was stirred at 110° C. for 3 hours. Thereafter, to the resultant mixed solution were added tris(dibenzylideneacetone)dipalladium(0) (3.7 mg) and tris(o-toluyl)phosphine (5.0 mg), and a toluene solution (4.2 mL) of phenyl bromide (160 mg) deaerated by bubbling for 30 minutes with an argon gas, and the mixture was stirred at 110° C. for 1 hour, and sodium N,N-diethyldithiocarbamate tri-hydrate (0.8 g) and water (7.6 g) were added, and the mixture was stirred at 110° C. for 1 hour. The resultant reaction solution was allowed to stand still, and the separated organic layer was washed with water and a 10 wt % acetic acid aqueous solution. Thereafter, the separated organic layer was dropped into acetone (43 mL), to obtain a deposit. The resultant deposit was purified by a silica gel column using toluene as a developing solvent, thereafter, the resultant toluene solution was poured into methanol (84 mL), to deposit a solid, and the resultant solid was filtrated. Using a Soxhlet extractor, the resultant solid was washed with acetone for 3 hours and dried, to obtain 162 mg of a polymer compound E. The resultant polymer compound E had a polystyrene-equivalent number-average molecular weight of $1.3 \times 10^4$ and a weight-average molecular weight of $2.9 \times 10^4$.

Example 12

Synthesis of Polymer Compound F

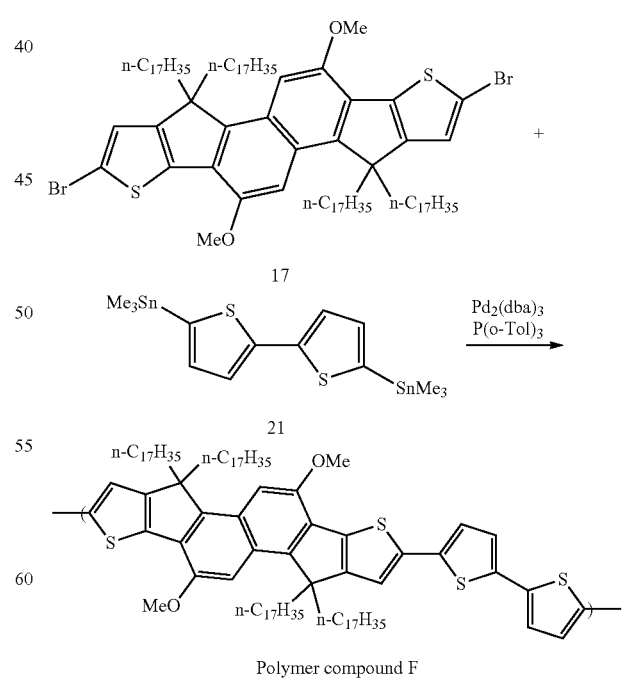

Polymer compound F

A gas in a 100 mL three-necked flask equipped with a reflux tube was purged with a nitrogen gas, then, a compound 12 (194.4 mg, 0.10 mmol), a compound 13 (98.1 mg, 0.10 mmol) and dry toluene (10 mL) were added, and the mixture was deaerated for 30 minutes by bubbling with an argon gas. Tris(dibenzylideneacetone)dipalladium(0) (3.7 mg) and tris(o-toluyl)phosphine (5.0 mg) were added, and the mixture was stirred at 110° C. for 3 hours. Thereafter, to the resultant mixed solution were added tris(dibenzylideneacetone)dipalladium(0) (3.7 mg) and tris(o-toluyl)phosphine (5.0 mg), and a toluene solution (4.2 mL) of phenyl bromide (160 mg) deaerated by bubbling for 30 minutes with an argon gas, and the mixture was stirred at 110° C. for 1 hour, and sodium N,N-diethyldithiocarbamate tri-hydrate (0.8 g) and water (7.6 g) were added, and the mixture was stirred at 110° C. for 1 hour. The resultant reaction solution was allowed to stand still, and the separated organic layer was washed with water and a 10 wt % acetic acid aqueous solution. Thereafter, the separated organic layer was dropped into acetone (43 mL), to obtain a deposit. The resultant deposit was purified by a silica gel column using toluene as a developing solvent, thereafter, the resultant toluene solution was poured into methanol (84 mL), to deposit a solid, and the resultant solid was filtrated. Using a Soxhlet extractor, the resultant solid was washed with acetone for 3 hours and dried, to obtain 194 mg of a polymer compound F. The resultant polymer compound F had a polystyrene-equivalent number-average molecular weight of $3.0 \times 10^4$ and a weight-average molecular weight of $5.4 \times 10^4$.

Example 13

Fabrication and Evaluation of Organic Film Solar Battery 4

An ink 4 was prepared and an organic film solar battery 4 was fabricated and evaluated in the same manner as in Example 5 excepting that the polymer compound D was used instead of the polymer compound A. Jsc (short circuit current density) was 2.73 mA/cm$^2$, Voc (open end voltage) was 0.736 V, ff (fill factor) was 0.643 and photoelectric conversion efficiency (η) was 1.29%. The results are shown in Table 1.

Example 14

Fabrication and Evaluation of Organic Film Solar Battery 5

An ink 5 was prepared and an organic film solar battery 5 was fabricated and evaluated in the same manner as in Example 5 excepting that the polymer compound E was used instead of the polymer compound A. Jsc (short circuit current density) was 7.45 mA/cm$^2$, Voc (open end voltage) was 0.860 V, ff (fill factor) was 0.573 and photoelectric conversion efficiency (η) was 3.67%. The results are shown in Table 1.

Example 15

Fabrication and Evaluation of Organic Film Solar Battery 6

An ink 6 was prepared and an organic film solar battery 6 was fabricated and evaluated in the same manner as in Example 5 excepting that the polymer compound F was used instead of the polymer compound A. Jsc (short circuit current density) was 3.05 mA/cm$^2$, Voc (open end voltage) was 0.621 V, ff (fill factor) was 0.726 and photoelectric conversion efficiency (η) was 1.38%. The results are shown in Table 1.

TABLE 1

| | | Jsc (mA/cm$^2$) | Voc (V) | ff | η (%) |
|---|---|---|---|---|---|
| Example 5 | organic film solar battery 1 (polymer compound A) | 6.16 | 0.848 | 0.677 | 3.53 |
| Example 6 | organic film solar battery 2 (polymer compound B) | 6.97 | 0.757 | 0.680 | 3.60 |
| Example 13 | organic film solar battery 4 (polymer compound D) | 2.73 | 0.736 | 0.643 | 1.29 |
| Example 14 | organic film solar battery 5 (polymer compound E) | 7.45 | 0.860 | 0.573 | 3.67 |
| Example 15 | organic film solar battery 6 (polymer compound F) | 3.05 | 0.621 | 0.726 | 1.38 |
| Comparative Example 2 | organic film solar battery 3 (polymer compound C) | 3.23 | 0.790 | 0.559 | 1.42 |

INDUSTRIAL APPLICABILITY

According to the present invention, a polymer compound which is useful for production of an organic film solar battery excellent in ff (fill factor) can be provided.

EXPLANATION OF NUMERALS

1 substrate
2 active layer
7a first electrode
7b first electrode
300 photoelectric conversion device

The invention claimed is:
1. A polymer compound comprising a structural unit represented by the formula (1):

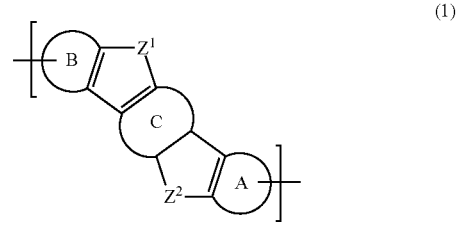

(1)

wherein
Ring A and Ring B represent each independently a heterocyclic ring, and the heterocyclic ring may have a substituent;
Ring C represents an aromatic hydrocarbon ring obtained by condensing two or more benzene rings, the aromatic hydrocarbon ring has two of an alkyl group, an alkoxy group, an alkylthio group, an amino group or a hydroxyl group, and these groups may have a substituent;
$Z^1$ and $Z^2$ represent each independently a group represented by the formula (Z-1), a group represented by the formula (Z-2), a group represented by the formula (Z-3), a group represented by the formula (Z-4) or a group represented by the formula (Z-5); and

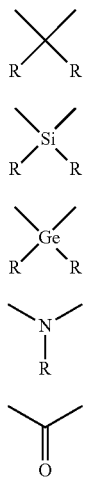

wherein

R represents an alkyl group, an alkoxy group, an alkylthio group, an aryl group or a mono-valent heterocyclic group, and these groups may have a substituent, and when there exist a plurality of R, these may be the same or different.

2. The polymer compound according to claim 1, wherein the structural unit represented by the formula (1) is a structural unit represented by the formula (2a):

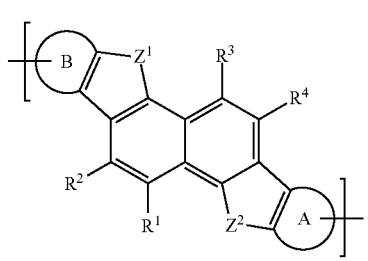

wherein

Ring A, Ring B, $Z^1$ and $Z^2$ represent the same meaning as described above; and $R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent; and here two selected from the group consisting of $R^1$, $R^2$, $R^3$ and $R^4$ is an alkyl group, an alkoxy group, an alkylthio group, an amino group or a hydroxyl group.

3. The polymer compound according to claim 2, wherein the structural unit represented by the formula (2a) is a structural unit represented by the formula (3a):

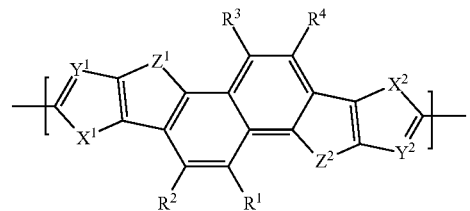

wherein $R^1$, $R^2$, $R^3$, $R^4$, $Z^1$ and $Z^2$ represent the same meaning as described above;

$X^1$ and $X^2$ represent each independently an oxygen atom, a sulfur atom or a selenium atom;

$Y^1$ and $Y^2$ represent each independently a nitrogen atom or a group represented by —$CR^5$=; and $R^5$ represents a hydrogen atom, an alkyl group, an alkoxy group, an alkylthio group, an aryl group, a mono-valent heterocyclic group or a halogen atom, and these groups may have a substituent.

4. The polymer compound according to claim 1, wherein the structural unit represented by the formula (1) is a structural unit represented by the formula (2b) or a structural unit represented by the formula (2c):

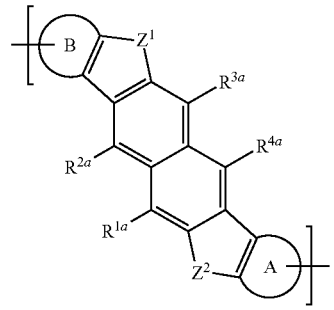

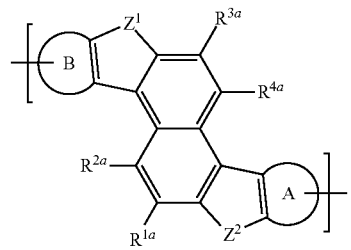

wherein

Ring A, Ring B, $Z^1$ and $Z^2$ represent the same meaning as described above; and $R^{1a}$, $R^{2a}$, $R^{3a}$ and $R^{4a}$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent; and here two selected from the group consisting of $R^{1a}$, $R^{2a}$, $R^{3a}$ and $R^{4a}$ in the formula (2b) is an alkyl group, an alkoxy group, an alkylthio group, an amino group or a hydroxyl group, and two selected from the group consisting of $R^{1a}$, $R^{2a}$, $R^{3a}$ and $R^{4a}$ in the formula (2c) is an alkyl group, an alkoxy group, an alkylthio group, an amino group or a hydroxyl group.

5. The polymer compound according to claim 3, wherein $X^1$ and $X^2$ are sulfur atoms.

6. The polymer compound according to claim 3, wherein $Y^1$ and $Y^2$ are groups represented by —CH=.

7. The polymer compound according to claim 1, wherein $Z^1$ and $Z^2$ are groups represented by the formula (Z-1).

8. The polymer compound according to claim 1, further comprising a structural unit represented by the formula (4) (different from the structural unit represented by the formula (1)):

  (4)

wherein
Ar represents an arylene group or a di-valent heterocyclic group, and these groups may have a substituent.

9. The polymer compound according to claim 8, wherein the polymer compound is an alternative copolymer composed of the structural unit represented by the formula (1) and the structural unit represented by the formula (4).

10. A compound represented by the formula (5a):

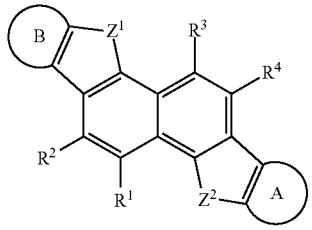  (5a)

wherein
Ring A and Ring B represent each independently a heterocyclic ring, and the heterocyclic ring may have a substituent;

$Z^1$ and $Z^2$ represent each independently a group represented by the formula (Z-1), a group represented by the formula (Z-2), a group represented by the formula (Z-3), a group represented by the formula (Z-4) or a group represented by the formula (Z-5);

$R^1$, $R^2$, $R^3$ and $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent; and here two selected from the group consisting of $R^1$, $R^2$, $R^3$ and $R^4$ is an alkyl group, an alkoxy group, an alkylthio group, an amino group or a hydroxyl group; and

  (Z-1)

  (Z-2)

  (Z-3)

(Z-4)

(Z-5)

wherein
R represents an alkyl group, an alkoxy group, an alkylthio group, an aryl group or a mono-valent heterocyclic group, and these groups may have a substituent; and when there exist a plurality of R, these may be the same or different.

11. The compound according to claim 10, wherein the compound represented by the formula (5a) is a compound represented by the formula (6a):

(6a)

wherein
$R^1$, $R^2$, $R^3$, $R^4$, $Z^1$ and $Z^2$ represent the same meaning as described above;
$R^6$ and $R^7$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group, an alkoxycarbonyl group, a borate residue, a boric acid residue or an organotin residue, and these groups may have a substituent;
$X^1$ and $X^2$ represent each independently an oxygen atom, a sulfur atom or a selenium atom;
$Y^1$ and $Y^2$ represent each independently a nitrogen atom or a group represented by —$CR^5$=; and
$R^5$ represents a hydrogen atom, an alkyl group, an alkoxy group, an alkylthio group, an aryl group, a mono-valent heterocyclic group or a halogen atom, and these groups may have a substituent.

12. An organic semiconductor material, comprising the polymer compound according to claim 1.

13. An organic semiconductor device having a first electrode and a second electrode and having an active layer between the first electrode and the second electrode, wherein the active layer contains the polymer compound according to claim 1.

14. The organic semiconductor device according to claim 13, wherein the organic semiconductor device is any of an organic transistor, a photoelectric conversion device, an organic electroluminescent device, an organic field-effect transistor sensor and an organic conductivity modulation sensor.

15. The organic semiconductor device according to claim 14, wherein the organic semiconductor device is a photoelectric conversion device.

16. A method comprising a step of contacting a compound represented by the formula (S16):

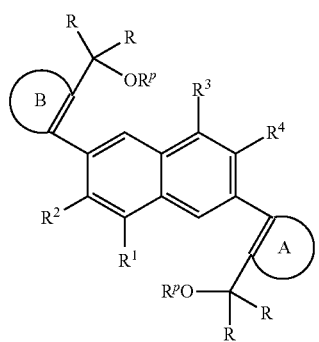

(S16)

wherein
- Ring A and Ring B represent each independently a heterocyclic ring, and the heterocyclic ring may have a substituent;
- $R^1$, $R^2$, $R^3$, $R^4$ represent each independently a hydrogen atom, an alkyl group, an alkoxy group, an alkylthio group, an aryl group, a mono-valent heterocyclic group, a halogen atom, a silyl group, an amino group, an alkenyl group, an alkynyl group, a hydroxyl group, a nitro group, a cyano group, a carboxyl group, an alkylcarbonyl group or an alkoxycarbonyl group, and these groups may have a substituent;
- R represents an alkyl group, an alkoxy group, an alkylthio group, an aryl group or a mono-valent heterocyclic group, and these groups may have a substituent; and when there exist a plurality of R, these may be the same or different;
- $R^p$ represents an alkyl group, a silyl group or an acetyl group; and when there exist a plurality of R, these may be the same or different;
with an acid to produce a compound represented by the formula (S7):

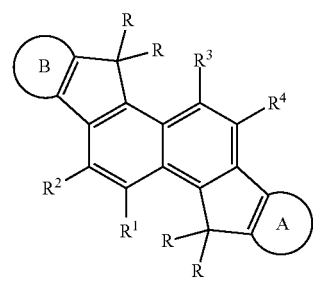

(S7)

wherein
Ring A, Ring B, R, $R^2$, $R^3$, $R^4$ and R represent the same meaning as described above.

* * * * *